United States Patent
Stahmann

(10) Patent No.: US 8,718,761 B2
(45) Date of Patent: May 6, 2014

(54) CARDIAC FUNCTION MANAGEMENT INTEGRATING CARDIAC CONTRACTILITY MODULATION

(75) Inventor: Jeffrey E. Stahmann, Ramsey, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 677 days.

(21) Appl. No.: 12/561,143

(22) Filed: Sep. 16, 2009

(65) Prior Publication Data

US 2010/0069985 A1    Mar. 18, 2010

Related U.S. Application Data

(60) Provisional application No. 61/097,420, filed on Sep. 16, 2008.

(51) Int. Cl.
*A61N 1/00* (2006.01)
*A61B 5/05* (2006.01)
*A61B 5/08* (2006.01)

(52) U.S. Cl.
USPC ............... 607/9; 607/17; 600/411; 600/484

(58) Field of Classification Search
USPC .............. 607/9, 17–18, 29, 46; 600/411, 484, 600/529
See application file for complete search history.

(56) References Cited

U.S. PATENT DOCUMENTS

| | | | |
|---|---|---|---|
| 4,590,941 A | 5/1986 | Saulson et al. | |
| 5,184,615 A | 2/1993 | Nappholz et al. | |
| 6,233,487 B1 | 5/2001 | Mika et al. | |
| 6,263,242 B1 | 7/2001 | Mika et al. | |
| 6,292,693 B1 | 9/2001 | Darvish et al. | |
| 6,298,268 B1 | 10/2001 | Ben-Haim et al. | |
| 6,317,631 B1 | 11/2001 | Ben-Haim et al. | |
| 6,330,476 B1 | 12/2001 | Ben-Haim et al. | |
| 6,360,126 B1 * | 3/2002 | Mika et al. | 607/9 |
| 6,370,430 B1 | 4/2002 | Mika et al. | |
| 6,424,866 B2 | 7/2002 | Mika et al. | |
| 6,459,928 B2 | 10/2002 | Mika et al. | |

(Continued)

FOREIGN PATENT DOCUMENTS

| WO | WO-00/27465 A1 | 5/2000 |
|---|---|---|
| WO | WO-01/30139 A2 | 5/2001 |

(Continued)

OTHER PUBLICATIONS

"Impulse Dynamics Announces Pivotal Results at the American College of Cardiology", *Reuters*, [online]. Retrieved from the Internet: <URL: http://www.reuters.com/article/pressRelease/idUS46033+29-Mar-2009+PRN20090329>, (Mar. 29, 2009), 2 pgs.

(Continued)

*Primary Examiner* — Christopher Koharski
*Assistant Examiner* — Catherine Voorhees
(74) *Attorney, Agent, or Firm* — Schwegman, Lundberg & Woessner, P.A.

(57) ABSTRACT

An implantable cardiac rhythm/function management system integrates cardiac contractility modulation (CCM) and one or more other therapies, such as to preserve device safety, improve efficacy, enhance sensing and detection, or enhance therapy effectiveness and delivery. Examples of the one or more other therapies can include pacing, defibrillation/cardioversion, cardiac resynchronization therapy (CRT), or neurostimulation.

20 Claims, 31 Drawing Sheets

(56) References Cited

U.S. PATENT DOCUMENTS

| | | | |
|---|---|---|---|
| 6,463,324 B1* | 10/2002 | Ben-Haim et al. | 607/9 |
| 6,480,737 B1 | 11/2002 | Policker et al. | |
| 6,587,721 B1 | 7/2003 | Prutchi et al. | |
| 6,597,952 B1 | 7/2003 | Mika et al. | |
| 6,675,043 B1 | 1/2004 | Prutchi et al. | |
| 6,725,093 B1 | 4/2004 | Ben-Haim et al. | |
| 6,993,385 B1 | 1/2006 | Routh et al. | |
| 7,027,863 B1 | 4/2006 | Prutchi et al. | |
| 7,167,748 B2 | 1/2007 | Ben-Haim et al. | |
| 7,187,970 B2 | 3/2007 | Shemer et al. | |
| 7,228,175 B2 | 6/2007 | Jain et al. | |
| 7,239,913 B2 | 7/2007 | Ding et al. | |
| 7,289,850 B2 | 10/2007 | Burnes | |
| 7,292,887 B2 | 11/2007 | Salo et al. | |
| 7,292,888 B2 | 11/2007 | Deno et al. | |
| 7,310,555 B2 | 12/2007 | Ben-Haim et al. | |
| 7,856,266 B1 | 12/2010 | Bornzin et al. | |
| 2003/0040777 A1 | 2/2003 | Shemer et al. | |
| 2003/0191503 A1 | 10/2003 | Zhu et al. | |
| 2005/0090871 A1 | 4/2005 | Cho | |
| 2006/0178589 A1 | 8/2006 | Dobak, III | |
| 2006/0212079 A1 | 9/2006 | Routh et al. | |
| 2006/0253161 A1 | 11/2006 | Libbus et al. | |
| 2007/0055184 A1 | 3/2007 | Echt et al. | |
| 2007/0060962 A1 | 3/2007 | Pappone | |
| 2007/0093875 A1 | 4/2007 | Chavan et al. | |
| 2007/0191901 A1 | 8/2007 | Schecter | |
| 2007/0191914 A1* | 8/2007 | Stessman | 607/63 |
| 2007/0250122 A1* | 10/2007 | Warkentin et al. | 607/4 |
| 2007/0270675 A1 | 11/2007 | Kane et al. | |
| 2008/0004669 A1 | 1/2008 | Sathaye et al. | |
| 2008/0039730 A1* | 2/2008 | Pu et al. | 600/484 |
| 2008/0046037 A1 | 2/2008 | Haubrich et al. | |
| 2008/0091256 A1* | 4/2008 | Libbus et al. | 607/149 |
| 2008/0132966 A1 | 6/2008 | Levin et al. | |
| 2008/0195165 A1 | 8/2008 | Stahmann et al. | |
| 2008/0215108 A1* | 9/2008 | Zhu et al. | 607/17 |
| 2008/0234772 A1 | 9/2008 | Shuros et al. | |
| 2008/0234774 A1 | 9/2008 | Baynham et al. | |
| 2009/0030471 A1 | 1/2009 | Rousso et al. | |
| 2009/0036943 A1* | 2/2009 | Signoff et al. | 607/36 |
| 2009/0099618 A1 | 4/2009 | Rousso et al. | |
| 2009/0105778 A1 | 4/2009 | Lee et al. | |
| 2009/0157146 A1* | 6/2009 | Linder et al. | 607/60 |
| 2009/0163966 A1 | 6/2009 | Perschbacher et al. | |
| 2010/0069977 A1* | 3/2010 | Stahmann | 607/4 |
| 2010/0069980 A1* | 3/2010 | Stahmann | 607/5 |
| 2010/0069984 A1* | 3/2010 | Stahmann | 607/9 |
| 2010/0152804 A1 | 6/2010 | Kleckner et al. | |

FOREIGN PATENT DOCUMENTS

| | | |
|---|---|---|
| WO | WO-01/30445 A1 | 5/2001 |
| WO | WO-01/76691 A1 | 10/2001 |
| WO | WO-01/87134 A2 | 11/2001 |
| WO | WO-2010033190 A2 | 3/2010 |
| WO | WO-2010033190 A3 | 3/2011 |

OTHER PUBLICATIONS

Abraham, W. T., et al., "A randomized controlled trial to evaluate the safety and efficacy of cardiac contractility modulation in patients with systolic heart failure: Rationale, design, and baseline patient characteristics", *American Heart Journal 156*(4), (Oct. 2008), 641-648.

Brunckhorst, C, B., et al., "Cardiac contractility modulation by non-excitatory currents: Studies in isolated cardiac muscle", *The European Journal of Heart Failure 8*, (Oct. 3, 2005), 7-15.

Burkhoff, D., et al., "Nonexcitatory electrical signals for enhancing ventricular contractility: rationale and initial investigations of an experimental treatment for heart failure.", *Am J Physiol Heart Circ Physiol.*, 288(6), (Jun. 2005), H2550-H2556.

Butter, C., et al., "First use of cardiac contractility modulation (CCM) in a patient failing CRT therapy: Clinical and technical aspects of combined therapies", *The European Journal of Heart Failure 9*, (Jun. 27, 2007), 955-958.

Daubert, J. C., "Modulation of cardiac contractility. A potential treatment of heart failure?", *European Heart Journal 29*, (Mar. 26, 2008), 961-963.

Imai, M., et al., "Therapy with cardiac contractility modulation electrical signals improves left ventricular function and remodeling in dogs with chronic heart failure.", *J Am Coll Cardiol.*, 49(21), (May 29, 2007), 2120-2128.

Kodama, M., et al., "Mechanical Alternans in Patients with Chronic Heart Failure", *Journal of Cardiac Failure 7*(2), (2001), 138-145.

Lawo, T., et al., "Electrical Signals Applied During the Absolute Refractory Period: An Investigative Treatment for Advanced Heart Failure in Patients with Normal QRS Duration", *Journal of the American College of Cardiology 46*(12), (Dec. 20, 2005), 2229-2236.

Mohri, S., et al., "Cardiac contractility modulation by electric currents applied during the refractory period.", *Am J Physiol Heart Circ Physiol*. May 2002;282(5):, (May 2002), H1642-H1647.

Pappone, C., et al., "Cardiac contractility modulation by electric currents applied during the refractory period in patients with heart failure secondary to ischemic or idiopathic dilated cardiomyopathy.", *Am J Cardiol.*, 90(12), (Dec. 15, 2002), 1307-1313.

Sabbah, H. N., et al., "Cardiac contractility modulation with the impulse dynamics signal: studies in dogs with chronic heart failure.", *Heart Fail Rev.*, 6(1), (Jan. 2001), 45-53.

Salazar, C., et al., "Biventricular and Novel Pacing Mechanisms in Heart Failure", *Current Heart Failure Reports 6*, (2009), 14-18.

Schmidt, A. G., et al., "Cardiac-specific Overexpression of Calsequestrin REsults in Left Ventricular Hypertrophy, Depressed Force-frequency Relation and Pulsus Alternans In Vivo", *J Mol Cell Cardiol 32*, (2000), 1735-1744.

Stix, G., et al., "Chronic electrical stimulation during the absolute refractory period of the myocardium improves severe heart failure", *Eur Heart J.*, 25(8), (Apr. 2004), 650-655.

Willems, Rik, et al., "Nonexcitatory stimulation as a novel treatment for heart failure: cause for excitement?", *European Heart Journal 25*, (2004), 626-628.

"U.S. Appl. No. 12/561,124, Non-Final Office Action mailed Aug. 19, 2011", 16 pgs.

"U.S. Appl. No. 12/561,124, Response filed Nov. 11, 2011 to Non-Final Office Action mailed Aug. 19, 2011", 20 pgs.

"U.S. Appl. No. 12/561,128, Non-Final Office Action mailed Sep. 1, 2011", 17 pgs.

"U.S. Appl. No. 12/561,128, Response filed Jan. 3, 2012 to Non-Final Office Action mailed Sep. 1, 2011", 24 pgs.

"U.S. Appl. No. 12/561,137, Non-Final Office Action mailed Sep. 7, 2011", 15 pgs.

"U.S. Appl. No. 12/561,137, Response filed Jan. 5, 2012 to Non-Final Office Action mailed Sep. 7, 2011", 20 pgs.

"International Application Serial No. PCT/US2009/005165, International Preliminary Report on Patentability mailed Mar. 31, 2011", 16 pgs.

"International Application Serial No. PCT/US2009/005165, International Search Report mailed Jan. 17, 2011", 7 pgs.

"International Application Serial No. PCT/US2009/005165, Invitation to Pay Additional Fee mailed Oct. 28, 2010", 7 pgs.

"International Application Serial No. PCT/US2009/005165, Written Opinion mailed Jan. 17, 2011", 15 pgs.

* cited by examiner

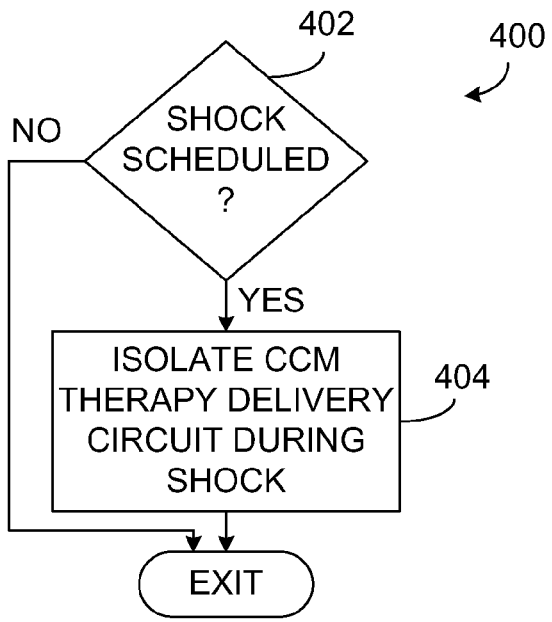
FIG. 4
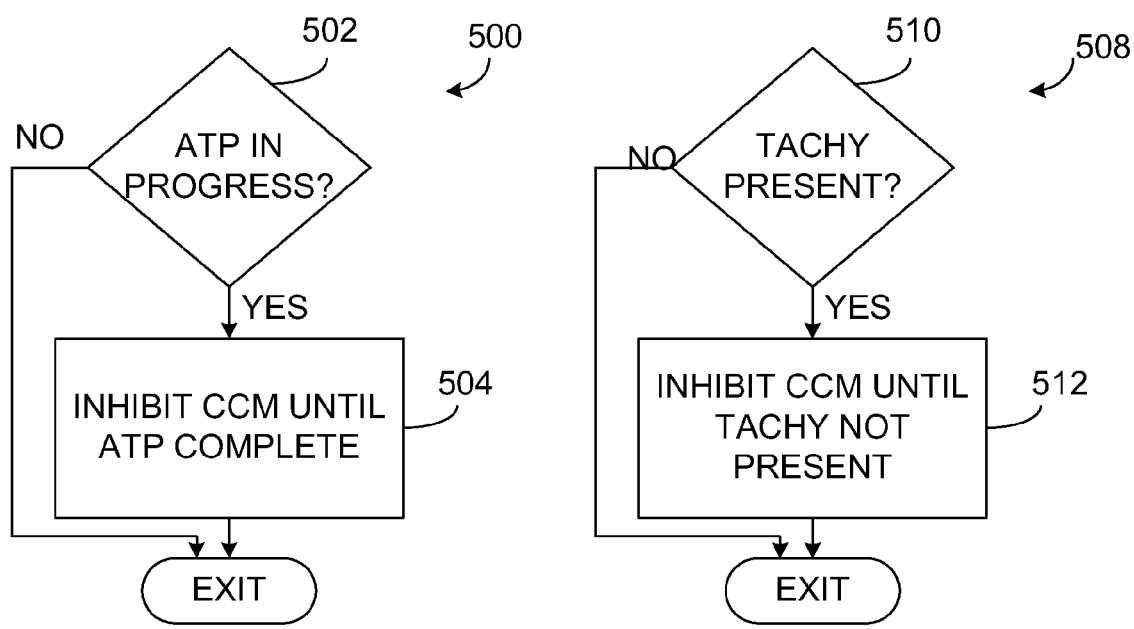
FIG. 5A          FIG. 5B

CARDIAC FUNCTION MANAGEMENT INTEGRATING CARDIAC CONTRACTILITY MODULATION

CLAIM OF PRIORITY

Benefit of priority is hereby claimed to U.S. Provisional Patent Application Ser. No. 61/097,420, filed on Sep. 16, 2008, which application is incorporated herein by reference.

BACKGROUND

An implantable pacer can be used for pacing a heart. An example of pacing can include bradycardia pacing, which can deliver an electrostimulation pulse to the heart to evoke a responsive heart contraction, such as to maintain a fast enough heart rate to provide a cardiac output of blood to meet a patient's metabolic need. Another example of pacing can also include antitachyarrhythmia pacing (ATP), which can include delivering a quick sequence of electrostimulations, such as to "overdrive" a too-fast tachyarrhythmic heart rhythm so that the ATP pulses take control of the heart rhythm; then the ATP pulse rate can be lowered to an appropriate heart rate.

An implantable cardiac resynchronization therapy (CRT) device can be used for spatially coordinating heart contractions. CRT can include delivering electrostimulations to maintain one or more of atrioventricular (AV) timing, interatrial timing (LA-RA) timing, interventricular timing (LV-RV), intraventricular timing, or the like.

An implantable defibrillator can be used for delivering a higher-energy cardioversion shock to interrupt an abnormal heart rhythm, such as an atrial or ventricular tachyarrhythmia or fibrillation.

A cardiac contractility modulation (CCM) device can be used for delivering an non-stimulatory energy to the heart to increase heart contractility (since a stronger heart contraction can also help increase cardiac output, along with a higher contraction rate, and proper AV or other synchrony) rather than to increase the heart rate (like pacing) or to spatially synchronize a heart contraction (like CRT). In CCM therapy, electrical energy is typically delivered to the heart during a refractory period of the heart, such as a time immediately following a heart contraction. During a refractory period, the heart tissue is insensitive to electrostimulation in that electrostimulations delivered during the refractory period do not evoke a resulting heart contraction. However, the CCM electrical energy delivered during the refractory period, although it does not evoke a responsive heart contraction, is believed to be capable of increasing heart contractility, such that the next heart contraction can be more forceful, which should help yield better cardiac output.

There are two refractory periods associated with ventricular cardiac tissue, an absolute refractory period and a relative refractory period. The absolute ventricular refractory period begins at the start of the action potential and includes the QRS complex and the positive going portion of the T wave. The relative refractory period occurs during the negative going portion of the T wave. During the absolute ventricular refractory period ventricular tissue cannot be stimulated to begin another action potential (or resulting contraction). During the relative ventricular refractory period, ventricular tissue can be stimulated to begin another action potential (and the resulting contraction), however a larger stimulus than normal is typically required. Further, delivery of electrical energy during the relative refractory period can be proarrhythmic.

Since is it intended that CCM therapy directed at proarrhythmic tissue not trigger ventricular contractions, the electrical energy associated with proarrhythmic CCM therapy is preferably delivered during the absolute ventricular refractory period. Further the energy associated with CCM therapy directed at atrial tissue would be delivered during the absolute atrial refectory period.

OVERVIEW

The present inventor has recognized, among other things, that integrating CCM therapy in a cardiac function management device with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.) can present serious integration challenges, and, in some cases, the potential for deleterious effects if not mitigated. With this in mind, the present inventor has created an integrated cardiac function management device that can include one or more features to help use CCM therapy in combination with other cardiac function management therapy or functionality, such as described in detail in this document.

As described elsewhere in this document, an implantable cardiac rhythm/function management system can integrate CCM and one or more other therapies, such as to preserve device safety, improve efficacy, enhance sensing and detection, or enhance therapy effectiveness and delivery. Examples of the one or more other therapies can include pacing, defibrillation/cardioversion, cardiac resynchronization therapy (CRT), or neurostimulation.

Example 1 includes an implantable cardiac rhythm/function management device comprising: a cardiac contractility modulation (CCM) therapy circuit configured to deliver a non-stimulatory electrical energy during a refractory period of the heart; a non-CCM cardiac therapy circuit configured to deliver non-CCM therapy; and a controller circuit, coupled to the CCM therapy circuit and the non-CCM therapy circuit, the controller circuit configured to adjust at least one of a CCM therapy or a non-CCM therapy using information about the other of the CCM therapy or the non-CCM therapy.

In Example 2, the device of Example 1 optionally includes the controller circuit configured to defer CCM therapy until at least one of: (1) a recharge pulse is competed; (2) a cardiac arrhythmia assessment is completed; (3) a neural stimulation is completed; or (4) a defibrillation shock is completed.

In Example 3, the device of any one of Examples 1-2 optionally includes an electrostimulation therapy circuit; wherein the controller circuit is configured to adjust an electrostimulation energy using information about whether a CCM condition is present.

In Example 4, the device of any one of Examples 1-3 optionally includes the controller configured to determine whether a CCM condition is present and to deem a CCM condition to be present when (a) CCM has been delivered within a specified preceding time period or (b) CCM is enabled.

In Example 5, the device of any one of Examples 1-4 optionally includes the controller configured to determine an electrostimulation threshold energy when at least one CCM condition is present.

In Example 6, the device of any one of Examples 1-5 optionally includes the controller configured to deliver the electrostimulation therapy at or above the electrostimulation threshold energy when at least one CCM condition is present.

In Example 7, the device of any one of Examples 1-6 optionally includes the controller configured to deliver the electrostimulation therapy at a specified energy derived from the electrostimulation threshold energy when no CCM condition is present.

In Example 8, the device of any one of Examples 1-7 optionally includes the controller configured to determine an electrostimulation threshold energy when no CCM condition is present.

In Example 9, the device of any one of Examples 1-8 optionally includes the controller configured to deliver the electrostimulation therapy at a specified energy derived from the electrostimulation threshold energy when at least one CCM condition is present.

In Example 10, the device of any one of Examples 1-9 optionally includes the controller configured to deliver the electrostimulation therapy at or above the electrostimulation threshold energy when no CCM condition is present.

In Example 11, the device of any one of Examples 1-10 optionally includes an electrostimulation therapy circuit; and wherein the controller circuit is configured to coordinate delivery of CCM therapy with at least one of issuing a recharge pulse or configuring a coupling capacitor.

In Example 12, the device of any one of Examples 1-11 optionally includes the controller circuit configured to inhibit concurrent delivery of CCM therapy and the recharge pulse to the same location.

In Example 13, the device of any one of Examples 1-12 optionally includes the controller circuit configured to trigger delivery of CCM, then trigger issuing a recharge pulse, before then triggering delivery of an electrostimulation during the same cardiac cycle.

In Example 14, the device of any one of Examples 1-13 optionally includes the controller circuit configured to trigger issuing a recharge before discharging a CCM residual charge.

In Example 15, the device of any one of Examples 1-14 optionally includes the controller circuit configured to trigger delivery of CCM, then configure a coupling capacitor, before then triggering delivery of an electrostimulation.

In Example 16, the device of any one of Examples 1-15 optionally includes the controller circuit configured to trigger delivering an electrostimulation, then trigger delivering a CCM, before then triggering a recharge to discharge electrostimulation and CCM residual charge.

In Example 17, the device of any one of Examples 1-16 optionally includes the controller circuit configured to trigger delivering an electrostimulation, then configuring a coupling capacitor for delivering CCM, then trigger delivering the CCM, before then triggering a recharge to discharge electrostimulation and CCM residual charge.

In Example 18, the device of any one of Examples 1-17 optionally includes the controller configured to configure the coupling capacitor such that a residual CCM energy upon a coupling capacitor is additive to energy delivered during an electrostimulation.

In Example 19, the device of any one of Examples 1-18 optionally includes at least one of an autothreshold or autocapture circuit; wherein the controller circuit is configured to use information about whether CCM is enabled and whether at least one of autocapture or autothreshold is enabled to do at least one of the following: (1) suspend CCM during autothreshold or autocapture; (2) perform autothreshold or autocapture when CCM is inactive; or (3) assign non-conflicting electrode configurations to the CCM and at least one of the autothreshold or autocapture.

In Example 20, the device of any one of Examples 1-19 optionally includes at least one of an autothreshold or autocapture circuit; wherein the controller circuit is configured to: (1) detect a change in a electrostimulation capture threshold energy; and (2) adjust CCM therapy using information about the change in the electrostimulation capture threshold energy.

In Example 21, the device of any one of Examples 1-20 optionally includes a ventricular potential sensing circuit; wherein the ventricular potential sensing circuit is configured to sense at least one of an evoked potential or an intrinsic potential; and wherein the controller circuit is configured to: (1) detect a change in ventricular potential, the change in ventricular potential including at least one of a change in a magnitude, timing, or morphology of a ventricular potential; and (2) adjust CCM therapy using information about a change in ventricular potential.

In Example 22, the device of any one of Examples 1-21 optionally includes at least one of a pacing or defibrillation threshold determination circuit; wherein the controller circuit is configured to control CCM therapy during at least one of pacing or defibrillation threshold testing.

In Example 23, the device of any one of Examples 1-22 optionally includes the controller circuit configured to inhibit CCM therapy during at least one of pacing or defibrillation threshold testing.

In Example 24, the device of any one of Examples 1-22 optionally includes the controller circuit configured to trigger providing CCM therapy during at least one of pacing or defibrillation threshold testing.

In Example 25, the device of any one of Examples 1-24 optionally includes an intrinsic cardiac signal sensing circuit; wherein the controller circuit is configured to coordinate CCM therapy delivery and intrinsic heart signal sensing by adjusting at least one of: CCM energy, CCM delivery timing, CCM delivery location, or CCM electrode configuration, differently based on whether a preceding beat was a paced beat or a sensed beat.

In Example 26, the device of any one of Examples 1-25 optionally includes the controller circuit configured to delay CCM delivery timing following a paced beat compared to CCM delivery timing following an intrinsic beat.

In Example 27, the device of any one of Examples 1-26 optionally includes an intrinsic cardiac signal sensing circuit; wherein the controller circuit is configured to coordinate CCM therapy delivery and intrinsic heart signal sensing by adjusting at least one of: CCM energy, CCM delivery timing, CCM delivery location, or CCM electrode configuration, differently based on which cardiac chamber is paced.

In Example 28, the device of any one of Examples 1-27 optionally includes the controller circuit configured to: (a) deliver CCM therapy after a first timing delay when CCM therapy is delivered to a first cardiac chamber and pacing therapy is delivered to a different second cardiac chamber; and (b) deliver CCM therapy after a second timing delay when CCM therapy and pacing therapy are delivered to the same cardiac chamber; wherein the first timing delay is longer than the second timing delay.

Example 29 includes an implantable cardiac rhythm/function management device comprising: a cardiac contractility modulation (CCM) therapy circuit configured to deliver a non-stimulatory electrical energy during a refractory period of the heart; a tachyarrhythmia circuit, configured to perform a tachyarrhythmia function comprising at least one of detecting a tachyarrhythmia or delivering tachyarrhythmia therapy; and a controller circuit, coupled to the CCM therapy circuit and the tachyarrhythmia circuit, the controller circuit configured to adjust at least one of a CCM therapy or the tachyarrhythmia function using information about the other of the CCM therapy or the tachyarrhythmia function.

In Example 30, the device of Example 29 optionally includes a shock therapy circuit configured to deliver shock therapy; wherein the controller circuit is configured to isolate the CCM therapy circuit from shock therapy circuit during shock therapy delivery.

In Example 31, the device of any one of Examples 29 or 30 optionally includes the tachyarrhythmia circuit configured to detect a tachyarrhythmia using an intrinsic cardiac signal morphology analysis circuit; wherein the controller circuit is configured to adjust the morphology analysis using information about whether a CCM condition is present; and wherein a CCM condition is deemed present if (a) CCM has been delivered within a specified preceding time period or (b) CCM is enabled.

In Example 32, the device of any one of Examples 29-31 optionally includes the controller circuit configured to select a morphology template based on whether a CCM condition is present.

In Example 33, the device of any one of Examples 29-32 optionally includes the controller configured such that, when CCM is enabled, the controller circuit is configured to select a morphology template obtained with CCM having been enabled.

In Example 34, the device of one of Examples 29-33 optionally includes the controller configured such that, when a CCM condition is present, morphology analysis is disabled.

Example 35 includes an implantable cardiac rhythm/function management device comprising: a cardiac contractility modulation (CCM) therapy circuit configured to deliver a non-stimulatory electrical energy during a refractory period of the heart; a physiologic sensor circuit configured to sense a physiologic parameter; and a controller circuit, coupled to the CCM therapy circuit and the physiologic sensor circuit, the controller circuit configured to adjust a CCM therapy using information about the sensed physiologic parameter.

In Example 36, the device of Example 35 optionally includes the physiologic sensor circuit configured to sense an indication of a measure of at least one of a renal or cardiac function.

In Example 37, the device of any one of Examples 35-36 optionally includes the controller circuit configured to use information about the renal or cardiac function to adjust at least one of CCM energy, CCM delivery timing, CCM delivery location, or CCM electrode configuration.

In Example 38, the device of any one of Examples 35-37 optionally includes an electrolyte sensor configured to detect an indication of a measure of at least one of: potassium, sodium, calcium, chloride, or bicarbonate.

In Example 39, the device of any one of examples Example 35-38 optionally includes the controller circuit configured to use information about the measure of the least one of potassium, sodium, calcium, chloride, or bicarbonate, to adjust at least one of CCM energy, CCM delivery timing, CCM delivery location, or CCM electrode configuration.

In Example 40, the device of any one of Examples 35-39 optionally includes the physiologic sensor circuit configured to detect an indication of a measure of at least one of: blood urea nitrogen, serum creatinine, or glomerular filtration rate.

In Example 41, the device of any one of Examples 35-40 optionally includes the controller circuit configured to use information about the measure of the at least one of: blood urea nitrogen, serum creatinine, or glomerular filtration rate, to adjust at least one of CCM energy, CCM delivery timing, CCM delivery location, or CCM electrode configuration.

In Example 42, the device of any one of Examples 35-41 optionally includes a neural sensor configured to sense a neural signal.

In Example 43, the device of any one of Examples 35-42 optionally includes the controller circuit configured to use information about the neural signal to adjust at least one of CCM energy, CCM delivery timing, CCM delivery location, or CCM electrode configuration.

In Example 44, the device of any one of Examples 35-43 optionally includes the neural sensor configured to sense a neural signal from a vagal nerve; wherein the neural signal from the vagal nerve includes an indication of one of an increase or a decrease in vagal nerve activity.

In Example 45, the device of any one of Examples 35-44 optionally includes the controller circuit configured such that, when the neural signal indicates an increase in vagal nerve activity, the controller circuit is configured to increase at least one of CCM energy or frequency of CCM delivery.

In Example 46, the device of any one of Examples 35-45 optionally includes the neural sensor configured to monitor at least one of sympathetic nerve activity or parasympathetic nerve activity; wherein the neural signal includes an indication of at least one of: an increase in sympathetic nerve activity, a decrease in sympathetic nerve activity, an increase in parasympathetic nerve activity, or a decrease in parasympathetic nerve activity.

In Example 47, the device of any one of Examples 35-46 optionally includes the controller circuit configured such that, when the neural signal indicates at least one of an increase in parasympathetic nerve activity or a decrease in sympathetic nerve activity, the controller circuit is configured to increase at least one of CCM energy or frequency of CCM delivery.

In Example 48, the device of any one of Examples 35-47 optionally includes the controller circuit configured such that, when the neural signal indicates at least one of an increase in sympathetic nerve activity or a decrease in parasympathetic nerve activity, the controller circuit is configured to decrease at least one of CCM energy or frequency of CCM delivery.

In Example 49, the device of any one of Examples 35-48 optionally includes a neural stimulation circuit configured to deliver neural stimulation therapy.

In Example 50, the device of any one of Examples 35-49 optionally includes the controller circuit configured to adjust at least one of the CCM therapy or the neural stimulation therapy using information about the other of the CCM therapy or the neural stimulation therapy.

In Example 51, the device of any one of Examples 35-50 optionally includes the controller circuit configured to adjust at least one of the CCM therapy or the neural stimulation therapy using information about the sensed physiologic parameter.

Example 52 includes an apparatus comprising: an implantable cardiac rhythm/function management device comprising: a cardiac contractility modulation (CCM) therapy circuit configured to deliver a non-stimulatory electrical energy during a refractory period of the heart; an adverse event detector circuit; and a controller circuit, coupled to the CCM therapy circuit and the adverse event detector circuit, the controller circuit configured to adjust a CCM therapy using information about an adverse event from the adverse event detector circuit In Example 53, the apparatus of Example 52 optionally includes a non-CCM therapy circuit configured to deliver non-CCM therapy; wherein the adverse event detector circuit comprises a battery status circuit; and wherein the controller circuit is configured to use battery status information obtained from the battery status circuit to reconfigure which of multiple batteries services at least one of the non-CCM therapy circuit or the CCM therapy circuit.

In Example 54, the apparatus of any one of Examples 52 or 53 optionally includes a non-CCM therapy circuit configured to deliver non-CCM therapy; wherein the adverse event detector circuit comprises a battery status circuit; and wherein the controller circuit is configured to use battery status information obtained from the battery status circuit to preferentially terminate delivery of one of the CCM therapy or the non-CCM therapy over the other of the CCM therapy or the non-CCM therapy.

In Example 55, the apparatus of any one of Examples 52-54 optionally includes a neurostimulation therapy circuit configured to deliver neurostimulation therapy; wherein the adverse event detector circuit is configured to detect an adverse event associated with at least one of neurostimulation or CCM; and wherein the controller circuit is configured to adjust at least one of the CCM therapy or the neurostimulation therapy based on information from the adverse event detector circuit.

In Example 56, the apparatus of any one of Examples 52-55 optionally includes the controller circuit configured such that when neurostimulation is enabled and an adverse event associated with the neurostimulation occurs, then the controller circuit (a) turns off neural stimulation when CCM is enabled; (b) enables CCM when CCM is not enabled and does not disable neural stimulation; or (c) enables CCM when CCM is not enabled and disables neural stimulation.

In Example 57, the apparatus of any one of Examples 52-56 optionally includes the controller circuit configured such that when CCM is enabled and an adverse event associated with the CCM occurs, then the controller circuit (a) turns off CCM when neurostimulation is enabled; (b) turns on neurostimulation when neurostimulation is not enabled and does not disable CCM; or (c) enables neurostimulation when neurostimulation is not enabled and disables CCM.

In Example 58, the apparatus of any one of Examples 52-57 optionally includes the adverse event detector comprising a physiologic sensor.

In Example 59, the apparatus of any one of Examples 52-58 optionally includes the physiologic sensor configured to detect pulsus alternans; wherein the controller is configured to adjust at least one of CCM energy, CCM delivery timing, CCM delivery location, or CCM electrode configuration in response to the detection of pulsus alternans.

In Example 60, the apparatus of any one of Examples 52-59 optionally includes the controller configured to increase at least one of CCM energy or frequency of CCM delivery in response to the detection of pulsus alternans.

In Example 61, the apparatus of any one of Examples 52-60 optionally includes the adverse event detector circuit comprising a user interface to receive user-input information about the adverse event.

In Example 62, the apparatus of any one of Examples 52-61 optionally includes the adverse event detector circuit comprising a CCM trigger detector circuit configured to detect a CCM trigger condition for enabling CCM; wherein the controller circuit is configured to enable the CCM therapy when at least one CCM trigger is detected.

In Example 63, the apparatus of any one of Examples 52-62 optionally includes the CCM trigger condition including at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

In Example 64, the apparatus of any one of Examples 52-63 optionally includes the CCM trigger condition including an indication of worsening heart failure.

In Example 65, the apparatus of any one of Examples 52-64 optionally includes the CCM trigger condition including an indication of an enabling or disabling of a device-based heart failure therapy other than CCM therapy.

In Example 66, the apparatus of any one of Examples 52-65 optionally includes the adverse event detector circuit comprising a CCM stressor detector circuit configured to detect a CCM stressor for disabling CCM; wherein the controller circuit is configured to disable CCM when at least one CCM stressor is detected.

In Example 67, the apparatus of any one of Examples 52-66 optionally includes the CCM stressor condition including at least one of: a detection of sleep disordered breathing, a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

In Example 68, the apparatus of any one of Examples 52-67 optionally includes the CCM stressor condition including an indication of enabling or disabling of a device-based heart failure therapy other than CCM therapy.

In Example 69, the apparatus of any one of Examples 52-68 optionally includes the CCM stressor condition including a detected physical activity level that exceeds a specified threshold value.

In Example 70, the apparatus of any one of Examples 52-69 optionally includes the adverse event detector circuit comprising: a CCM trigger detector circuit configured to detect a CCM trigger condition for enabling CCM, and a CCM stressor detector circuit configured to detect a CCM stressor for disabling CCM; wherein the controller circuit is configured to enable the CCM therapy when at least one CCM trigger is detected and to disable CCM when at least one CCM stressor is detected.

In Example 71, the apparatus of any one of Examples 52-70 optionally includes the CCM trigger condition including at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

In Example 72, the apparatus of any one of Examples 52-71 optionally includes the CCM trigger condition including an indication of worsening heart failure.

In Example 73, the apparatus of any one of Examples 52-72 optionally includes the CCM trigger condition including an indication of an enabling or disabling of a device-based heart failure therapy other than CCM therapy.

In Example 74, the apparatus of any one of Examples 52-73 optionally includes the CCM stressor condition including at least one of: a detection of sleep disordered breathing, a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

In Example 75, the apparatus of any one of Examples 52-74 optionally includes the CCM stressor condition including an indication of enabling or disabling of a device-based heart failure therapy other than CCM therapy.

In Example 76, the apparatus of any one of Examples 52-75 optionally includes the CCM stressor condition including a detected physical activity level that exceeds a specified threshold value.

Example 77 includes a method comprising: delivering a cardiac contractility modulation (CCM) therapy, wherein delivering the CCM therapy comprises delivering a non-stimulatory electrical energy during a refractory period of the heart; delivering a non-CCM therapy; and adjusting at least one of the CCM therapy or the non-CCM therapy using information about the other of the CCM therapy or the non-CCM therapy.

In Example 78, the method of Example 77 optionally includes deferring delivering the CCM therapy until at least one of: (1) a recharge pulse is competed; (2) a cardiac arrhythmia assessment is completed; (3) a neural stimulation is completed; or (4) a defibrillation shock is completed.

In Example 79, the method of any one of Examples 77 or 78 optionally includes delivering an electrostimulation therapy; and wherein adjusting at least one of the CCM therapy or the non-CCM therapy includes adjusting an electrostimulation energy using information about whether a CCM condition is present.

In Example 80, the method of any one of Examples 77-79 optionally includes deeming a CCM condition to be present when (a) CCM has been delivered within a specified preceding time period or (b) CCM is enabled.

In Example 81, the method of any one of Examples 77-80 optionally includes determining a electrostimulation threshold energy when at least one CCM condition is present.

In Example 82, the method of any one of Examples 77-81 optionally includes delivering the non-CCM electrostimulation therapy at or above the electrostimulation threshold energy when at least one CCM condition is present.

In Example 83, the method of any one of Examples 77-82 optionally includes delivering the electrostimulation therapy at a specified energy derived from the electrostimulation threshold energy when no CCM condition is present.

In Example 84, the method of any one of Examples 77-83 optionally includes determining a electrostimulation threshold energy when no CCM condition is present.

In Example 85, the method of any one of Examples 77-84 optionally includes delivering electrostimulation therapy at a specified energy derived from the electrostimulation threshold energy when at least one CCM condition is present.

In Example 86, the method of any one of Examples 77-85 optionally includes delivering the electrostimulation therapy at or above the electrostimulation threshold energy when no CCM condition is present.

In Example 87, the method of any one of Examples 77-86 optionally includes delivering the non-CCM therapy includes delivering electrostimulation therapy; wherein delivering the CCM therapy includes coordinating CCM therapy with at least one of issuing a recharge pulse or configuring a coupling capacitor.

In Example 88, the method of any one of Examples 77-87 optionally includes inhibiting concurrent delivery of CCM therapy and the recharge pulse to the same location.

In Example 89, the method of any one of Examples 77-88 optionally includes triggering delivery of CCM, then triggering issuing a recharge pulse, before then triggering delivery of an electrostimulation during the same cardiac cycle.

In Example 90, the method of any one of Examples 77-89 optionally includes triggering issuing a recharge before discharging a CCM residual charge.

In Example 91, the method of any one of Examples 77-90 optionally includes triggering delivery of CCM, then configuring a coupling capacitor, before then triggering delivery of an electrostimulation.

In Example 92, the method of any one of Examples 77-91 optionally includes triggering delivering an electrostimulation, then triggering delivering a CCM, before then triggering a recharge to discharge electrostimulation and CCM residual charge.

In Example 93, the method of any one of Examples 77-92 optionally includes triggering trigger delivering an electrostimulation, then configuring a coupling capacitor for delivering CCM, then trigger delivering the CCM, before then triggering a recharge to discharge electrostimulation and CCM residual charge.

In Example 94, the method of any one of Examples 77-93 optionally includes configuring the coupling capacitor such that a residual CCM energy upon a coupling capacitor is additive to energy delivered during an electrostimulation.

In Example 95, the method of any one of Examples 77-94 optionally includes performing at least one of an autothreshold or autocapture function; wherein adjusting at least one of the CCM therapy or the non-CCM therapy includes using information about whether CCM therapy is enabled and about whether at least one of autothreshold or autocapture is enabled to do at least one of the following: (1) suspend CCM during autothreshold or autocapture; (2) perform autothreshold or autocapture when CCM is inactive; or (3) assign non-conflicting electrode configurations to the CCM and at least one of the autothreshold or autocapture.

In Example 96, the method of any one of Examples 77-95 optionally includes performing at least one of an autothreshold or autocapture function; wherein adjusting at least one of the CCM therapy or the non-CCM therapy includes: (1) detecting a change in a electrostimulation capture threshold energy; and (2) adjusting CCM therapy using information about the change in the electrostimulation capture threshold energy.

In Example 97, the method of any one of Examples 77-96 optionally includes sensing at least one of an evoked potential or an intrinsic potential;
wherein adjusting at least one of the CCM therapy or the non-CCM therapy includes: (1) detecting a change in the at least one evoked potential or intrinsic potential, the change including at least one of a change in a magnitude, timing, or morphology of the at least one evoked potential or intrinsic potential; and (2) adjusting CCM therapy using information about a change in the at least one evoked potential or intrinsic potential.

In Example 98, the method of any one of Examples 77-97 optionally includes determining at least one of a pacing or defibrillation threshold; wherein adjusting at least one of the CCM therapy or the non-CCM therapy includes controlling CCM therapy during at least one of pacing or defibrillation threshold testing.

In Example 99, the method of any one of Examples 77-98 optionally includes inhibiting CCM therapy during at least one of pacing or defibrillation threshold testing.

In Example 100, the method of any one of Examples 77-99 optionally includes triggering providing CCM therapy during at least one of pacing or defibrillation threshold testing.

In Example 101, the method of any one of Examples 77-100 optionally includes sensing an intrinsic cardiac signal; wherein adjusting at least one of the CCM therapy or the non-CCM therapy includes coordinating CCM therapy delivery and intrinsic heart signal sensing by adjusting at least one of: CCM energy, CCM delivery timing, CCM delivery location, or CCM electrode configuration, differently based on whether a preceding beat was a paced beat or a sensed beat.

In Example 102, the method any one of Examples 77-101 optionally includes delaying CCM delivery timing following a paced beat compared to CCM delivery timing following an intrinsic beat.

In Example 103, the method of any one of Examples 77-102 optionally includes sensing an intrinsic cardiac signal; wherein adjusting at least one of the CCM therapy or the non-CCM therapy includes coordinating CCM therapy delivery and intrinsic heart signal sensing by adjusting at least one of: CCM energy, CCM delivery timing, CCM delivery location, or CCM electrode configuration, differently based on which cardiac chamber is paced.

In Example 104, the method of any one of Examples 77-103 optionally includes: (a) delivering CCM therapy after a first timing delay when CCM therapy is delivered to a first cardiac chamber and pacing therapy is delivered to a different second cardiac chamber; and (b) delivering CCM therapy after a second timing delay when CCM therapy and pacing therapy are delivered to the same cardiac chamber; wherein the first timing delay is longer than the second timing delay.

Example 105 includes a method comprising: delivering a cardiac contractility modulation (CCM) therapy, wherein delivering the CCM therapy comprises delivering a non-stimulatory electrical energy during a refractory period of the heart; performing a tachyarrhythmia function comprising at least one of detecting a tachyarrhythmia or delivering tachyarrhythmia therapy; and adjusting at least one of the CCM therapy or the tachyarrhythmia function using information about the other of the CCM therapy or the tachyarrhythmia function.

In Example 106, the method of Example 105 optionally includes delivering tachyarrhythmia therapy; wherein delivering tachyarrhythmia therapy comprises delivering shock therapy; and wherein adjusting at least one of the CCM therapy or the tachyarrhythmia function comprises isolating CCM therapy delivery from shock therapy delivery.

In Example 107, the method of any one of Examples 105 or 106 optionally includes detecting a tachyarrhythmia using an intrinsic cardiac signal morphology analysis circuit; wherein adjusting at least one of the CCM therapy or the tachyarrhythmia function comprises adjusting the morphology analysis using information about whether a CCM condition is present; and wherein a CCM condition is deemed present if (a) CCM has been delivered within a specified preceding time period or (b) CCM is enabled.

In Example 108, the method of any one of Examples 105-107 optionally includes selecting a morphology template based on whether a CCM condition is present.

In Example 109, the method of any one of Examples 105-108 optionally includes, when CCM is enabled, selecting a morphology template comprises selecting a morphology template obtained with CCM having been enabled.

In Example 110, the method of any one of Examples 105-109 optionally includes disabling the morphology analysis when a CCM condition is present.

Example 111 includes a method comprising: delivering a cardiac contractility modulation (CCM) therapy, wherein delivering the CCM therapy comprises delivering a non-stimulatory electrical energy during a refractory period of the heart; sensing a physiologic parameter; and adjusting the CCM therapy using information about the sensed physiologic parameter.

In Example 112, the method of Example 111 optionally includes sensing an indication of a measure of at least one of a renal or cardiac function.

In Example 113, the method of any one of Examples 111 or 112 optionally includes using information about the renal or cardiac function to adjust at least one of CCM energy, CCM delivery timing, CCM delivery location, or CCM electrode configuration.

In Example 114, the method of any one of Examples 111-113 optionally includes detecting an indication of a measure of at least one of: potassium, sodium, calcium, chloride, or bicarbonate.

In Example 115, the method of any one of Examples 111-114 optionally includes using information about the measure of the least one of potassium, sodium, calcium, chloride, or bicarbonate, to adjust at least one of CCM energy, CCM delivery timing, CCM delivery location, or CCM electrode configuration.

In Example 116, the method of any one of Examples 111-115 optionally includes detecting an indication of a measure of at least one of: blood urea nitrogen, serum creatinine, or glomerular filtration rate.

In Example 117, the method of any one of Examples 111-116 optionally includes using information about the measure of the at least one blood urea nitrogen, serum creatinine, or glomerular filtration rate, to adjust at least one of CCM energy, CCM delivery timing, CCM delivery location, or CCM electrode configuration.

In Example 118, the method of any one of Examples 111-117 optionally includes sensing a neural signal.

In Example 119, the method of any one of Examples 111-118 optionally includes using information about the neural signal to adjust at least one of CCM energy, CCM delivery timing, CCM delivery location, or CCM electrode configuration.

In Example 120, the method of any one of Examples 111-119 optionally includes sensing the neural signal includes sensing a neural signal from a vagal nerve; wherein the neural signal from the vagal nerve includes an indication of one of an increase or a decrease in vagal nerve activity.

In Example 121, the method of any one of Examples 111-120 optionally includes increasing at least one of CCM energy or frequency of CCM delivery when the neural signal indicates an increase in vagal nerve activity.

In Example 122, the method of any one of Examples 118-121 optionally includes monitoring at least one of sympathetic nerve activity or parasympathetic nerve activity; wherein the neural signal includes an indication of at least one of: an increase in sympathetic nerve activity, a decrease in sympathetic nerve activity, an increase in parasympathetic nerve activity, or a decrease in parasympathetic nerve activity.

In Example 123, the method of any one of Examples 118-122 optionally includes increasing at least one of CCM energy or frequency of CCM delivery when the neural signal indicates at least one of an increase in parasympathetic nerve activity or a decrease in sympathetic nerve activity.

In Example 124, the method of any one of Examples 118-123 optionally includes decreasing at least one of CCM energy or frequency of CCM delivery when the neural signal indicates at least one of an increase in sympathetic nerve activity or a decrease in parasympathetic nerve activity.

In Example 125, the method of any one of Examples 111-124 optionally includes delivering neural stimulation therapy.

In Example 126, the method of any one of Examples 111-125 optionally includes adjusting at least one of the CCM therapy or the neural stimulation therapy using information about the other of the CCM therapy or the neural stimulation therapy.

In Example 127, the method of any one of Examples 111-126 optionally includes adjusting at least one of the CCM therapy or the neural stimulation therapy using information about the sensed physiologic parameter.

Example 128 includes a method comprising: delivering a cardiac contractility modulation (CCM) therapy, wherein delivering the CCM therapy comprises delivering a non-stimulatory electrical energy during a refractory period of the heart; detecting an adverse event; and adjusting the CCM therapy using information about the adverse event.

In Example 129, the method of Example 128 optionally includes delivering a non-CCM therapy; wherein detecting an adverse event includes detecting a battery status; and wherein adjusting CCM therapy includes using battery status information to reconfigure which of multiple batteries services delivery of at least one of the non-CCM therapy or the CCM therapy.

In Example 130, the method of any one of Examples 128 or 129 optionally includes delivering a non-CCM therapy; wherein detecting an adverse event includes detecting a battery status; and wherein adjusting CCM therapy includes using battery status information to preferentially terminate delivery of one of the CCM therapy or the non-CCM therapy over the other of the CCM therapy or the non-CCM therapy.

In Example 131, the method of any one of Examples 128-130 optionally includes delivering neurostimulation therapy; detecting an adverse event associated with at least one of neurostimulation or CCM; and adjusting at least one of the CCM therapy or the neurostimulation therapy based on information about the adverse event associated with at least one of neurostimulation or CCM.

In Example 132, the method of any one of Examples 128-131 optionally includes doing one of the following when neurostimulation is enabled and an adverse event associated with the neurostimulation occurs: (a) turning off neural stimulation when CCM is enabled; (b) enabling CCM when CCM is not enabled and does not disabling neural stimulation; or (c) enabling CCM when CCM is not enabled and disabling neural stimulation.

In Example 133, the method of any one of Examples 128-132 optionally includes doing one of the following when CCM is enabled and an adverse event associated with the CCM occurs: (a) turning off CCM when neurostimulation is enabled; (b) turning on neurostimulation when neurostimulation is not enabled and not disabling CCM; or (c) enabling neurostimulation when neurostimulation is not enabled and disabling CCM.

In Example 134, the method of any one of Examples 128-133 optionally includes sensing a physiologic parameter.

In Example 135, the method of any one of Examples 128-134 optionally includes detecting pulsus alternans; wherein adjusting the CCM therapy includes adjusting at least one of CCM energy, CCM delivery timing, CCM delivery location, or CCM electrode configuration in response to the detection of pulsus alternans.

In Example 136, the method of Example 135 optionally includes increasing at least one of CCM energy or frequency of CCM delivery in response to the detection of pulsus alternans.

In Example 137, the method of any one of Examples 128-136 optionally includes providing information about the adverse event to a user interface configured to receive user-input information.

In Example 138, the method of any one of Examples 128-137 optionally includes detecting a CCM trigger condition for enabling CCM; wherein adjusting the CCM therapy includes enabling the CCM therapy when at least one CCM trigger is detected.

In Example 139, the method of any one of Examples 128-138 optionally includes the CCM trigger condition including at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

In Example 140, the method of any one of Examples 128-139 optionally includes the CCM trigger condition including an indication of worsening heart failure.

In Example 141, the method of any one of Examples 128-140 optionally includes the CCM trigger condition including an indication of an enabling or disabling of a device-based heart failure therapy other than CCM therapy.

In Example 142, the method of any one of Examples 128-141 optionally includes detecting a CCM stressor condition for disabling CCM; wherein adjusting the CCM therapy includes disabling the CCM therapy when at least one CCM stressor is detected.

In Example 143, the method of any one of Examples 128-142 optionally includes the CCM stressor condition including at least one of: a detection of sleep disordered breathing, a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

In Example 144, the method of any one of Examples 128-143 optionally includes the CCM stressor condition including an indication of enabling or disabling of a device-based heart failure therapy other than CCM therapy.

In Example 145, the method of any one of Examples 142-144 optionally includes the CCM stressor condition including a detected physical activity level that exceeds a specified threshold value.

In Example 146, the method of any one of Examples 128-145 optionally includes detecting: (1) a CCM trigger condition for enabling CCM, and (2) a CCM stressor condition for disabling CCM; wherein adjusting the CCM therapy includes enabling the CCM therapy when at least one CCM trigger is detected and disabling the CCM therapy when at least one CCM stressor is detected.

In Example 147, the method of any one of Examples 128-146 optionally includes the CCM trigger condition including at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

In Example 148, the method of any one of Examples 128-147 optionally includes the CCM trigger condition including an indication of worsening heart failure.

In Example 149, the method of any one of Examples 128-148 optionally includes the CCM trigger condition including an indication of an enabling or disabling of a device-based heart failure therapy other than CCM therapy.

In Example 150, the method of any one of Examples 128-149 optionally includes the CCM stressor condition including at least one of: a detection of sleep disordered breathing, a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

In Example 151, the method of any one of Examples 128-150 optionally includes the CCM stressor condition including an indication of enabling or disabling of a device-based heart failure therapy other than CCM therapy.

In Example 152, the method of any one of Example 128-151 optionally includes the CCM stressor condition including a detected physical activity level that exceeds a specified threshold value.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A shows an example of how the controller circuit can be configured to manage CCM therapy using a method that can be based at least in part on whether autothreshold or autocapture are also on.

FIG. 4 shows an example of portions of a method for managing CCM therapy in combination with a defibrillation/cardioversion shock.

FIG. 5A shows an example of portions of a method for managing CCM therapy in combination with ATP.

FIG. 5B shows an example of portions of a method for managing CCM therapy in combination with antitachyarrhythmia therapy, such as ATP or shock therapy.

DETAILED DESCRIPTION

Figure 1:
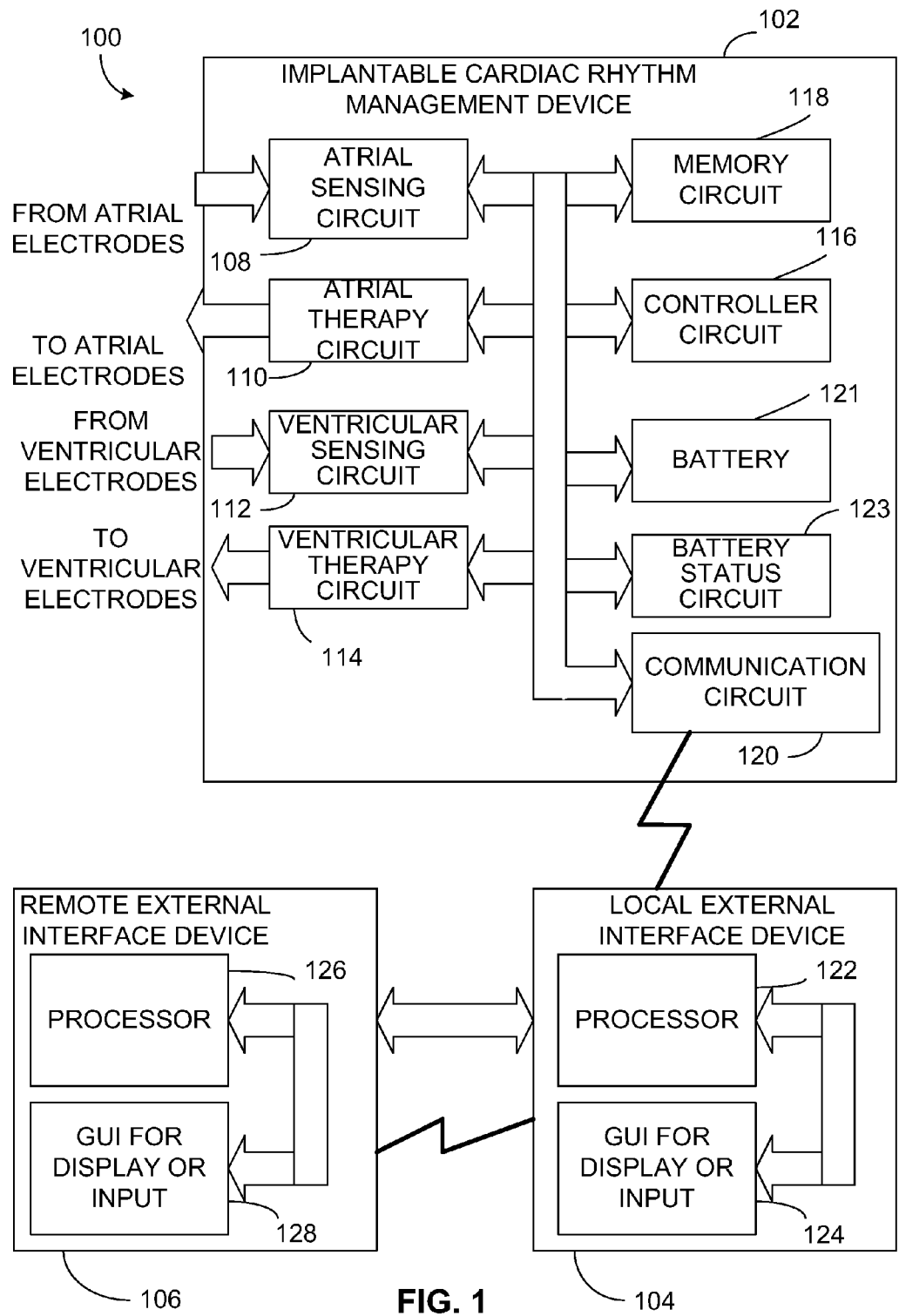
FIG. 1 illustrates an example of portions of a cardiac function management system and an environment in which it is used.

FIG. 1 illustrates an example of portions of a cardiac function management system 100 and an environment in which it is used. In certain examples, the system 100 includes an implantable cardiac rhythm or function management device 102, a local external interface device 104, and an optional remote external interface device 106. In certain examples, the implantable device 102 includes an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, and a battery status circuit 123.

The atrial sensing circuit 108 is typically coupled to electrodes, such as an intra-atrial electrode or any other electrode that permits sensing of an intrinsic atrial cardiac signal including atrial depolarization information. The atrial therapy circuit 110 is typically similarly coupled to these or other electrodes, such as for delivering pacing, cardiac resynchronization therapy (CRT), cardiac contractility modulation (CCM) therapy, defibrillation/cardioversion shocks, or other energy pulses to one or both atria.

The ventricular sensing circuit 112 is typically coupled to electrodes, such as an intra-ventricular electrode or any other electrode that permits sensing of an intrinsic ventricular cardiac signal including ventricular depolarization information. The ventricular therapy circuit 114 is typically similarly coupled to these or other electrodes, such as for delivering pacing, cardiac resynchronization therapy (CRT), cardiac contractility modulation (CCM) therapy, defibrillation/cardioversion shocks, or other energy pulses one or both ventricles.

A controller circuit 116 is coupled to the atrial sensing circuit 108 and the ventricular sensing circuit 112 to receive information from the sensed cardiac signals, and is coupled to the atrial therapy circuit 110 and the ventricular therapy circuit 114 to provide control or triggering signals to trigger timed delivery of the therapy pulses. In an example, the controller circuit 116 can be configured to provide control to help permit the CCM therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code configure the controller circuit 116.

A memory circuit 118 is coupled to the controller circuit 116, such as to store control parameter values, physiological data, or other information. A communication circuit 120 is coupled to the controller circuit 116 to permit radiofrequency (RF) or other wireless communication with an external device, such as the local external interface device 104 or the remote external interface device 106.

In an example, the battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 typically includes a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 typically includes a processor 126 and a graphic user interface (GUI) 128 or like device for displaying information or receiving user input as well as a communication circuit, such as to permit wired or wireless communication with the local external interface device 104 over the communications or computer network. Because the system 100 includes processing capability in the implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

1. Example of CCM Management Based on Battery Status

The present inventor has recognized, among other things, that CCM therapy, while potentially useful for enhancing heart contractility and, therefore, cardiac output, can involve power consumption that could potentially interfere with other even higher importance therapies being provided by the implantable device 102.

Figure 2A:
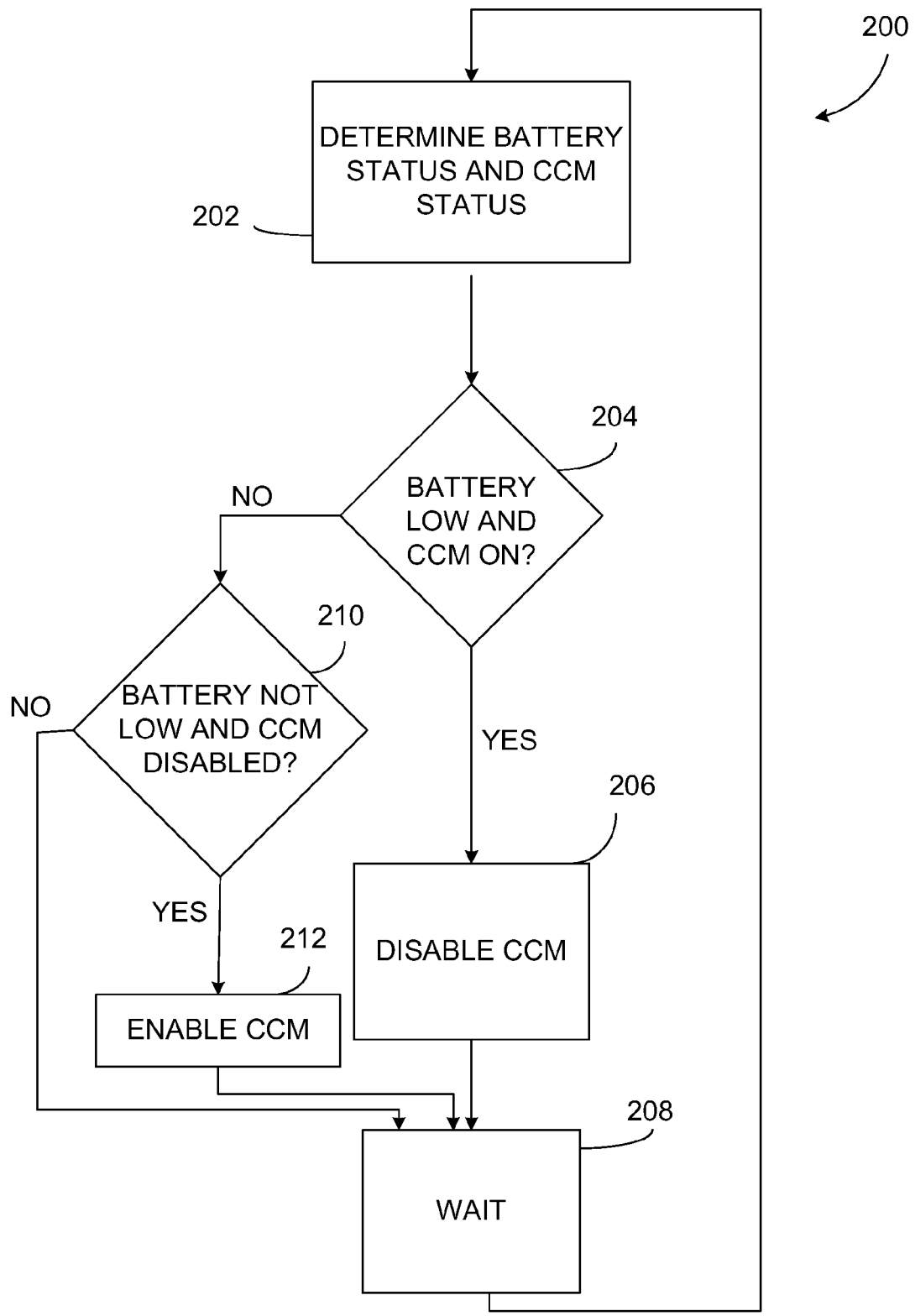
FIG. 2A shows an example of how the controller circuit can be configured to manage CCM therapy based at least in part on the battery status of the battery.

FIG. 2A shows an example of how the controller circuit 116 can be configured to manage CCM therapy based at least in part on the battery status of the battery 121, such as can be determined using the battery status circuit 123. In this example, the controller circuit 116 can be configured to perform a method 200, such as shown in the example of FIG. 2A.

At 202, the battery status and CCM status can be determined. In an example, determining the battery status can involve using the battery status circuit 123 to determine one or more characteristics of the battery 121 (e.g., battery terminal voltage, battery impedance, charge used, or charge remaining) from which the battery status can be inferred. In an example, inferring the battery status can also involve inferring one or more characteristics of the implantable device 102 (e.g., quiescent current or power consumption, transient current or power consumption, etc.). The measured battery status characteristic can be compared against one or more specified test conditions, and declared "Battery Low" if the battery fails to meet one or more specified test conditions. In an example, "Battery low" can be declared if an existing elective replacement indicator (ERI) is set.

In an example, CCM status can be determined by the controller circuit 116, such as by querying one or more control parameters indicating whether any form of CCM therapy (e.g., atrial CCM, ventricular CCM, bi-ventricular CCM, etc.) is currently turned on.

At 204, if Battery Low has been declared, and any CCM therapy is turned on, then at 206, the CCM therapy is temporarily disabled. At 208, a waiting period is allowed to elapse before process flow returns to 202. At 204, if Battery Low has not been declared or CCM is not on, then, in a first example, process flow can proceed directly to 208, or in a second example, process flow can proceed to 210.

At 210, if Battery Low has not been declared, and CCM is temporarily disabled (e.g., by a previous occurrence of 206), then at 212, the temporarily disabled CCM is re-enabled, and process flow can proceed to 208. Otherwise, at 210, process flow can proceed directly to 208 without performing 212.

In an example, at least a portion of the process shown in FIG. 2A can be automatically invoked just before a scheduled CCM therapy event, rather than using a fixed delay for the wait 208. For example, if a CCM pulse is scheduled to be delivered to the heart during a refractory period of the heart, then, before such delivery of the CCM pulse, the process 200 (e.g., excepting 208) can be performed to either allow the delivery of the CCM pulse to proceed, or to be inhibited by the temporary disabling of CCM therapy.

In an example, at least a portion of the process shown in FIG. 2A can be automatically invoked by a change in a battery status indicator, rather than using a fixed delay for the wait 208. For example, if the battery status changes to Battery Low, and a CCM therapy is on and not temporarily disabled, then the CCM therapy can be temporarily disabled. Upon a later change in the battery status indicator, the CCM can be re-enabled, such as when the battery condition has improved. For example, the battery condition can improve when the battery is rechargeable, and a recharging of the battery has occurred, or if other functionality of the implantable device 102 has been turned off, thereby allowing some recovery of the battery. In an example in which at least one other function can also be disabled upon a battery status indication such as Battery Low, the CCM and the at least one other function can be individually assigned a priority, such that a lesser importance (e.g., lower priority) function is disabled before a higher importance (e.g., higher priority) function, and a higher importance function is re-enabled before a lower importance function. In an example, defibrillation therapy and pacing therapy can be assigned a higher priority than CCM therapy.

Figure 2B:
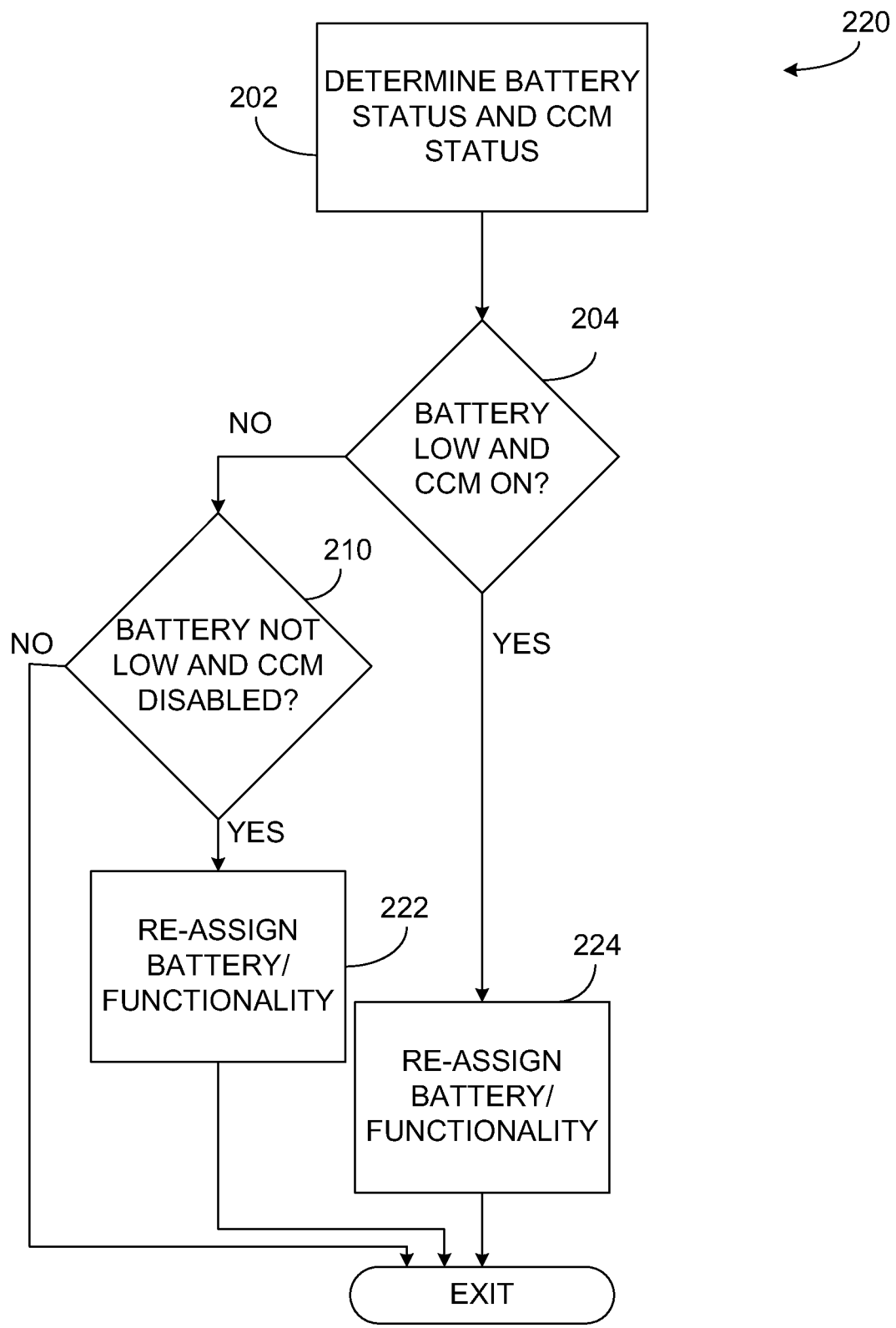
FIG. 2B shows an example of how the controller circuit can be configured to manage CCM therapy based at least in part on the battery status of the battery.

FIG. 2B shows an example of how the controller circuit 116 can be configured to manage CCM therapy based at least in part on the battery status of the battery 121, such as can be determined using the battery status circuit 123. In this example, the controller circuit 116 can be configured to perform a method 220, such as shown in the example of FIG. 2B. The method 220 is similar to the method 200 shown in FIG. 2A, except that, instead of disabling CCM at 206, and enabling CCM at 212, the controller circuit 216 can activate one or more switches to alter which of multiple batteries 121A, . . . , 121N are used to service which functionality.

For example, if the same battery 121 is being used to service both CCM therapy and a higher priority therapy (e.g., defibrillation, pacing, etc.), then at 224, the higher priority therapy can be switched to a dedicated battery 121 that is different from the battery providing energy for the CCM therapy and, at 222, battery sharing can optionally be resumed. In another example, at 224, CCM therapy can off-loaded from the shared battery 121 to a different battery 121.

Figure 2C:
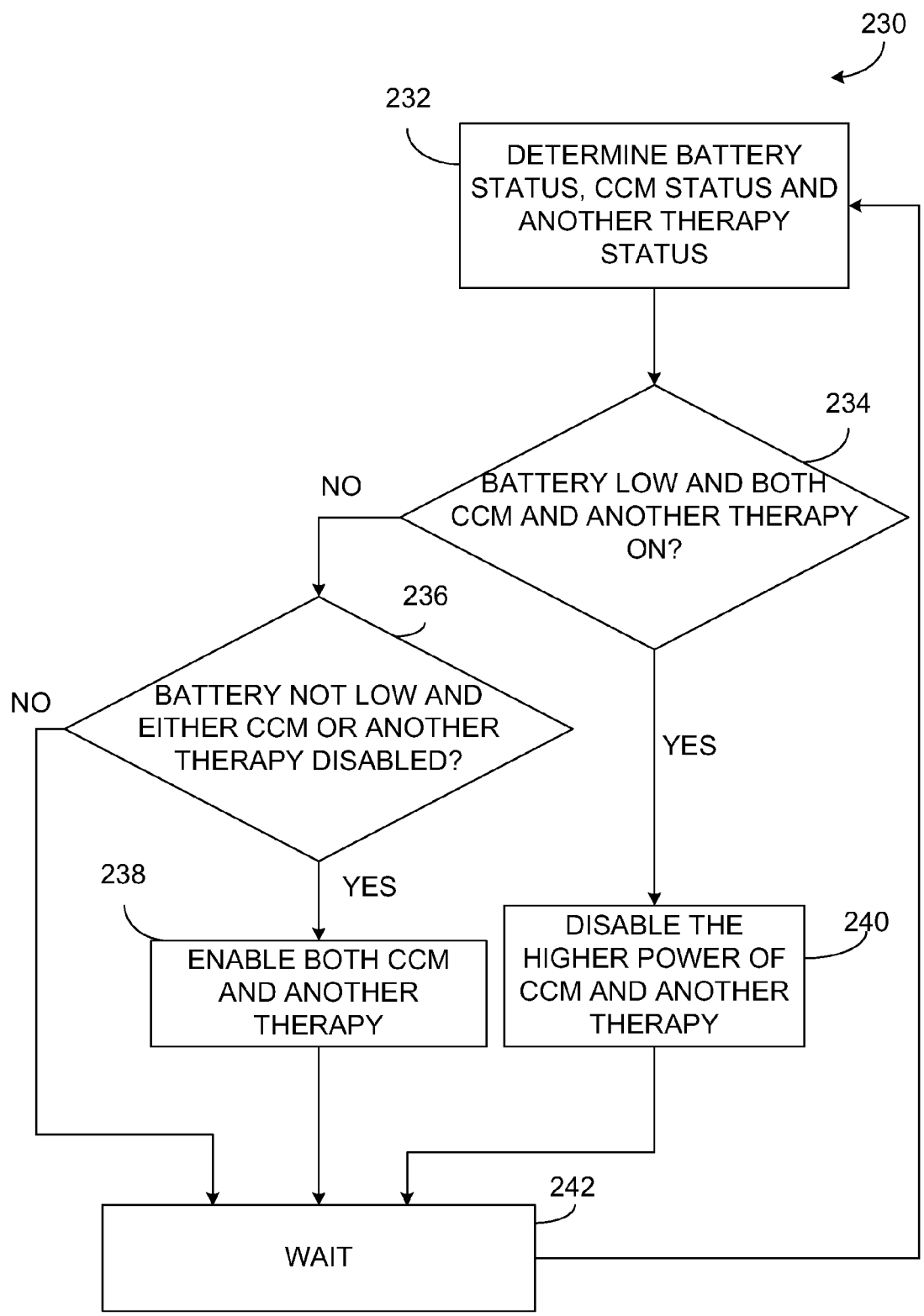
FIG. 2C shows an example of how the controller circuit can be configured to manage CCM therapy and another therapy based at least in part on the battery status of the battery.

FIG. 2C shows an example of how the controller circuit 116 can be configured to manage CCM therapy based at least in part on the battery status of the battery 121, such as can be determined using the battery status circuit 123. In this example, the controller circuit 116 can be configured to perform a method 230, such as shown in the example of FIG. 2C. At 232, the battery status, CCM status, and another therapy status can be determined. At 234, if Battery Low has been declared, and CCM therapy and another therapy (e.g. a non-CCM therapy) are turned on, then at 240, the higher power of CCM and another therapy is disabled. At 242, a waiting period is allowed to elapse before process flow returns to 232. At 234, if Battery Low has not been declared and CCM and another therapy are both not on, then, in a first example, process flow can proceed directly to 242, or in a second example, process flow can proceed to 236.

At 236 if Battery Low has not been declared, and either CCM or another therapy are temporarily disabled (e.g., by a previous occurrence of 240), then at 238, the temporarily disabled CCM or another therapy is re-enabled, and process flow can proceed to 242. Otherwise, at 236, process flow can proceed directly to 242 without performing 238.

In an example of the method 230, the other therapy can include another therapy that improves contractility, such as neurostimulation therapy.

2. Example of CCM Management with Auto-Threshold or Auto-Capture

The present inventor has recognized, among other things, that CCM therapy, while potentially useful for enhancing heart contractility and, therefore, cardiac output, could potentially interfere with an auto-threshold service or an auto-capture service also performed by the implantable device 102.

An auto-threshold service can involve determining a threshold energy level at which a pacing or CRT electrostimulation "captures" the heart by evoking a responsive heart contraction. This allows a physician or other individual to program one or more control parameters of the implantable device 102 to ensure that the electrostimulation energy exceeds the threshold value for capturing the heart. The auto-threshold determination can involve varying the electrostimulation energy (such as by adjusting electrostimulation pulse amplitude or duration) of electrostimulation pulses to determine the energy below which a resulting heart contraction is no longer evoked. Therefore, the autothreshold determination can involve issuing an electrostimulation pulse of a particular energy level, and then examining whether a responsive heart contraction has been evoked. In autocapture, electrostimulation energy can be automatically dynamically varied on an ongoing basis (e.g., rather than being programmed by a user to a fixed value) so as to generally maintain an electrostimulation energy that evokes responsive heart contractions, even if the capture threshold should change over time.

In an example, determining whether a responsive heart contraction has been evoked can involve using a sense amplifier, during a time period immediately following the issued electrostimulation pulse, to determine whether an intrinsic heart depolarization signal (e.g., a QRS complex, for a ventricular depolarization, or a P-wave, for an atrial depolarization) indicative of a heart contraction can be detected. Examples of evoked response sensing are described in U.S. Pat. Nos. 6,226,551, 6,427,085, and 5,941,903, each of which is incorporated by reference herein in its entirety, including its description of evoked response detection.

The present inventor has recognized that since the evoked response occurs during a post-electrostimulation refractory period of the heart, CCM therapy delivered during the same refractory period could potentially interfere with the auto-threshold or autocapture service's evoked response detection. For example, the CCM therapy pulse delivered could potentially be erroneously recognized by the sense amplifier as an evoked response, or it could potentially saturate the sense amplifier such as to render it inoperable for a period of time, or it could alter the threshold energy at which capture occurs.

Figure 3A:
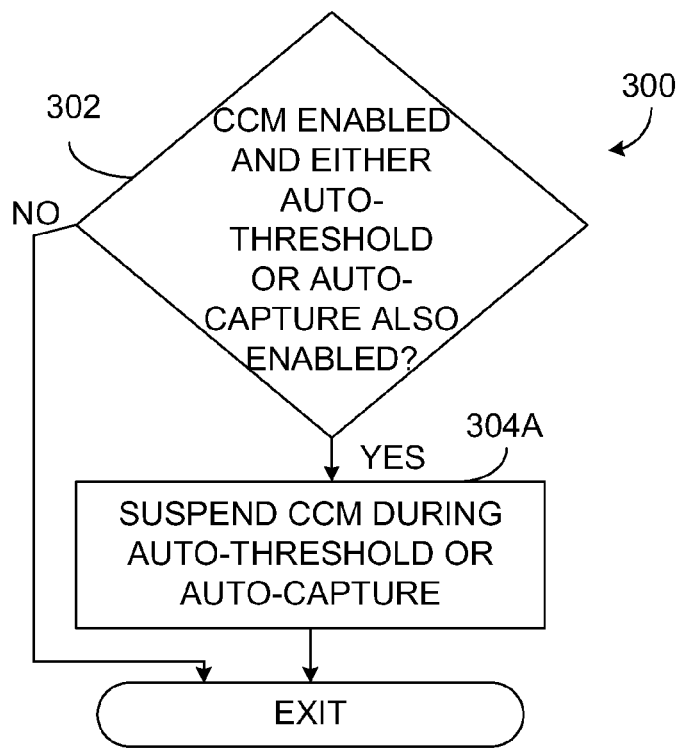

FIG. 3A shows an example of how the controller circuit 116 can be configured to manage CCM therapy using a method 300 that can be based at least in part on whether autothreshold or autocapture are also enabled. At 302, the controller circuit 116 can determine whether CCM therapy is enabled along with either of autothreshold or autocapture. If so, then at 304A, CCM can be suspended during the auto-threshold or autocapture. In an example, this can include suspending CCM during the evoked response testing of the autothreshold or autocapture services. In another example, this can include suspending CCM until the autothreshold service has completed all of its series of evoked response tests.

Figure 3B:
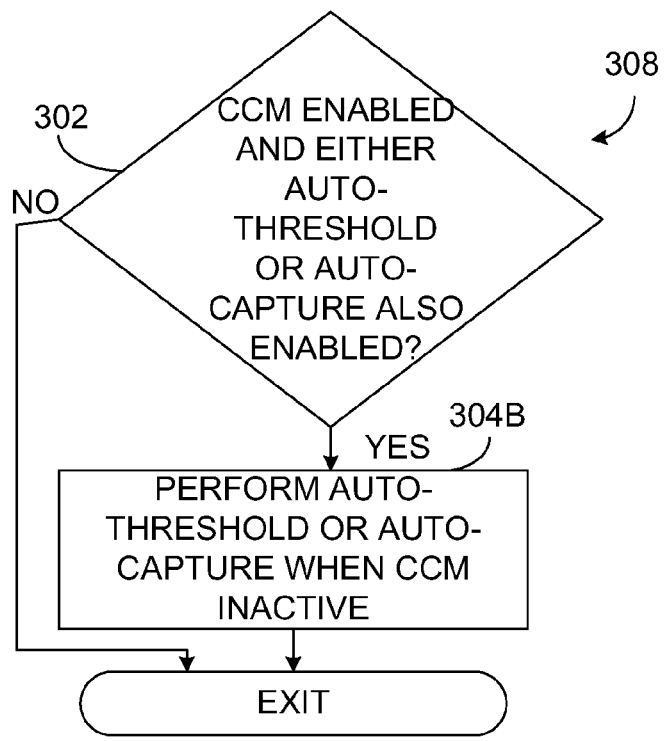
FIG. 3B shows an example of a method of using CCM and evoked response testing.

FIG. 3B shows an example of a method 308 of using CCM and evoked response testing. At 302, the controller circuit 116 can determine whether CCM therapy is enabled along with either of autothreshold or autocapture. If so, then at 304B, the evoked response testing of the autothreshold or autocapture function can be performed during time periods during which the CCM therapy is suspended (e.g., no CCM therapy energy is being applied to the heart). Although enabled by the healthcare provider, CCM can be autonomously suspended by controller circuit 116 at regular intervals. For example, CCM can be suspended for 21 hours out of every 24 hours. In addition, CCM can be suspended during cardiac arrhythmias. For example, CCM can be suspended during arrhythmic cardiac cycles that include atrial or ventricular ectopy (e.g., a premature ventricular contraction), atrial or ventricular tachycardia, sinus bradycardia, or atrial or ventricular pacing.

Figure 3C:
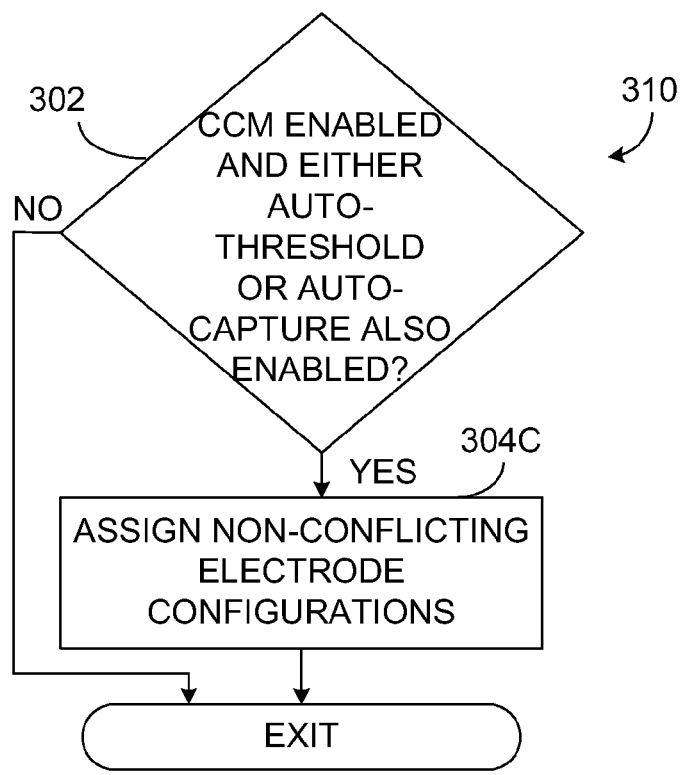
FIG. 3C shows an example of a method of using CCM and autothreshold or autocapture.

FIG. 3C shows an example of a method 310 of using CCM and autothreshold or autocapture. At 302, the controller circuit 116 can determine whether CCM therapy is on along with either of autothreshold or autocapture. If so, then at 304C, non-conflicting electrode configurations are assigned to the CCM therapy and to the one or both of the autothreshold or autocapture therapy that is also on, such that the CCM energy delivery to the heart does not interfere with the evoked response testing of the one or both of the autothreshold or autocapture services.

In an example, non-conflicting electrodes can sense a ventricular evoked response using a pair of electrodes located on or within a contralateral chamber of the heart to that of CCM therapy delivery. In an example, an evoked response can be sensed using a pair of electrodes that are not being used for delivery of CCM therapy on or within the same chamber of the heart. In an example, an evoked response can be sensed using an electrode not used for delivery of CCM therapy on or within the same or contralateral chamber of the heart, in conjunction with another electrode in a non-cardiac location (e.g., the housing of the implantable cardiac rhythm/function management device 102).

Figure 3D:
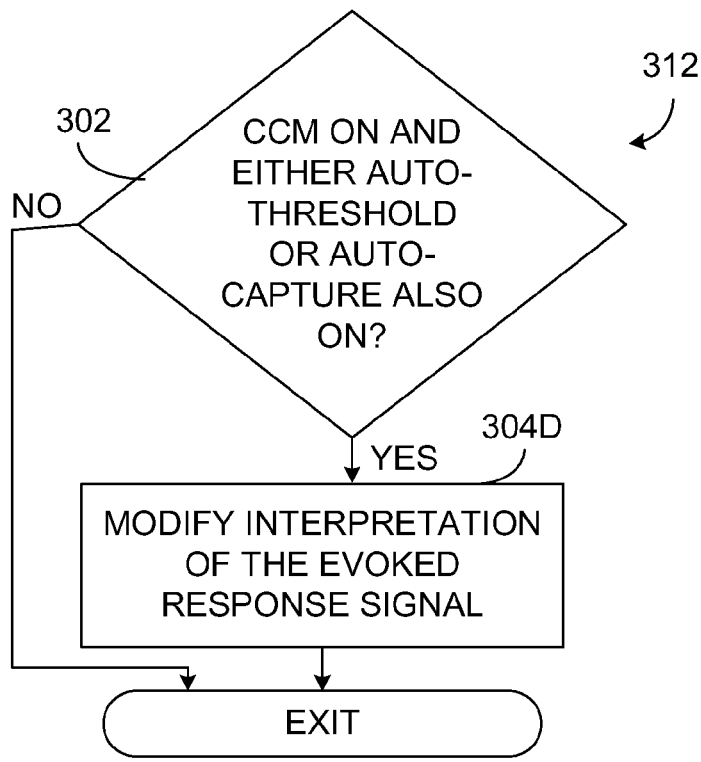
FIG. 3D shows an example of a method indicating how autothreshold or autocapture can accommodate CCM therapy.

FIG. 3D shows an example of a method 312 indicating how autothreshold or autocapture can accommodate CCM therapy. At 302, the controller circuit 116 can determine whether CCM therapy is enabled, along with either of autothreshold or autocapture. If so, then, at 304D, interpretation of the evoked response signal used for autothreshold or autocapture can be modified to accommodate any alteration in the evoked response signal caused by CCM therapy. Examples of evoked response parameters that can be accommodated include one or more of magnitude, timing, total energy, or signal morphology. For example, if CCM therapy increases the peak amplitude of the evoked response caused by capture of a pacing pulse, an autothreshold or autocapture can increase the amplitude of the evoked response expected from a capture of a pacing pulse.

Figure 3E:
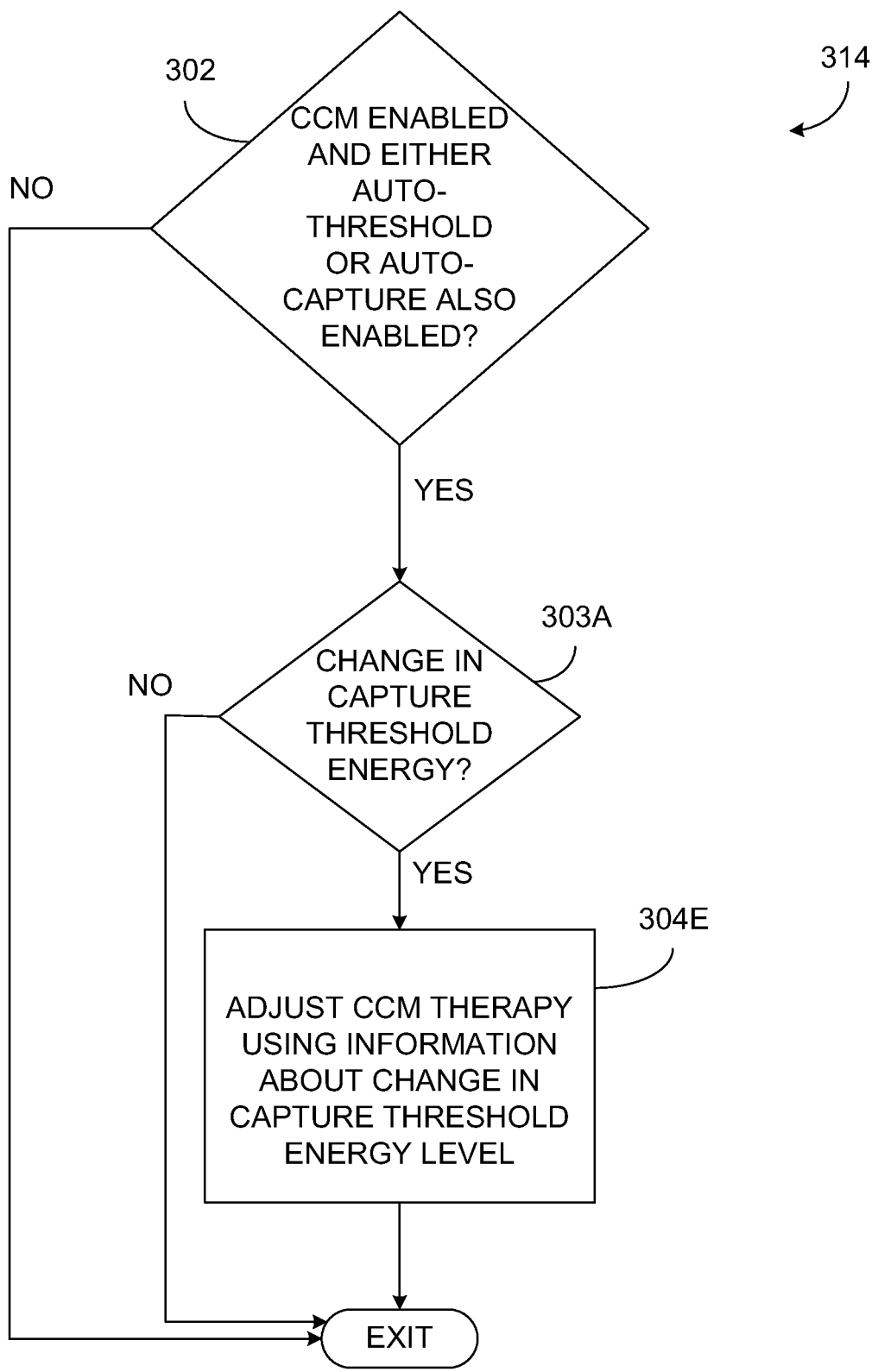
FIG. 3E shows an example of a method of adjusting CCM therapy using information about a change in capture threshold energy.
Figure 3F:
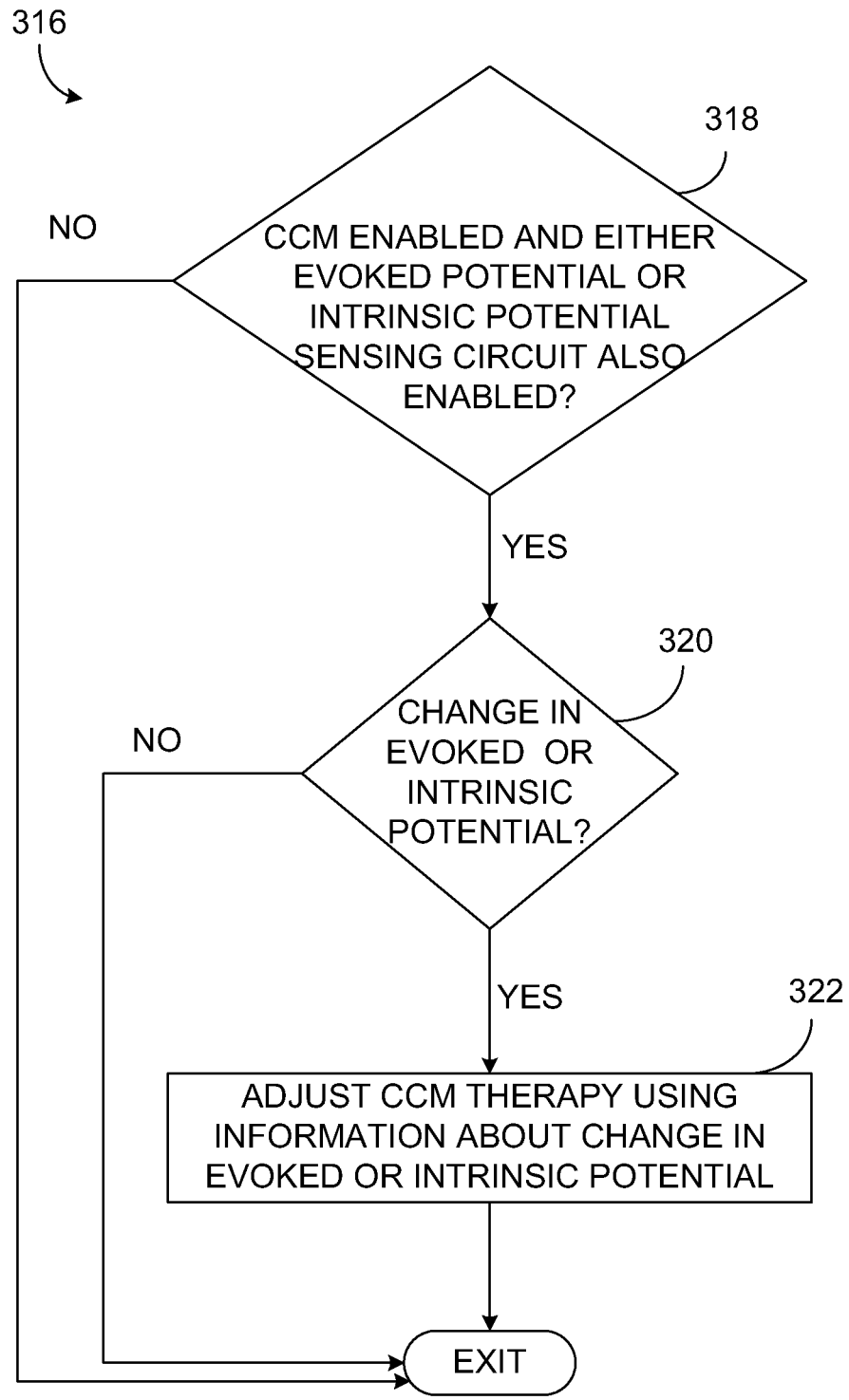
FIG. 3F shows an example of a method of adjusting CCM therapy using information about a change in an evoked or intrinsic potential.

In addition to recognizing that CCM therapy could potentially affect or interfere with auto-threshold or auto-capture service, the present inventor has recognized, among other things, that changes in capture threshold or evoked or intrinsic potentials can be used to monitor CCM therapy effectiveness. FIGS. 3E and 3F illustrate some examples.

FIG. 3E shows an example of a method 314 of adjusting CCM therapy using information about a change in capture threshold energy. At 302, the controller circuit 116 can determine whether CCM therapy is enabled, along with either of autothreshold or autocapture. If so, then, at 303A, the controller circuit 116 can detect whether there is a change in the electrostimulation capture threshold energy level. If so, then, at 304E, the controller circuit 116 can adjust CCM therapy using information about the change in the electrostimulation capture threshold energy level. For example, it is believed that an increase in capture threshold energy may indicate worsening global cardiac function, worsening myocyte function, or cardiac remodeling. In this case, CCM therapy can be adjusted, such as to increase its effectiveness in treating or counteracting a worsening cardiac condition. An example of how CCM therapy can be adjusted under these conditions includes increasing the energy or frequency of CCM delivery. Other examples of how CCM therapy can be adjusted include changing a configuration of electrodes used for CCM delivery or adjusting the timing of CCM delivery within the refractory period.

FIG. 3F shows an example of a method 316 of adjusting CCM therapy using information about a change in an evoked or intrinsic potential. In this example, an evoked potential can be a ventricular potential resulting from a pacing pulse, and an intrinsic potential can be a ventricular potential resulting from the heart's own electrical activity. A ventricular potential can be any potential caused by depolarization or repolarization of one or both ventricles. At 318, the controller circuit 116 can determine whether CCM therapy is enabled, together with either of an evoked potential sensing circuit or an intrinsic potential sensing circuit also being enabled. If so, then, at 320, the controller circuit 116 can detect whether there is a change in the evoked or intrinsic potential. Changes in evoked or intrinsic potential can include changes in magnitude, frequency, or morphology, for example. If there is a change in evoked or intrinsic potential, then, at 322, the controller circuit 116 can adjust CCM therapy using information about the change in the evoked or intrinsic potential. For example, it is believed that a decrease in an evoked or intrinsic potential magnitude or an increase in an evoked or intrinsic potential frequency may indicate worsening global cardiac function, worsening myocyte function, or cardiac remodeling. In this case, CCM therapy can be adjusted, such as to increase its effectiveness in treating or counteracting a worsening cardiac condition. An example of how CCM therapy can be adjusted under these conditions includes increasing the energy or frequency of CCM delivery. Other examples of how CCM therapy can be adjusted can include changing a configuration of electrodes used for CCM delivery or adjusting the timing of CCM delivery within the refractory period.

3. Example of CCM Management with Defibrillation Shocks

The present inventor has recognized, among other things, that CCM therapy delivery circuits, such as can be included in the ventricular therapy circuit 114 or the atrial therapy circuit 110, or intrinsic heart signal sensing circuits, such as for timing the delivery of CCM therapy, such as can be included in the atrial sensing circuit 108 or the ventricular sensing circuit 112, could potentially be adversely affected by the delivery of an atrial or ventricular defibrillation/cardioversion shock.

FIG. 4 shows an example of portions of a method 400 for managing CCM therapy in combination with a defibrillation/cardioversion shock. At 402, the controller circuit 116 determines that it has scheduled delivery of an atrial or ventricular defibrillation or cardioversion shock. If so, then at 404, the CCM therapy delivery circuits, such as can be included in the ventricular therapy circuit 114 or the atrial therapy circuit 110, can be isolated from the electrodes that would be otherwise used for providing CCM therapy or for sensing an intrinsic electrical heart such as for timing the delivery of CCM therapy.

In an example, isolating a CCM therapy delivery circuit from an electrode that could be subjected to the presence of significant energy during the shock can include opening a switch between the CCM therapy delivery circuit (or CCM intrinsic heart signal sensing circuit) and the electrode.

In an example, isolating the CCM therapy delivery or CCM sensing circuit from a corresponding electrode comprises providing a silicon-controlled rectifier (SCR) or a zener diode for automatically responding to the shock by turning on such a device to re-route shock energy away from the CCM therapy delivery or CCM sensing circuit.

4. Example of CCM Management with Antitachyarrhythmia Therapy

The present inventor has recognized, among other things, that CCM therapy could potentially adversely interact with antitachyarrhythmia therapy, such as for interrupting a tachyarrhythmia. Antitachyarrhythmia therapy can include antitachyarrhythmia pacing (ATP), or cardioversion or defibrillation shock therapy, for example.

As described above, ATP can include delivering a quick sequence of carefully timed electrostimulations, such as to "overdrive" a too-fast tachyarrhythmic heart rhythm so that the ATP pulses take control of the heart rhythm; then the ATP pulse rate can be lowered to an appropriate heart rate. Cardioversion or defibrillation shock therapy can include delivering a higher-energy shock to interrupt an abnormal heart rhythm, such as a tachyarrhythmia. The timing of energy delivery to the heart during ATP or shock therapy can be important to tachyarrhythmia termination, therefore, CCM energy delivery could possibly interfere with such antitachyarrhythmia therapies. Since ATP or shock therapy is delivered to interrupt a tachyarrhythmia, it can be regarded as more important than contractility enhancement via CCM.

FIG. 5A shows an example of portions of a method 500 for managing CCM therapy in combination with ATP. At 502, if ATP is scheduled or in progress, then at 504, CCM is temporarily disabled until the ATP is complete or, alternatively, until the ATP is complete and the tachyarrhythmia is declared terminated.

FIG. 5B shows an example of portions of a method 508 for managing CCM therapy in combination with antitachyarrhythmia therapy, such as ATP or shock therapy. At 510, if a tachyarrhythmia is detected or otherwise declared present, then at 512, CCM is temporarily disabled until the tachyarrhythmia is declared no longer present. In an example, the method 508 is specific to ventricular tachyarrhythmia being declared present. In another example, the method 508 is applied if either atrial or ventricular tachyarrhythmia is declared present. In another example, at 512, CCM can be inhibited until an antitachyarrhythmia therapy (e.g., ATP or shock) has been delivered, then CCM can be resumed.

5. Example of CCM Management with Other Pulses

The present inventor has recognized, among other things, that CCM therapy pulses being delivered to the heart could potentially adversely interact with a variety of other pulses being delivered to the heart or to one or more other locations within or on the surface of the body. Some examples such other pulses can include, by way of example, but not by way of limitation, one or more of: (1) a bradycardia pacing pulse, ATP pulse, or CRT pulse; (2) a "recharge" pulse, delivered after a pacing pulse to restore charge equilibrium or to discharge a coupling capacitor; (3) an impedance sensing pulse (e.g., a test current delivered for sensing a responsive voltage for determining a thoracic impedance, intracardiac impedance, or other sensed impedance of interest); (4) a vagal or other neural stimulation pulse, such as can be delivered to influence autonomic balance between the sympathetic and parasympathetic components of the nervous system; or (5) an atrial or ventricular defibrillation or cardioversion shock pulse.

Figure 6:
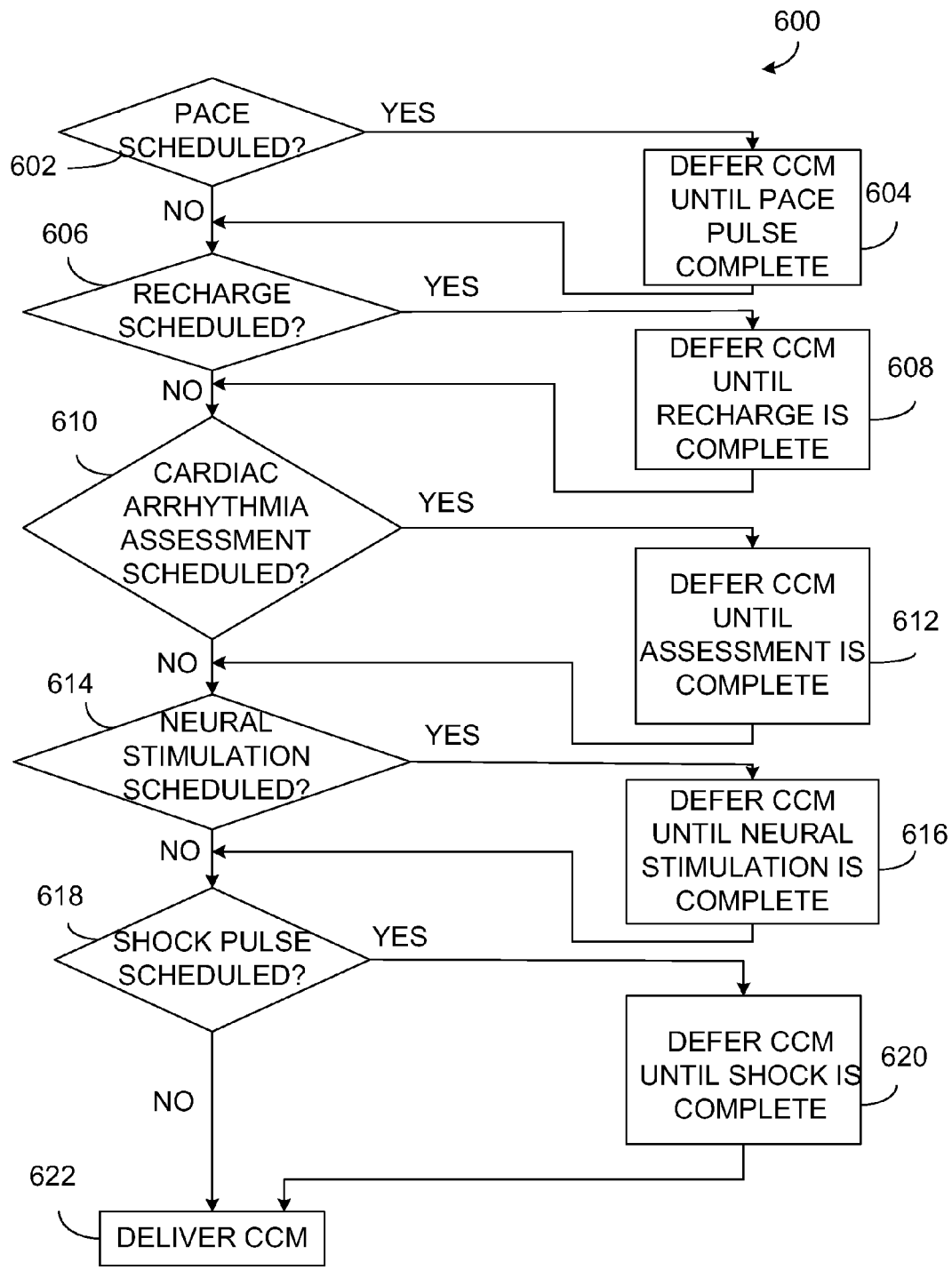
FIG. 6 shows an example of portions of a method for avoiding unwanted interactions between CCM and such other pulses or functionalities.

FIG. 6 shows an example of portions of a method 600 for avoiding unwanted interactions between CCM and such other pulses or functionalities.

At 602, if a pace pulse (e.g., bradycardia pacing pulse, ATP pulse, or CRT pulse) is scheduled, then at 604, CCM pulse delivery is rescheduled until after delivery of the pace pulse will be completed, before process flow resumes at 606. Otherwise, at 604, if no pace pulse is scheduled, then process flow continues at 606.

At 606, if a recharge pulse is scheduled, then at 608, CCM pulse delivery is rescheduled until after delivery of the recharge pulse will be completed, before process flow continues at 610. Otherwise, at 606, if no recharge pulse is scheduled, then process flow continues at 610.

At 610, if cardiac arrhythmia assessment (e.g., impedance sensing) is scheduled, then at 612, CCM pulse delivery is rescheduled until after the arrhythmia assessment will be completed, before process flow continues at 614. Otherwise, at 610, if no such arrhythmia assessment is scheduled, then process flow continues at 614. In an example, the check for scheduled arrhythmia assessment at 610 is applied not just to impedance sensing (e.g., thoracic impedance, or intracardiac impedance), but is optionally also applied to one or more other forms of arrhythmia assessment (e.g., intrinsic heart signal sensing).

At 614, if a neural stimulation pulse is scheduled, then at 616, CCM pulse delivery is rescheduled until after the neural stimulation will be completed, before process flow continues at 618. Otherwise, at 614, if no such neural stimulation pulse is scheduled, then process flow continues at 618.

At 618, if a shock pulse is scheduled, then at 620, CCM pulse delivery is rescheduled until after the shock delivery will be completed, before process flow continues at 622. Otherwise, at 618, if no shock delivery is scheduled, then process flow continues at 622.

At 622, after any scheduled pace, recharge, sensing, neural stimulation, or shock has been delivered, a scheduled or rescheduled CCM therapy pulse can be delivered.

In further variations, checking for other pulse delivery can be similarly incorporated into the method 600 shown in FIG. 6.

In another example, instead of rescheduling CCM pulse delivery to defer CCM until after completion of any scheduled pace, recharge, arrhythmia assessment, neural stimulation, or shock, the one or more of any scheduled pace, recharge, arrhythmia assessment, neural stimulation, or shock can be rescheduled until after CCM delivery will be completed.

6. Example of CCM Management with Defibrillation Threshold

The present inventor has recognized, among other things, that CCM therapy pulses being delivered to the heart could potentially impact atrial or ventricular defibrillation thresholds, the minimum shock energy needed to interrupt a tachyarrhythmia. The actual defibrillation shock energy can generally be programmed to a value that exceeds the corresponding defibrillation threshold energy.

The defibrillation threshold energy can be determined by performing a defibrillation threshold test. In an example, the defibrillation threshold test can include actually delivering a shock during a tachyarrhythmia, for example, such as can be induced by a physician under controlled conditions. In another example, the defibrillation threshold test can estimate the defibrillation threshold by delivering a smaller test energy, rather than delivering an actual defibrillation shock. In either case, the determined defibrillation threshold energy could be affected by whether CCM therapy is being delivered to the subject during or around the time that the defibrillation threshold test is being performed.

Figure 7:
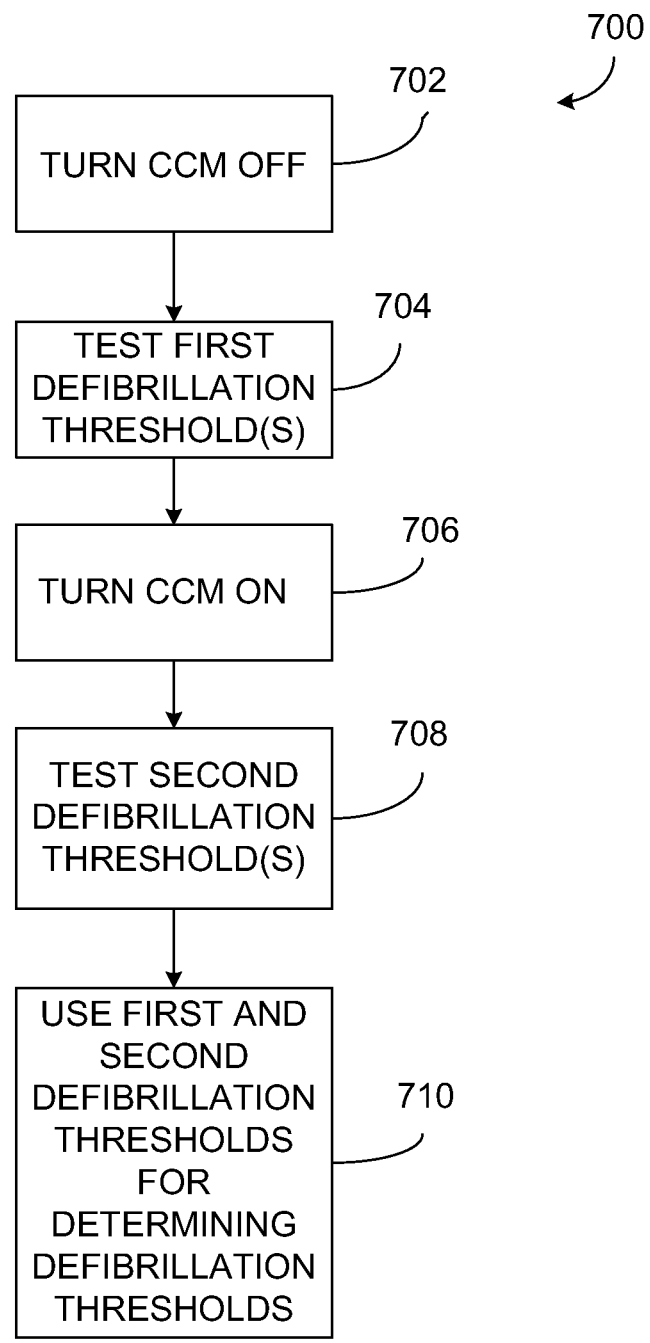
FIG. 7 shows an example of portions of a method for defibrillation threshold testing that can take into account whether CCM therapy is being delivered.

FIG. 7 shows an example of portions of a method 700 for defibrillation threshold testing that can take into account whether CCM therapy is being delivered. At 702, CCM therapy is turned off, if not off already. At 704, defibrillation threshold testing is performed. This can involve performing atrial or ventricular defibrillation testing, or both, as desired, to obtain first defibrillation threshold(s) under a condition of no CCM. This can also involve performing defibrillation testing using one or more different electrode combinations, such as those involving the housing of the implantable cardiac rhythm/function management device 102, a proximal coil electrode 1712 to the implantable cardiac rhythm/function management device, and a distal coil electrode 1710 to the implantable cardiac rhythm/function management device. At 706, CCM therapy is turned on to its programmed CCM parameter settings (or, alternatively to default CCM parameter settings). At 708, defibrillation threshold testing is again performed. This can involve performing atrial or ventricular defibrillation testing, or both, as desired, to obtain second defibrillation threshold(s) under a condition of CCM. At 710, the determined first and second defibrillation threshold(s) are used for determining defibrillation thresholds. In an example, this can include establishing separate defibrillation thresholds for CCM and non-CCM conditions (for respective use under such different corresponding conditions) such as respectively determined by the second defibrillation threshold(s) and the first defibrillation threshold(s). In another example, this can include establishing a conservative defibrillation threshold that selects the higher energy defibrillation threshold from the data obtained under CCM and non-CCM conditions.

In a variation of the technique described, defibrillation threshold testing can be repeated under different CCM conditions (varying CCM parameters). This information can be used for selecting a defibrillation threshold for use under CCM conditions that most closely match those under which the CCM threshold was determined, or for selecting a worst-case defibrillation threshold so that the defibrillation shock energy can be adjusted to accordingly exceed the worst-case defibrillation threshold energy.

In another variation of the technique described, the higher energy of the CCM and non-CCM defibrillation thresholds is used to select the delivered defibrillation energy for defibrillations that are scheduled to occur within a specified time (e.g., 5 minutes) after CCM conditions have ceased. Thus, in an example, if a tachyarrhythmia occurs such that a defibrillation shock is scheduled to be delivered within the specified time (e.g., at 4 minutes) after CCM therapy has been turned off, the higher energy of the CCM and non-CCM defibrillation thresholds is used for determining defibrillation energies. In a further variation, the CCM value of the defibrillation threshold is used for a defibrillation shock to be delivered within the specified time after CCM conditions have ceased.

7. Example of CCM Management with Pacing/CRT Threshold

The present inventor has recognized, among other things, that CCM therapy pulses being delivered to the heart could potentially impact atrial or ventricular pacing or CRT thresholds, the minimum electrostimulation energy needed to evoke a responsive heart contraction. The actual pacing or CRT energy can generally be programmed to a value that exceeds the corresponding pacing or CRT threshold energy.

The pacing or CRT threshold energy can be determined by performing a pacing or CRT threshold test. In an example, the pacing or CRT threshold test can include actually delivering pacing or CRT pulses of varying energy levels and determining which energies obtain a responsive evoked heart contraction. The determined pacing or CRT threshold energy could be affected by whether CCM therapy is being delivered to the subject during or around the time that the pacing or CRT threshold test is being performed.

Figure 8:
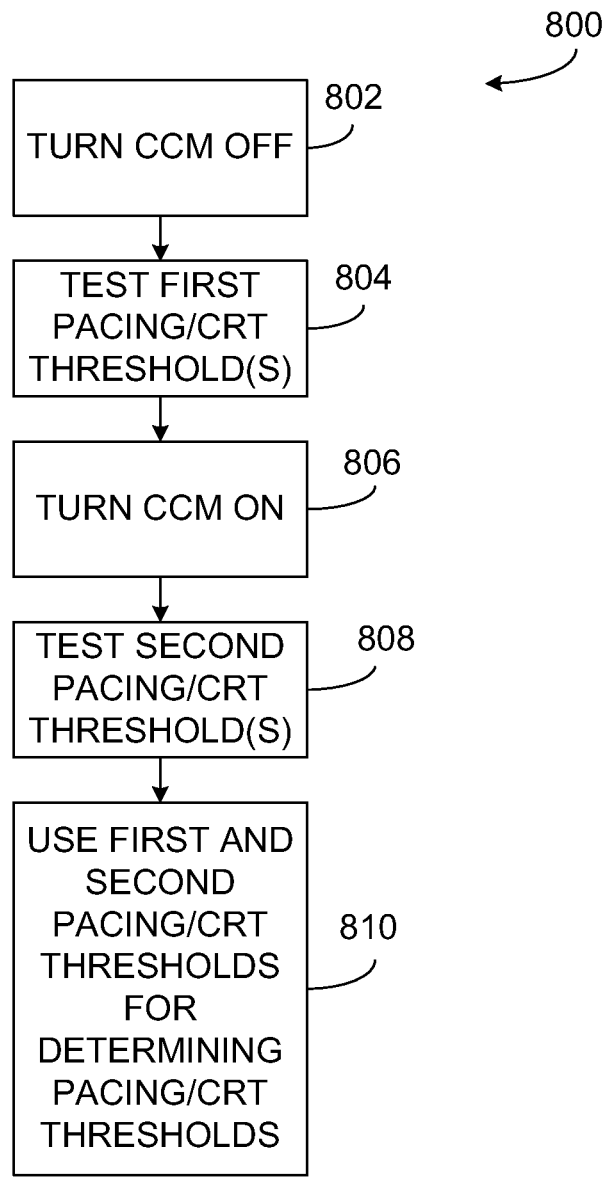
FIG. 8 shows an example of portions of a method for pacing or CRT threshold testing that can take into account whether CCM therapy is being delivered.

FIG. 8 shows an example of portions of a method 800 for pacing or CRT threshold testing that can take into account whether CCM therapy is being delivered. At 802, CCM therapy is turned off, if not off already. At 804, pacing or CRT threshold testing is performed. This can involve performing atrial, ventricular, bi-atrial, bi-ventricular, intra-atrial, or intraventricular electrostimulation threshold testing, as desired, to obtain first pacing or CRT threshold(s) under a condition of no CCM. This can also involve performing electrostimulation threshold testing using one or more different electrode configurations, such as one or more bipolar or unipolar electrode configurations. At 806, CCM therapy is turned on to its programmed CCM parameter settings (or, alternatively to default CCM parameter settings). At 808, pacing or CRT threshold testing is again performed. This can involve performing atrial or ventricular pacing or CRT testing, or both, as desired, to obtain second pacing or CRT threshold(s) under a condition of CCM. At 810, the determined first and second pacing or CRT threshold(s) are used for determining pacing or CRT thresholds. In an example, this can include establishing separate pacing or CRT thresholds for CCM and non-CCM conditions (for respective use under such different corresponding conditions) such as respectively determined by the second pacing or CRT threshold(s) and the first pacing or CRT threshold(s). In another example, this can include establishing a conservative pacing or CRT threshold that selects the higher energy pacing or CRT threshold from the data obtained under CCM and non-CCM conditions.

In a variation of the technique described, pacing or CRT threshold testing can be repeated under different CCM conditions (varying CCM parameters). This information can be used for selecting a pacing or CRT threshold for use under CCM conditions that most closely match those under which the CCM threshold was determined, or for selecting a worst-case pacing or CRT threshold so that the pacing or CRT electrostimulation energy can be adjusted to accordingly exceed the worst-case pacing or CRT threshold energy.

In another variation of the technique described, the higher energy of the CCM and non-CCM pacing or CRT thresholds is used to select the delivered pacing or CRT energy for pacing or CRT electrostimulations that are scheduled to occur within a specified time (e.g., 5 minutes) after CCM conditions have ceased. Thus, in an example, if a tachyarrhythmia occurs such that a pacing or CRT electrostimulation is scheduled to be delivered within the specified time (e.g., at 4 minutes) after CCM therapy has been turned off, the higher energy of the CCM and non-CCM pacing or CRT thresholds is used for determining pacing or CRT electrostimulation energies. In a further variation, the CCM value of the pacing or CRT threshold is used for a pacing or CRT electrostimulation to be delivered within the specified time after CCM conditions have ceased.

Figure 9:
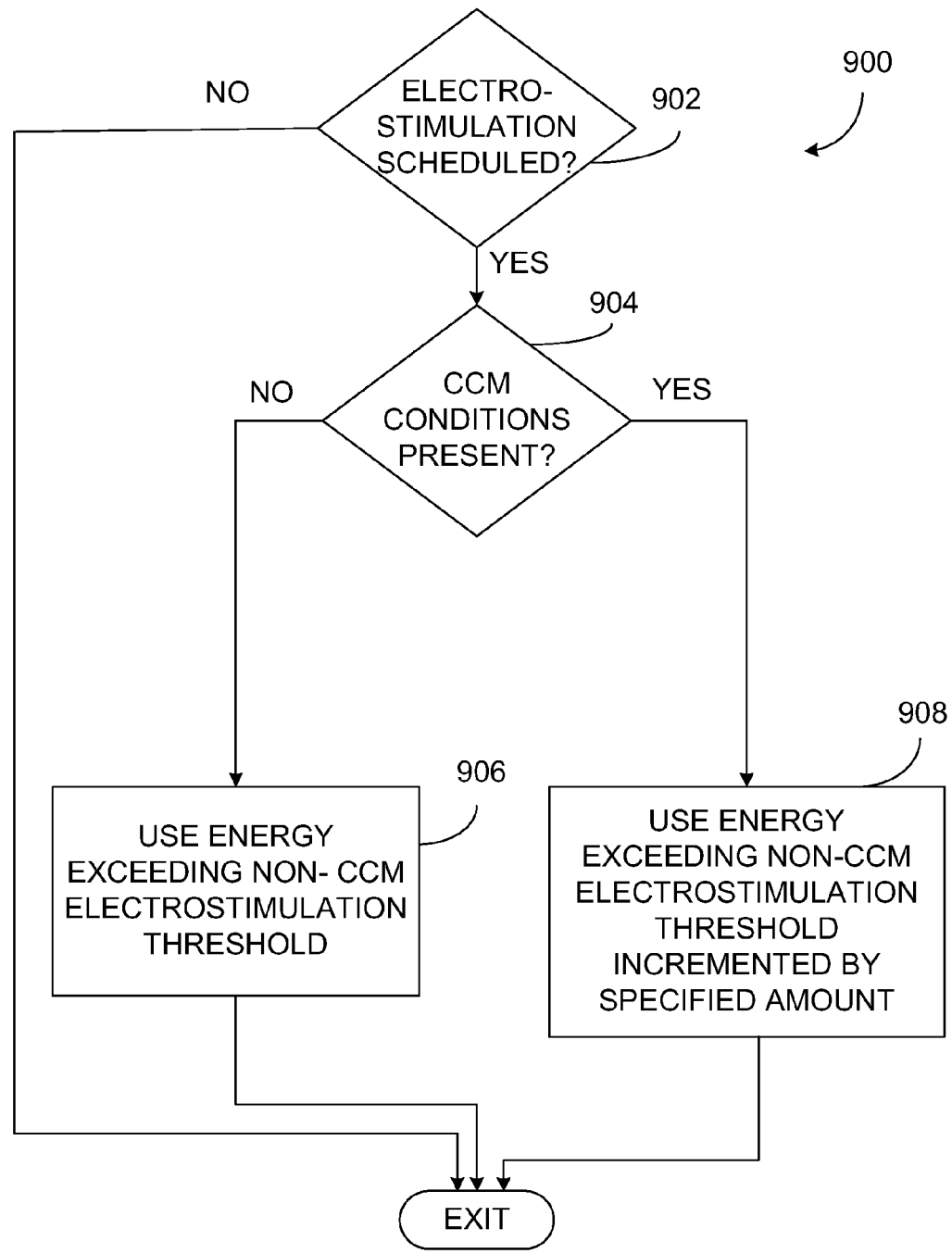
FIG. 9 shows an example of portions of a method for adjusting pacing or CRT electrostimulation energy depending on whether CCM conditions are present.

FIG. 9 shows an example of portions of a method 900 for adjusting pacing or CRT electrostimulation energy depending on whether CCM conditions are present. At 902, if a pacing or CRT electrostimulation is scheduled, then, at 904, it is determined whether CCM conditions are present. In an example, CCM conditions are deemed present if CCM is on. In a variation, CCM conditions are also deemed present if CCM has been on within a specified preceding time period (e.g., 5 minutes). At 904, if CCM conditions are not present, then, at 906, the electrostimulation can be delivered using an energy exceeding an electrostimulation threshold value that was previously determined under non-CCM conditions. At 904, if CCM conditions are present, then, at 908, the electrostimulation can be delivered using an energy exceeding the non-CCM electrostimulation threshold value incremented by a specified amplitude or duration amount (e.g., incremented by 1 Volt). This can help ensure capture if CCM conditions are present, such as if CCM is on or has recently been on.

8. Example of CCM Shared Circuitry with Pacing or CRT

The present inventor has recognized, among other things, that in certain examples, it can be desirable to share at least some of the same circuitry for generating and delivering CCM energy as is used for generating and delivering pacing or CRT electrostimulations, but that doing so could result in unwanted interactions. For example, where CCM uses the same coupling capacitor as pacing or CRT (as explained below), residual charge left on the coupling capacitor by CCM could potentially inhibit a pacing or CRT electrostimulation pulse from capturing the heart (e.g., evoking a responsive heart contraction).

An illustrative example of pacing output channels that can be adapted to also be used for providing CCM is described in Michael J. Lyden et al. U.S. Provisional Patent Application Ser. No. 61/009,747, now expired, filed on Dec. 30, 2007, entitled CONFIGURATION OF PACING OUTPUT CHANNELS, which is assigned to Cardiac Pacemakers, Inc., and which is incorporated by reference herein in its entirety, including its description of pacing output channels, their configuration, and methods of use.

Figure 10:
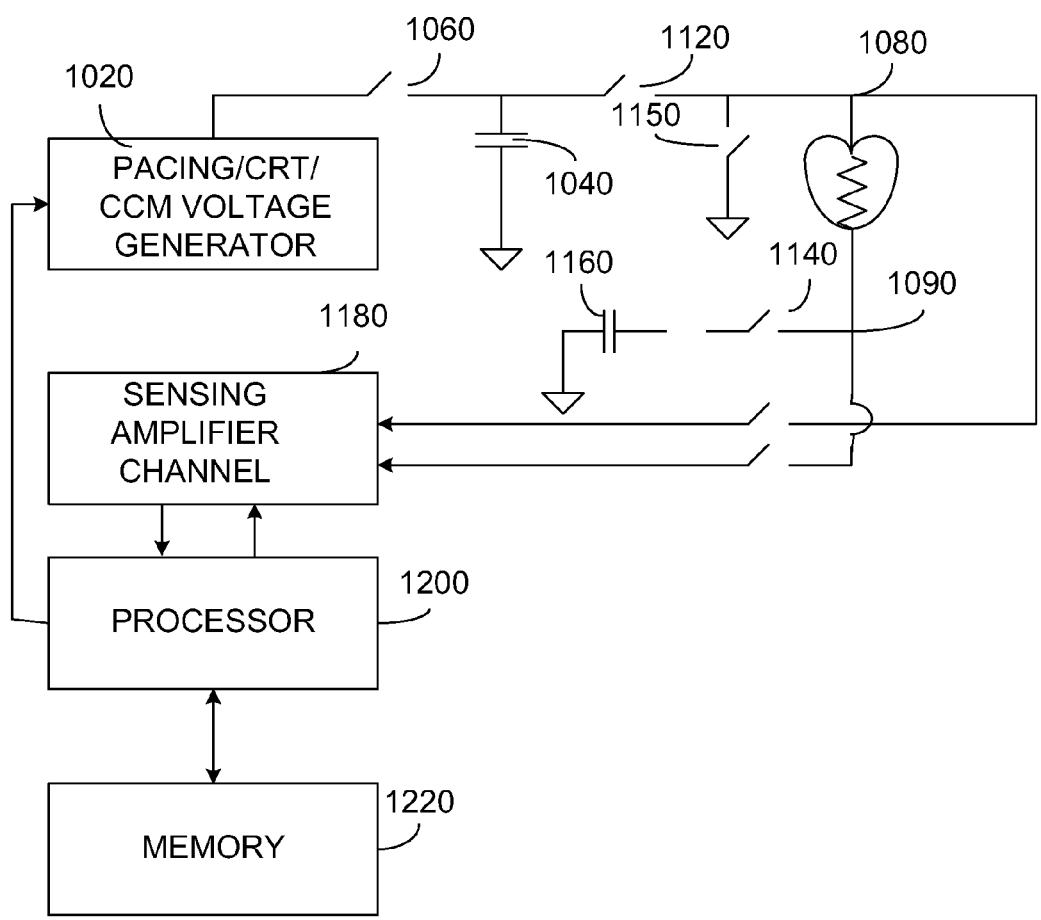
FIG. 10 shows an example of a portions of an implantable cardiac rhythm management device, such as for delivering paces to, or sensing spontaneous intrinsic or evoked intrinsic depolarizations from, a desired portion of a heart.

FIG. 10 shows an example of a portion of an implantable cardiac rhythm management device, such as for delivering paces to, or sensing spontaneous intrinsic or evoked intrinsic depolarizations from, a desired portion of a heart 1000. Spontaneous intrinsic depolarizations are generated by the heart 1000 itself, while evoked intrinsic depolarizations are the result of an electrostimulation pulse such as a pacing pulse or CRT pulse. Depolarization of a heart chamber causes it to contract. After contraction, while the heart chamber is expanding to fill with blood, repolarization occurs.

Figure 17:
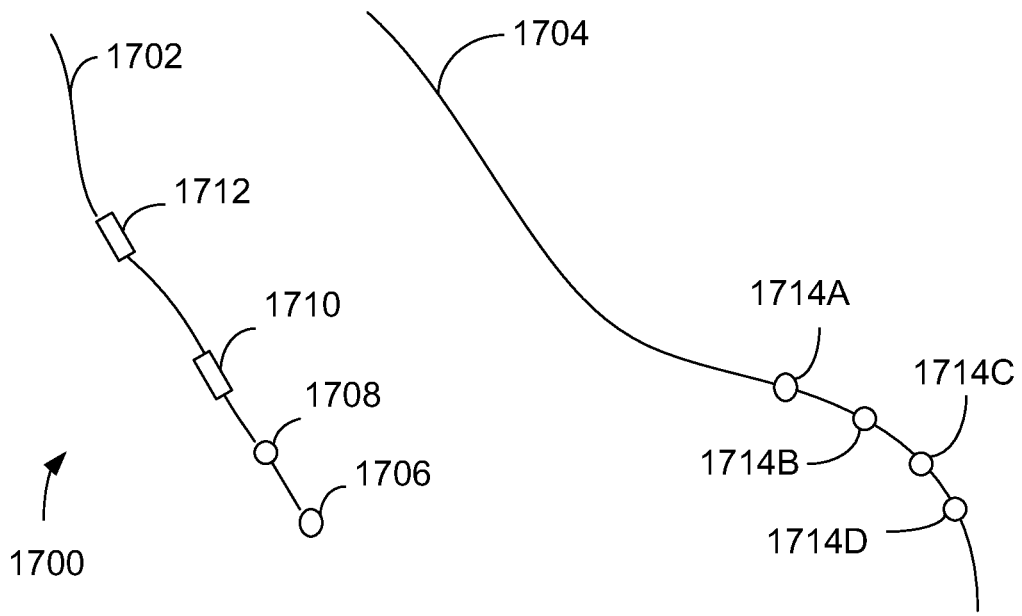
FIG. 17 shows an example of an electrode configuration that can be used for providing CCM, pacing, CRT, and defibrillation shock therapy.

FIG. 10 illustrates an example of a pacing/CRT/CCM voltage generator 1020, which generates a regulatable voltage that is stored on a pacing supply capacitor 1040. A switch 1060 can be used to selectively couple or decouple the pacing voltage generator 1020 to or from the supply capacitor 1040. A pace/CRT/CCM pulse can be delivered to the heart 1000, such as via electrodes 1080 and 1090 (e.g., on a lead 1702, 1704, in certain examples, as shown in FIG. 17, for instance), such as by closing switches 1120 and 1140. In this example, during delivery of the pacing pulse, a coupling capacitor 1160 is included in the return path from the electrode 1090 to ground. Alternatively, the coupling capacitor 1160 can be configured in series between the pacing supply capacitor 1040 and the pacing electrode 1080. After a non-zero delay period following the delivery of the pacing pulse, such as during the repolarization of the heart, a "recharge" period can be initiated. During the recharge period, switch 1120 is opened and switches 1140 and 1150 can be closed to bleed the voltage accumulated during the pace/CRT/CCM pulse from the coupling capacitor 1160 back toward zero via the heart 1000.

Figure 11:
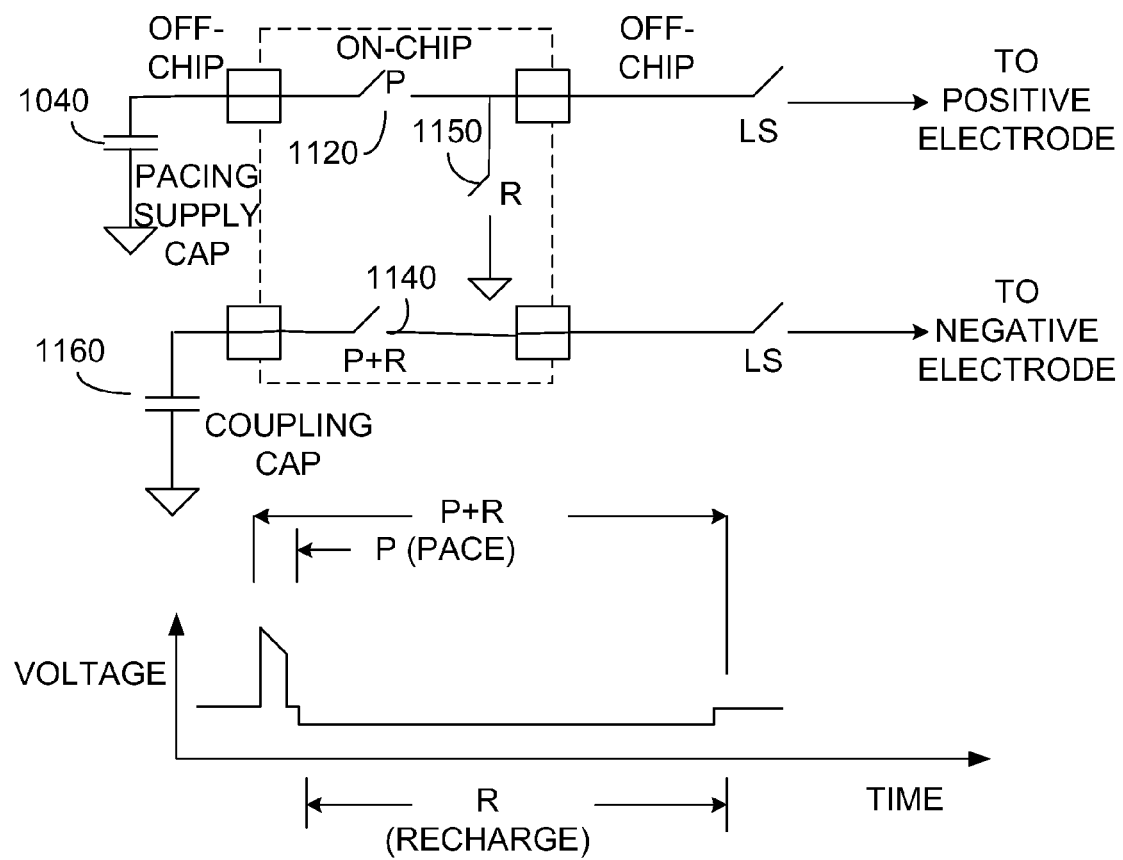
FIG. 11 shows an example of the voltage waveform between electrodes during "pacing" and "recharge" periods "P" and "R," respectively, along with another illustration of the switching configuration.

FIG. 11 shows an example of the voltage waveform between the electrodes 1080 and 1090 (of FIG. 10) during "pacing" and "recharge" periods "P" and "R," respectively, along with another illustration of the switching configuration, which additionally includes off-chip lead switches "LS" that are ordinarily "on" except during internal or external defibrillation shocks. (Note: The "LS" lead switch may not be present in a bradycardia pacer device, depending on the input protection scheme employed). During a pacing period "P", the switches 1120 and 1140 are closed. During the recharge period "R," the switches 1140 and 1150 are closed.

In the example of FIGS. 10 and 11, spontaneous or evoked intrinsic depolarizations can also be sensed, such as between the electrodes 1080 and 1090, via a sensing amplifier channel 1180 (which can include a sensing amplifier as well as other signal processing components). The resulting sensed information can be provided to a processor 1200, such as for further processing. In this example, the processor 1200 can access an onboard or separate memory 1220, such as for reading or storing information. The processor 1200 can also control operation of other components, such as the pacing voltage generator 1020, the switches 1060, 1120, 1140, and 1150, the sensing amplifier channel 1180, or the memory 1220.

In an auto-threshold mode, the implantable device can cycle through various pacing output energies, such as by varying the voltage stored on the pacing supply capacitor 1040, or by varying the pacing pulsewidth time, during which energy stored on the pacing supply capacitor 1040 is coupled to the pacing electrode 1080. By automatically determining the delivered "threshold" energy below which a responsive depolarization is no longer evoked, the pacing output energy can be automatically or manually set to be above that threshold value, such as by a desired safety margin. Similarly, in an auto-capture mode, the implantable device can automatically sense, such as following a delivered pace, to determine whether the delivered pace resulted in a responsive evoked depolarization. The pacing output energy can be automatically adjusted, such as to be above that threshold value, either for a prolonged period of time, or on a beat-to-beat basis.

Thus, auto-capture and atrial auto-threshold can both involve sensing an evoked response from the heart shortly after the delivery of a pacing pulse. A potential challenge to achieving reliable sensing or detection of the evoked response signal is a pace pulse lead polarization (e.g., "afterpotential") artifact as seen across the electrodes 1080 and 1090 directly following a pace/recharge event. In certain examples in which an electrode configuration of the device includes additional electrodes other than electrodes 1080 and 1090 (such as an additional right ventricular coil electrode and an additional right atrial coil electrode, in a defibrillator device), any evoked response can be sensed using such other electrodes— since such other electrodes are different from those used to deliver the pace pulse, they can quickly sense the evoked response without being affected by the afterpotential seen at the electrodes 1080 and 1090. Such a scheme results in little or no pace artifact seen on the evoked response sensing channel.

However, certain bradycardia devices may not have available leads with such separate electrodes to allow such sensing of the evoked response to be independent from the electrodes used to deliver the pacing pulse. In such configurations, evoked response sensing could potentially be affected by such pacing artifacts. The present inventors have recognized, among other things, that one way to reduce or this artifact is to reduce the capacitance of the coupling capacitor 1160, such as during such evoked response sensing. Examples of evoked response sensing are described in U.S. Pat. Nos. 6,226,551, 6,427,085, and 5,941,903, each of which is incorporated by reference herein in its entirety, including its description of evoked response detection. As an illustrative example, the pace artifact during evoked response sensing can be reduced by using a smaller (e.g., 2.2 µF) coupling capacitor 1160 during evoked response sensing, and using a larger (e.g., 10 µF) coupling capacitor 1160 during non-evoked response pacing.

While providing better sensing visibility of the evoked response signal, however, the smaller coupling capacitor value can also alter the shape of the pacing waveform. For example, a smaller coupling capacitor generally results in a faster decay in pacing pulse amplitude, since the voltage droop between the leading edge amplitude and the trailing edge amplitude is a function of the RC time constant formed by the pacing supply capacitor 1040, the coupling capacitor 1160, and the series resistance of the heart load and transistor switches. Thus, using a smaller coupling capacitor value can decrease the trailing edge amplitude of the pace pulse, which, in turn, can effectively limit the usable pacing pulsewidth duration. The present inventors have recognized that one solution is have both a smaller (e.g., 2.2 µF) coupling capacitor 1160 and a larger (e.g., 10 µF) coupling capacitor available, and to automatically use the smaller coupling capacitor 1160 during evoked response sensing (such as during auto-threshold, auto-capture, or both), and to automatically otherwise use the larger coupling capacitor 1160. The present inventors have also recognized that, in a size-constrained implantable device, it is possible to use a switching configuration that "borrows" a coupling capacitor from another pacing channel, such as described further below.

Figure 12:
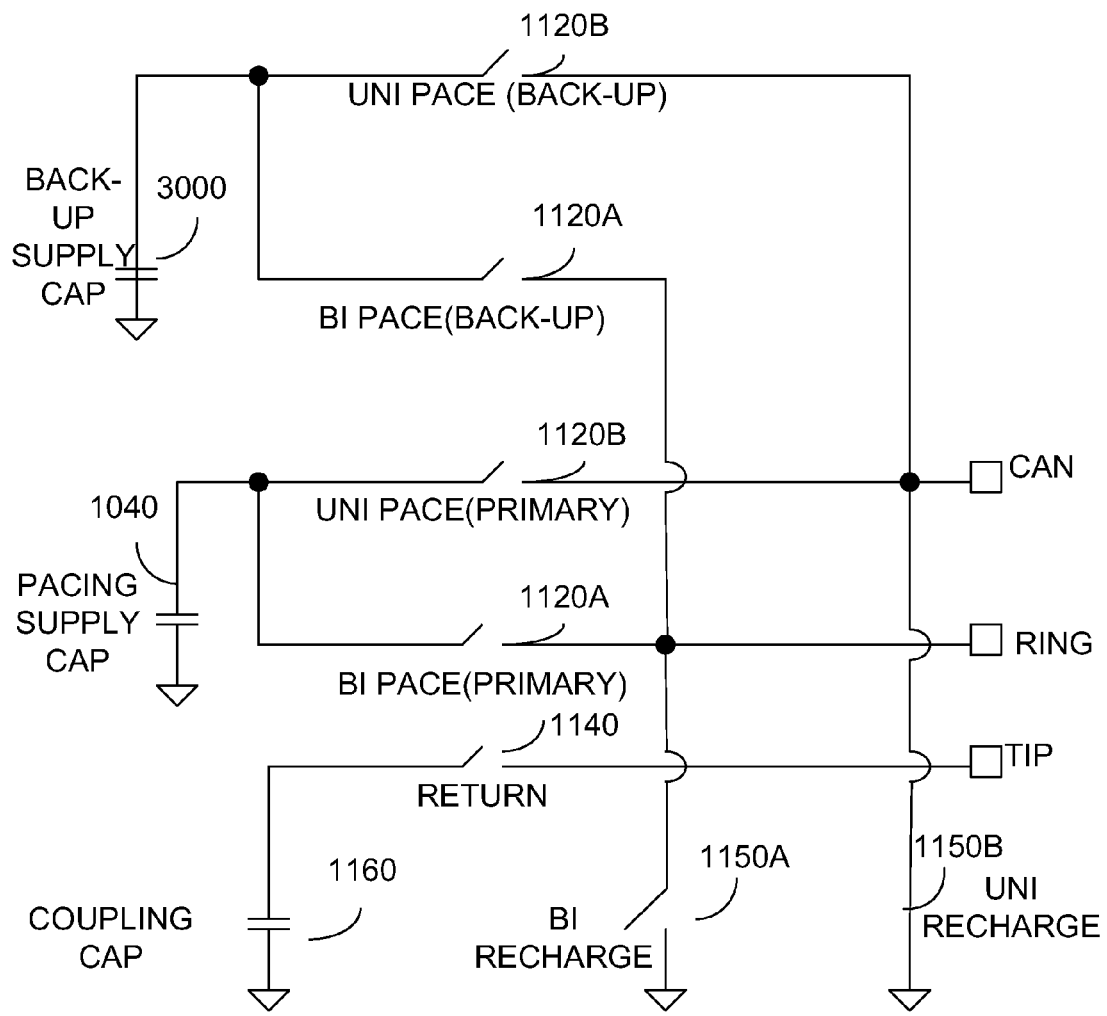
FIG. 12 is a block diagram illustrating generally an example of a switching configuration for a particular pacing channel, where the particular pacing channel can be associated with a particular location of the heart to which the pacing energy is to be delivered.

FIG. 12 is a block diagram illustrating generally an example of a switching configuration for a particular pacing channel, where the particular pacing channel can be associated with a particular location of the heart to which the pacing energy is to be delivered. As an illustrative example, a single-chamber pacing to a right ventricle (RV) can use a single pacing channel, such as shown in FIG. 12. As another illustrative example, dual-chamber pacing to a RV and a right atrium (RA) can use two such pacing channels. As a further illustrative example, tri-chamber pacing to a RA, a RV, and a left ventricle can use three pacing channels. Other configurations or more pacing channels are also possible.

In the example of FIG. 12, in addition to the pacing supply capacitor 1040 and the return coupling capacitor 1160, a back-up pacing supply capacitor 3000 is also included in a particular pacing channel. In this example, each of the normal pacing supply capacitor 1040 and the back-up pacing supply capacitor 3000 include separate respective switches 1120A and 1120B, such as for respectively coupling to a ring electrode during bipolar pacing pulse delivery, and to a can electrode (associated with a housing of the implantable device) during unipolar pacing pulse delivery.

In an example in which multiple such pacing channels are used, the back-up pacing capacitor 3000 from another pacing channel can be "borrowed" by a particular pacing channel for use as its coupling capacitor 1160, such as when auto-capture is not enabled. Indeed, even in a single chamber pacing device with an autothreshold backup pacing supply, the backup pacing supply capacitor can be interchanged with the coupling capacitor (e.g., when not operating in the autothreshold mode) to provide wider pace pulses. In an illustrative example, suppose that an implantable device includes separate RA, RV, and LV pacing channels, each including: a 10 µF pacing supply capacitor 1040, a 2.2 µF coupling capacitor 1160, and a 10 µF back-up pacing supply capacitor 3000. Except when RV autocapture is enabled, the RV pacing channel can use the RA channel's 10 µF backup pacing supply capacitor 3000 as its coupling capacitor 1160. When RV autocapture is enabled, the RV pacing channel uses its own 2.2 µF coupling capacitor 1160, rather than borrowing from another channel. In this example, the "borrowing" of the back-up supply capacitor 3000 from another channel involves closing a switch (not shown) between the capacitor 3000 and the TIP electrode, instead of switch 1140.

In another example, a particular pacing channel can borrow its own back-up pacing capacitor 3000 for use as the coupling capacitor 1160, rather than borrowing from another pacing channel. However, in such an example, back-up pacing for that channel is unavailable, since that channel's own backup pacing capacitor 3000 is being used as the coupling capacitor 1160.

In yet another example, a particular pacing channel can borrow another pacing channel's coupling capacitor 1160 for use as its coupling capacitor 1160, rather than borrowing a back-up pacing supply capacitor from another pacing channel.

As described above, the present inventor has recognized, among other things, that in certain examples that share at least some of the same circuitry for generating and delivering CCM energy as is used for generating and delivering pacing or CRT electrostimulations, unwanted interactions could potentially occur. For example, where CCM uses the same coupling capacitor 1160 as pacing or CRT, residual charge left on the coupling capacitor 1160 by CCM could potentially inhibit a subsequent pacing or CRT electrostimulation pulse from capturing the heart (e.g., evoking a responsive heart contraction).

Figure 13A:
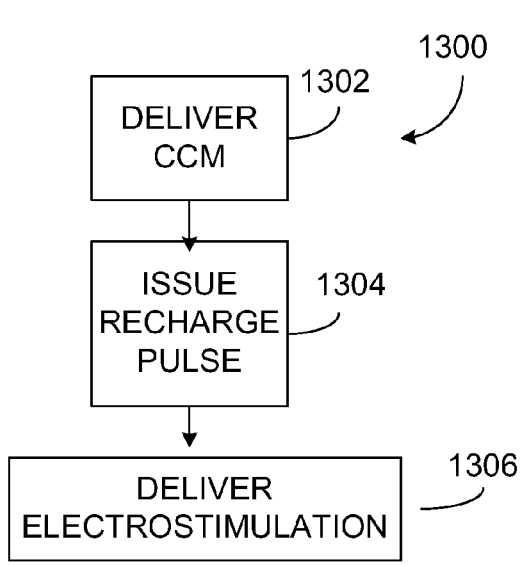
FIG. 13A shows an example of portions of a method such as for using a pacing channel for also delivering CCM therapy.

FIG. 13A shows an example of portions of a method 1300 such as for using a pacing channel for also delivering CCM therapy. At 1302, CCM energy is delivered to the heart, such as by generating an appropriate amount of energy, storing the CCM energy on the pacing supply capacitor 1040, and delivering the CCM energy to the heart including using the coupling capacitor 1160. At 1304, following the CCM therapy delivery to the heart, a recharge pulse is then performed to deplete the coupling capacitor 1160. At 1306, a pacing or CRT electrostimulation can then be generated and delivered, such as by using the pacing supply capacitor 1040 and the coupling capacitor 1160. In an example, the controller 116 can be configured to inhibit or prevent concurrent delivery of the recharge pulse and energy from CCM therapy. Concurrent delivery of the recharge pulse and energy from CCM can cause current flow between the electrodes used for the recharge pulse and the electrodes used for CCM therapy. This current flow can alter (increase or decrease) the intended CCM therapy energy. It can also interfere with maintenance of charge balance for the electrodes used for electrostimulation and CCM therapy. Therefore, in order to avoid such adverse effects, concurrent delivery of the recharge pulse and CCM energy can be inhibited.

Figure 13B:
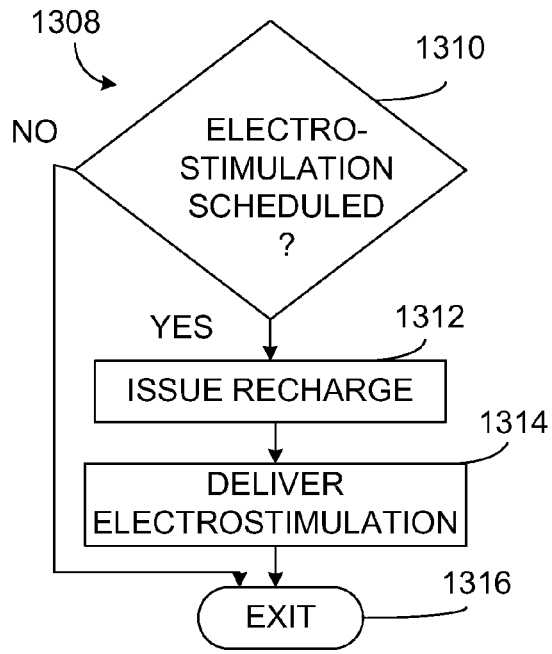
FIG. 13B shows an example of portions of a method such as for using a pacing channel for also delivering CCM therapy.

FIG. 13B shows an example of portions of a method 1308 such as for using a pacing channel for also delivering CCM therapy. At 1310, if a pacing or CRT electrostimulation is scheduled, then, at 1312, a recharge pulse is first issued, such as to deplete the coupling capacitor 1160 of any residual charge that may still be present from any preceding CCM therapy delivery. At 1314, the pacing or CRT electrostimulation is then delivered, before exiting the process at 1316. At 1310, if no pacing or CRT pulse is scheduled, the process is exited at 1316.

Figure 13C:
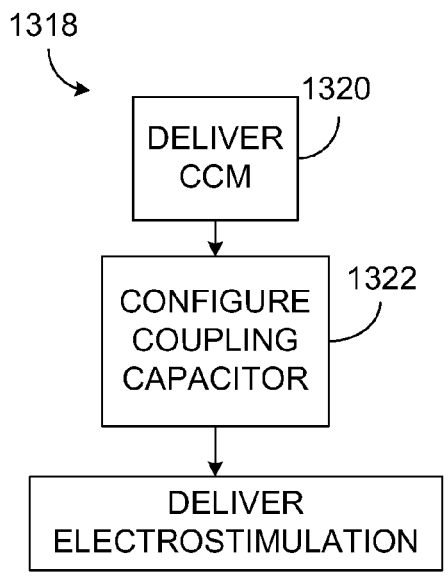
FIG. 13C shows an example of portions of a method, such as for using a pacing channel for also delivering CCM therapy.

FIG. 13C shows an example of portions of a method 1318, such as for using a pacing channel for also delivering CCM therapy. At 1320, CCM energy is delivered to the heart, such as by generating an appropriate amount of energy, storing the CCM energy on the pacing supply capacitor 1040, and delivering the CCM energy to the heart including using the coupling capacitor 1160. At 1322, the shared coupling capacitor 1160 is reconfigured, such that the residual voltage left by the CCM across the coupling capacitor 1160 will be additive to the pacing energy stored on the pacing supply capacitor 1040 for delivery to the heart via the coupling capacitor. An example of how to reconfigure the pacing output channel to provide such additive voltage is described below with respect to FIG. 13F.

Figure 13D:
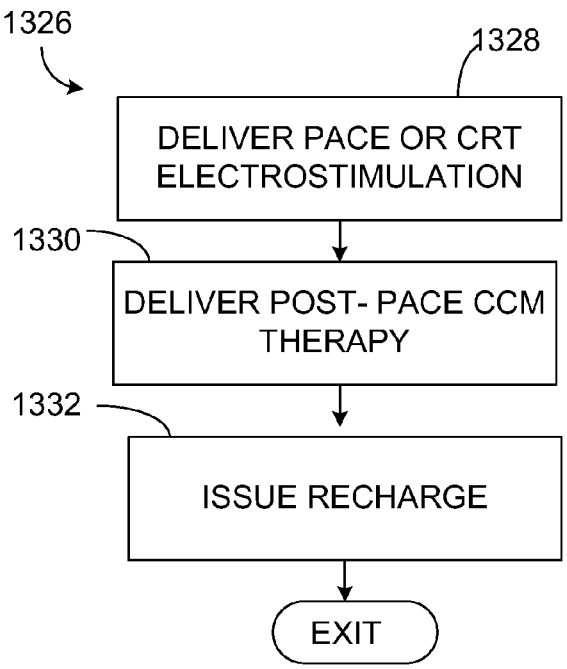
FIG. 13D shows an example of portions of a method, such as for using a pacing channel for also delivering CCM therapy.

FIG. 13D shows an example of portions of a method 1326, such as for using a pacing channel for also delivering CCM therapy. At 1328, upon expiration of a pace or CRT timing escape interval, a pace or CRT electrostimulation is delivered to the heart, such as to one or both ventricles. At 1330, during the post-pace refractory of the heart chamber, CCM therapy is delivered, such as after expiration of a specified first time period timed from the pace or CRT electrostimulation delivery at 1328, e.g., without issuing a recharge between 1328 and 1330, even though the electrostimulation and CCM share the coupling capacitor 1160. At 1332, after both the electrostimulation and the CCM therapy have been delivered, a recharge is then issued, such as to deplete residual charge stored on the coupling capacitor 1160, before process flow exits at 1332.

Figure 13E:
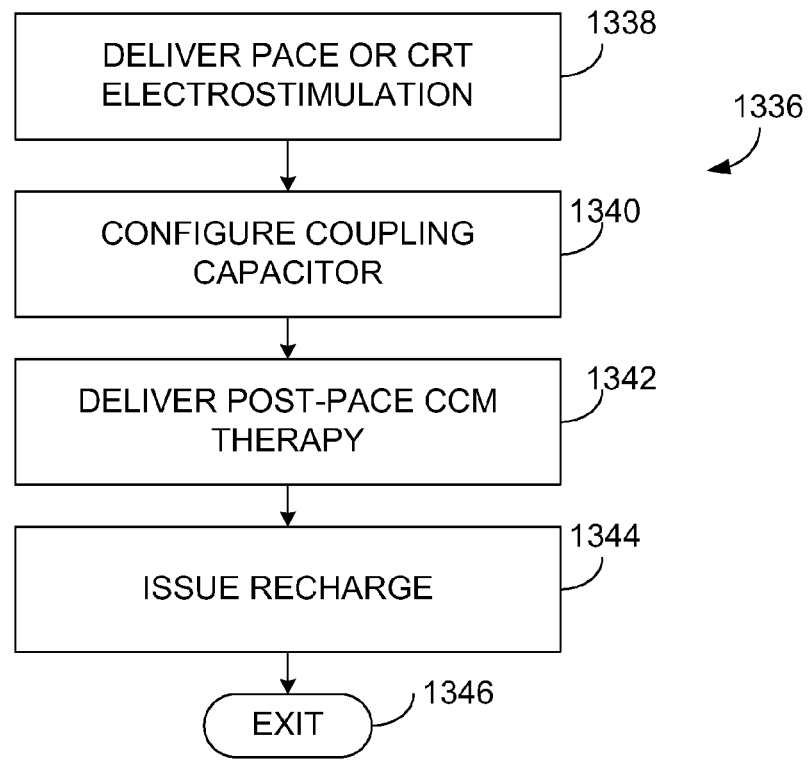
FIG. 13E shows an example of portions of a method, such as for using a pacing channel for also delivering CCM therapy.

FIG. 13E shows an example of portions of a method 1336, such as for using a pacing channel for also delivering CCM therapy. At 1338, upon expiration of a pace or CRT timing escape interval, a pace or CRT electrostimulation is delivered to the heart, such as to one or both ventricles. At 1340, the coupling capacitor 1340 is then configured such that residual voltage left by the pace or CRT electrostimulation across the coupling capacitor will be additive to the CCM energy to be delivered, in a manner similar to that described above for making residual CCM energy additive to pacing. At 1342, during the post-pace refractory of the heart chamber, CCM therapy is delivered, such as after expiration of a specified first time period timed from the pace or CRT electrostimulation delivery at 1338, e.g., without issuing a recharge between 1338 and 1342, even though the electrostimulation and CCM share the coupling capacitor 1160. At 1344, after both the electrostimulation and the CCM therapy have been delivered, a recharge is then issued, such as to deplete residual charge stored on the coupling capacitor 1160, before process flow exits at 1346.

Figure 13F:
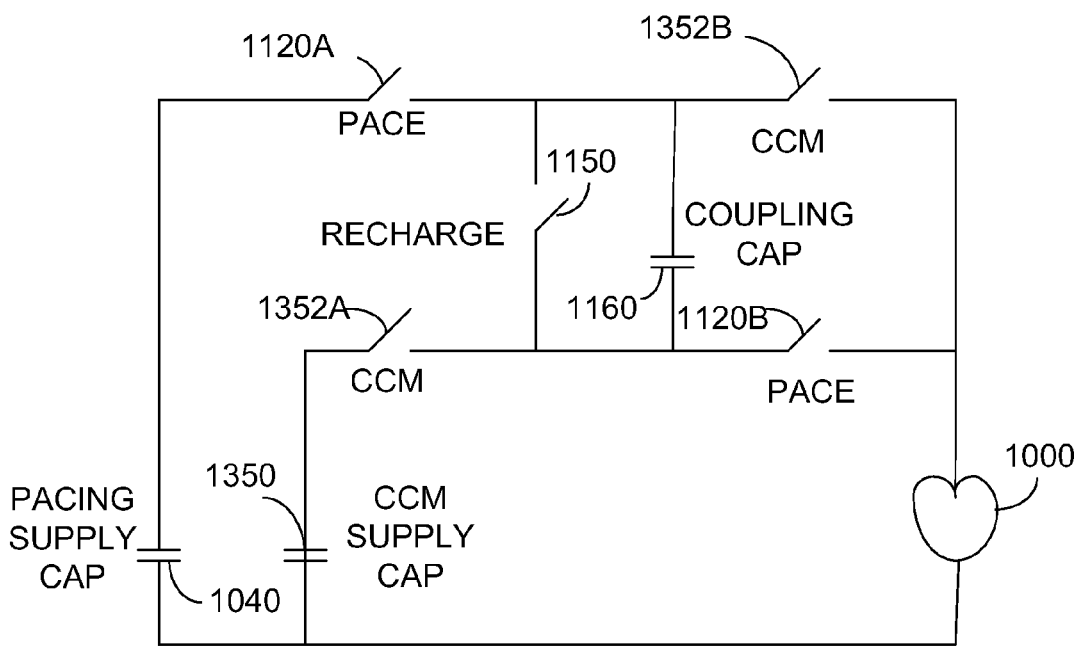
FIG. 13F shows an example of portions of a method, such as for using a pacing channel for also delivering CCM therapy.

FIG. 13F shows an example of a portion of an implantable medical device, such as for delivery cardiac rhythm management and CCM therapy. In this example, closing the CCM switches 1352A, 1352B results in CCM energy delivery from the CCM supply capacitor 1350 to the heart 1000 via the CCM switches 1352A, 1352B and the coupling capacitor 1160. CCM energy delivery can be terminated by opening the CCM switches 1352A, 1352B. In an example, CCM energy delivery results in a residual voltage across the coupling capacitor 1160. After a non-zero delay period following the termination of CCM energy delivery, pacing energy can be delivered to the heart 1000 by closing the pacing switches 1120A and 1120B. Closing the pacing switches 1120A and 1120B delivers pacing energy from the pacing supply capacitor 1040 to the heart 1000 via the pacing switches 1120A and 1120B and the coupling capacitor 1160. The residual charge on the coupling capacitor 1160 resulting from the delivery of CCM energy is additive to the pacing energy, in this example. Recharge of any undesirable charge on the coupling capacitor 1160 can be removed by closing the recharge switch 1150.

9. Example of CCM Integration with Intrinsic Heart Signal Sensing

The present inventor has recognized, among other things, that in certain examples, delivering CCM energy to the heart could potentially interfere with intrinsic heart signal sensing, such as by being erroneously detected as a heart depolarization, or by perturbing or even saturating sense amplifier inputs such as to inhibit sensing of an actual heart depolarization.

Figure 14A:
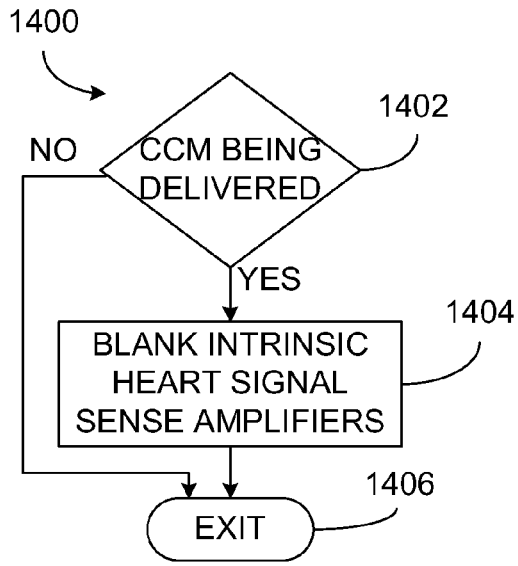
FIG. 14A shows an example of portions of a method for helping avoid interaction between CCM delivery and intrinsic heart signal sensing.

FIG. 14A shows an example of portions of a method 1400 for helping avoid interaction between CCM delivery and intrinsic heart signal sensing. At 1402, if CCM is being delivered (e.g., during delivery of CCM energy and optionally during a subsequent recharge pulse), then, at 1404, intrinsic heart signal sensing amplifiers are "blanked." In an example, such blanking can include opening one or more switches to isolate their one or more of their sensing inputs from their corresponding sensing electrodes associated with the heart. During such sense amplifier blanking, the one or more sensing inputs can optionally be held at the same signal values as preceded the blanking, or connected by one or more switches to a biasing circuit that provides a specified biasing signal value. In another example of blanking, the sense amplifier inputs are not isolated from their respective outputs, but the sense amplifier output signals are ignored during the blanking period. After blanking at 1404, process flow is then exited at 1406. At 1402, if CCM is not being delivered, then process flow proceeds directly to 1406 and exits.

Figure 14B:
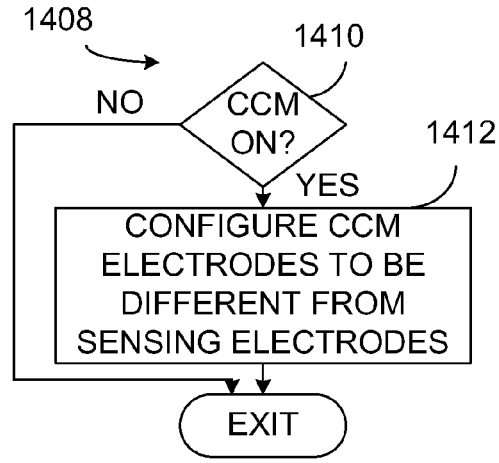
FIG. 14B shows an example of portions of a method for helping avoid interaction between CCM delivery and intrinsic heart signal sensing.

FIG. 14B shows an example of portions of a method 1408 for helping avoid interaction between CCM delivery and intrinsic heart signal sensing. At 1410, if CCM therapy is turned on, then, at 1412, the CCM delivery electrodes are configured to be different electrodes from those used for intrinsic heart signal sensing by the one or more intrinsic heart signal sensing amplifiers. This can help reduce perturbation of the intrinsic heart signal sensing amplifiers by the CCM pulse delivery.

Figure 14C:
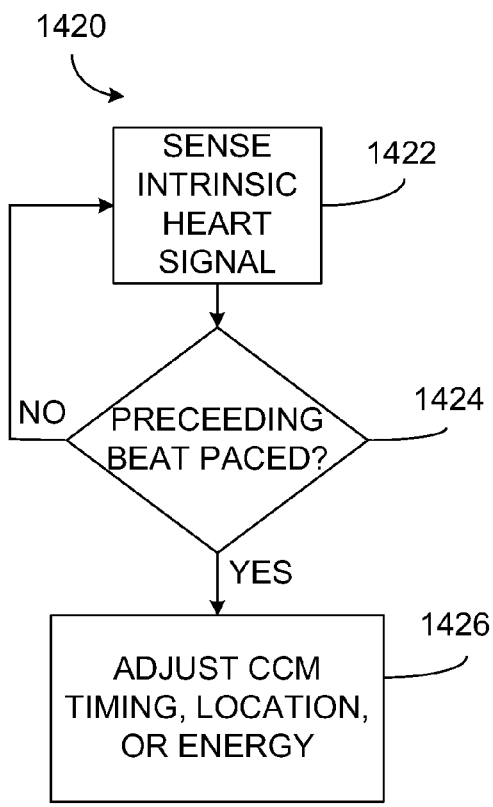
FIG. 14C shows an example of portions of a method for coordinating CCM therapy delivery and intrinsic heart signal sensing.

FIG. 14C shows an example of portions of a method 1420 for coordinating CCM therapy delivery and electrical heart signal sensing. At 1422, a heart signal can be sensed. At 1424, if the preceding sensed heart signal was a paced beat, then, at 1426, at least one of the timing, location, or energy of CCM therapy can be adjusted. For example, because a paced depolarization can be slower than an intrinsic depolarization, it is believed that delaying the timing of CCM therapy after a paced beat, as compared to an intrinsic beat, can be advantageous. Furthermore, if pacing therapy and CCM therapy are delivered to different cardiac chambers, it is believed that it can be advantageous to delay the delivery of CCM therapy (as compared to the timing of CCM delivery when CCM therapy is delivered to the same cardiac chamber as the pacing therapy), such as to provide or accommodate an interchamber delay. In an example, CCM therapy and pacing therapy can be delivered to the same cardiac chamber, such as to avoid an interchamber delay that can affect CCM timing. In an example, CCM therapy and pacing therapy can be delivered to different cardiac chambers, such as to avoid potential interference between CCM delivery and pacing therapy, or to provide CCM therapy at a location where in certain circumstances it is believed can provide the desired physiologic benefit.

10. Example of CCM Integration with Tachyarrhythmia Detection

The present inventor has recognized, among other things, that in certain examples, delivering CCM energy to the heart could potentially interfere with tachyarrhythmia detection, tachyarrhythmia classification, or tachyarrhythmia treatment.

Figure 15A:
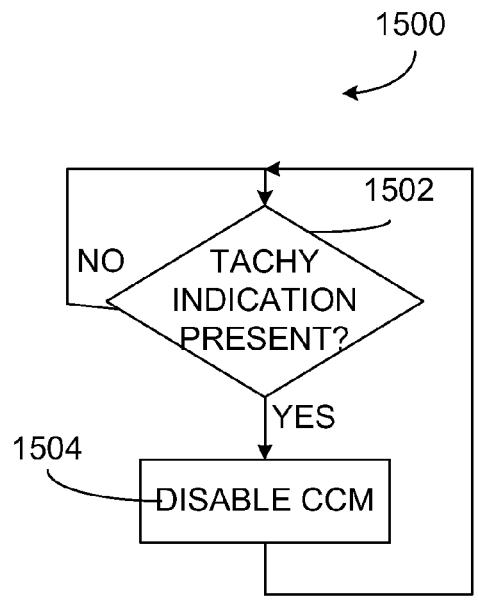
FIG. 15A shows an example of portions of a method, such as for helping avoiding unwanted interaction between CCM delivery and tachyarrhythmia detection, classification, or treatment.

FIG. 15A shows an example of portions of a method 1500, such as for helping avoiding unwanted interaction between CCM delivery and tachyarrhythmia detection, classification, or treatment. At 1502, if a tachyarrhythmia indication is present, then, at 1504, CCM is disabled while the tachyarrhythmia indication continues to be present. In an example, the tachyarrhythmia indication includes the detection of a condition that includes specified number of "fast" beats (e.g., at a heart rate exceeding a threshold tachyarrhythmia rate value). In an example, the condition can include a specified number of consecutive fast beats. In another example, the condition can include a specified number of fast beats out of a specified number of consecutive beats (e.g., "X" of "Y" fast beats). In another example, the condition can include detection of a specified one or more beats exhibiting a tachyarrhythmic morphology. In another example, the condition can include detecting a sudden acceleration in heart rate. Various individual conditions can be combined, such as to form a more complex test providing the tachyarrhythmia indication.

Figures 15B, 16A:
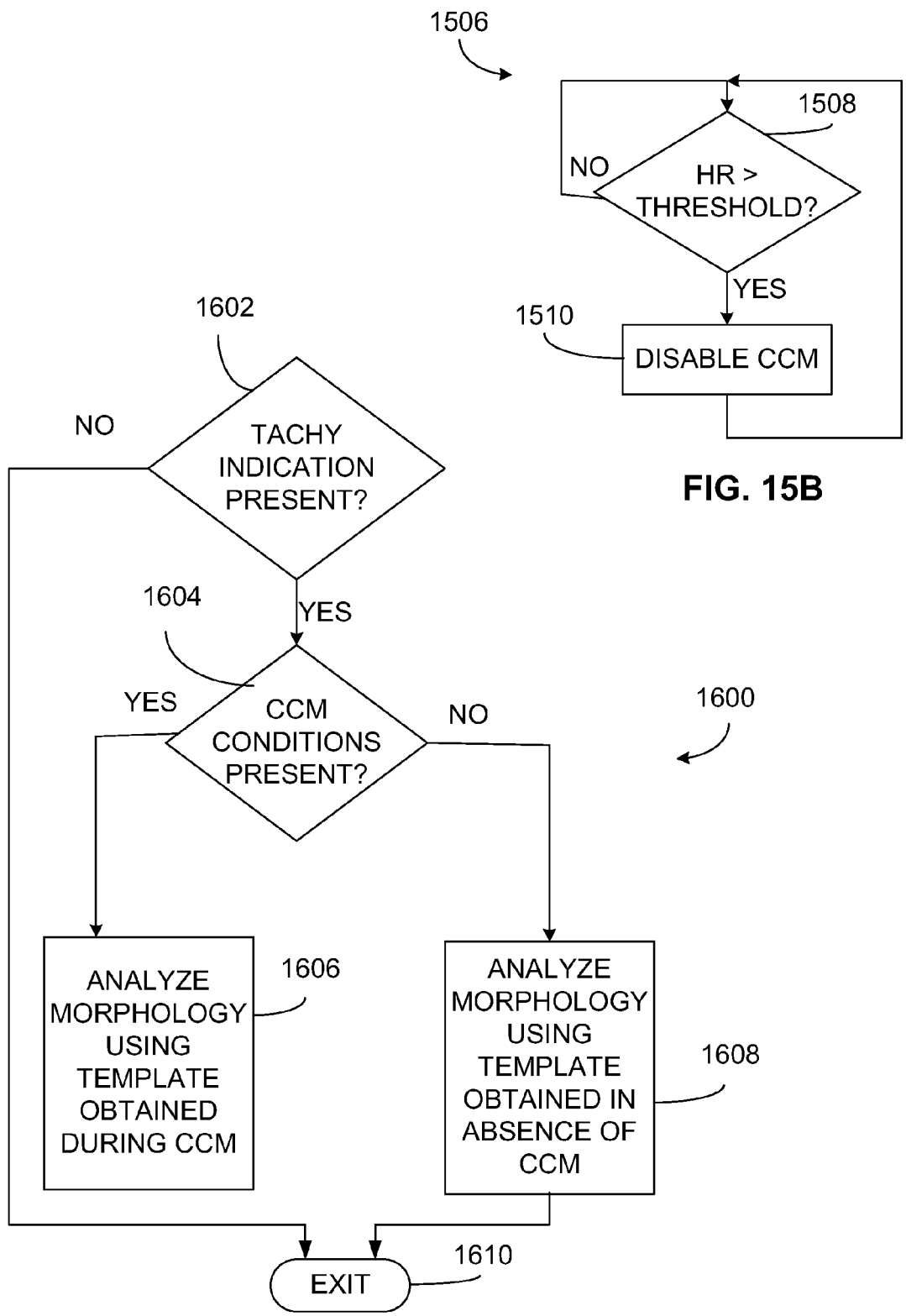
FIG. 15B shows an example of portions of a method, such as for helping avoiding unwanted interaction between CCM delivery and tachyarrhythmia detection, classification, or treatment.
FIG. 16A shows an example of portions of a method, such as for helping avoid unwanted interaction between CCM delivery and tachyarrhythmia detection or classification using a morphological analysis.

FIG. 15B shows an example of portions of a method 1506, such as for helping avoiding unwanted interaction between CCM delivery and tachyarrhythmia detection, classification, or treatment. At 1508, if a heart rate exceeding a specified rate threshold value (e.g., a tachyarrhythmia rate threshold value) is detected, then, at 1510, CCM is disabled until the heart rate is no longer above the threshold value.

11. Example of CCM Integration with Tachyarrhythmia Detection or Classification Using Morphology The present inventor has recognized, among other things, that in certain examples, delivering CCM energy to the heart could potentially interfere with tachyarrhythmia detection or classification that uses the morphology of a detected heart depolarization. For example, discrimination between a supraventricular tachyarrhythmia (SVT) and a ventricular tachyarrhythmia (VT) can include comparing a morphology of a detected heart depolarization to a template morphology representing a particular type of beat (e.g., a normal sinus rhythm (NSR) beat, an SVT beat, or a VT beat). However, delivering CCM energy to the heart could potentially alter the morphology of the detected beat, which could make comparison to the template difficult.

FIG. 16A shows an example of portions of a method 1600, such as for helping avoid unwanted interaction between CCM delivery and tachyarrhythmia detection or classification using a morphological analysis, such as can be used to compare a morphology of a detected beat to a morphological template. At 1602, it is determined whether a tachyarrhythmia indication is present. In an example, this can include detecting a heart rate that exceeds a tachyarrhythmia threshold rate value. In other examples, this can include detecting one or more of any of the other tachyarrhythmia indications described elsewhere in this document. If a tachyarrhythmia indication is present at 1602, then at 1604, it is determined whether CCM conditions are present. In an example, this includes the CCM therapy service being turned on. In another example, this includes the CCM therapy service being turned on, or having recently been on (e.g., within a specified preceding amount of time, e.g., 5 minutes). If CCM conditions are present at 1604, then at 1606, beat morphology is analyzed using a beat morphology template that was previously obtained with CCM turned on, and process flow then continues to 1610. Otherwise, if CCM conditions are not present at 1604, then, at 1608, beat morphology is analyzed using a beat morphology template that was obtained with CCM turned off, and process flow then continues to 1610. At 1602, if no tachyarrhythmia indication is present, then process flow continues to 1610.

Figure 16B:
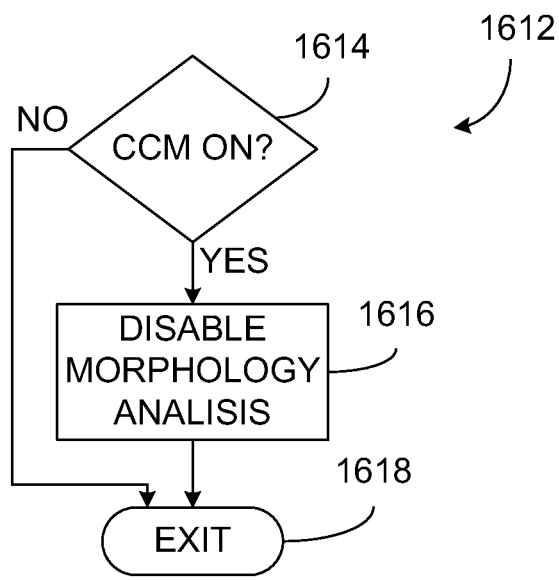
FIG. 16B shows an example of portions of a method, such as for helping avoid unwanted interaction between CCM delivery and tachyarrhythmia detection or classification using morphological analysis.

FIG. 16B shows an example of portions of a method 1612, such as for helping avoid unwanted interaction between CCM delivery and tachyarrhythmia detection or classification using morphological analysis, such as can be used to compare a morphology of a detected beat to a morphological template.

At 1614, it is determined whether CCM is turned on. If so, then, at 1616, morphology analysis is disabled. One or more other (non-morphological) techniques can be used under such a circumstance to perform the tachyarrhythmia detection or classification. After morphology analysis is disabled at 1616, process flow continues to 1618. If, at 1614, CCM is not turned on, then morphology analysis is not disabled; instead, process flow continues directly to 1618. In an example, the disabling of morphology analysis at 1616 while CCM therapy is turned on can be followed by re-enabling of morphology analysis after CCM therapy has been turned off.

12. Example of CCM Integration with Impedance Sensing

The present inventor has recognized, among other things, that in certain examples, delivering CCM energy to the heart could potentially be useful in providing a controlled non-stimulatory energy that could also be used for performing thoracic impedance sensing, intracardiac impedance sensing, or any other desired impedance sensing. This can help conserve the power consumed by the implantable device 102, thereby prolonging its longevity. For example, thoracic impedance sensing can be used to detect information about the subject's breathing, heart contractions, or thoracic fluid accumulation status (e.g., pulmonary edema, hypotension, etc.). In an example, thoracic impedance can be used to measure a subject's "minute ventilation," in which breathing rate and tidal volume information can be used to provide a physiologic sensor-indication of a patient's metabolic need for increased or decreased cardiac output, which can be used to adjust the pacing rate provided to the subject. Intracardiac impedance can similarly be used to determine a pre-ejection interval (PEI), which can also be used to provide a physiologic-sensor indication of metabolic need, such as for adjusting pacing rate. Intracardiac impedance can also be used to provide an indication of contractility. These examples are merely illustrations of some of the various applications in which impedance information can be useful, and are not intended to be limiting.

In an example, the desired impedance parameter can be obtained by delivering CCM energy to the heart via designated electrodes, and measuring a responsive characteristic via impedance sensing electrodes. The CCM energy pulses delivered to the heart can be the exclusive source of impedance information, in an example, or the CCM pulses can be supplemented by other impedance-sensing test energy pulses that are not delivered as CCM pulses, in another example.

Using the CCM energy pulses as impedance test energy pulses can also provide synergy over the non-CCM energy pulses typically used for impedance sensing, because the non-CCM pulses typically used for impedance sensing are usually kept to an amplitude, frequency, and repetition rate at which they will not create a discernable artifact on an ECG strip, which could confuse a diagnosing clinician. Since non-stimulatory CCM pulses likely involve providing a greater energy than such non-stimulatory and non-artifact-producing typical impedance test energy pulses, using the CCM pulses for also providing impedance information can provide such impedance information having a better signal-to-noise characteristic than non-CCM derived impedance information. As mentioned above, if the CCM delivery rate is too low to provide the desired sample rate for impedance sensing, the combined CCM/impedance sensing pulses can be supplemented by non-CCM impedance sensing pulses, such as to provide a higher impedance sampling rate.

13. Examples of CCM Uses of Electrode Configurations

FIG. 17 shows an example of an electrode configuration 1700 that can be used for providing CCM, pacing, CRT, and defibrillation shock therapy. In this example, the electrode configuration can include an intravascular right ventricular (RV) lead 1702 and an intravascular left ventricular (LV) lead 1704. In this example, the RV lead 1702 can be introduced through the right atrium and into the right ventricle. In this example, the RV lead 1702 can include an RV tip electrode 1706, which can be positioned near the RV apex of the heart, a slightly more proximal RV ring electrode 1708, an even slightly more proximal distal RV coil electrode 1710, and an even more proximal supraventricular (SV) coil electrode 1712. In this example, the LV lead 1704 can be configured to be inserted through the right atrium and coronary sinus into the great cardiac vein, such that its electrodes 1714A-D are each located in association with the left ventricle (LV).

The present inventor has recognized, among other things, that the electrode configuration 1700, and other electrode configurations, can offer multiple locations from which CCM therapy can be delivered, thereby creating different "vectors" for delivering CCM therapy to the heart. The present inventor has also recognized that it can be beneficial to select particular electrodes for delivering CCM therapy, such as for enhancing contractility of particular portions of the heart. The present inventor has further recognized that it can be beneficial to cycle or otherwise vary the particular electrodes for delivering CCM therapy, such as for enhancing contractility of various different regions of the heart at different times.

In an illustrative example, RV CCM therapy delivery can be sequentially delivered (e.g., during successive cardiac cycles) between electrode pairs (1706, 1708), (1706, 1710), (1710, 1712) while LV CCM therapy is sequentially delivered (e.g., during successive cardiac cycles) between electrode pairs (1714C, 1714D), (1714A, 1714B). In another illustrative example, RV CCM therapy is concurrently delivered between electrode pairs (1706, 1708), (1710, 1712) while LV CCM therapy is concurrently delivered between electrode pairs (1714A, 1714B), (1714C, 1714D). Other similar examples of concurrent or successively-cycled selected CCM electrode pairs are similarly possible, such as for providing univentricular or biventricular CCM therapy.

In an example, biventricular CCM therapy is provided to the RV and LV with a specified offset time interval value between the RV CCM energy delivery and the LV CCM energy delivery. In an example, the specified offset time interval value is set equal to a specified offset time interval value between RV and LV pace pulses that are also then being delivered as biventricular cardiac resynchronization therapy.

In another example, lead impedance or similar testing can be used to determine whether a particular electrode is operating properly, such as for delivering electrical energy to the heart, and, if failure of a particular electrode being used for delivering CCM therapy is detected, the CCM therapy electrode configuration is automatically reconfigured to deliver the CCM therapy from a combination of electrodes that is deemed still operating properly.

In another example, lead impedance testing can be used to determine which electrodes or combinations of electrodes present a high pacing impedance, and a combination of electrodes with high pacing impedance is automatically selected for delivering the CCM therapy, thereby improving efficiency of delivering the CCM therapy.

14. Examples of CCM Use with Sensor Information

The present inventor has recognized, among other things, that information from a physiological sensor of the implantable device 102 can advantageously be used to control or adjust CCM therapy to obtain clinical benefit to the subject.

Figure 18A:
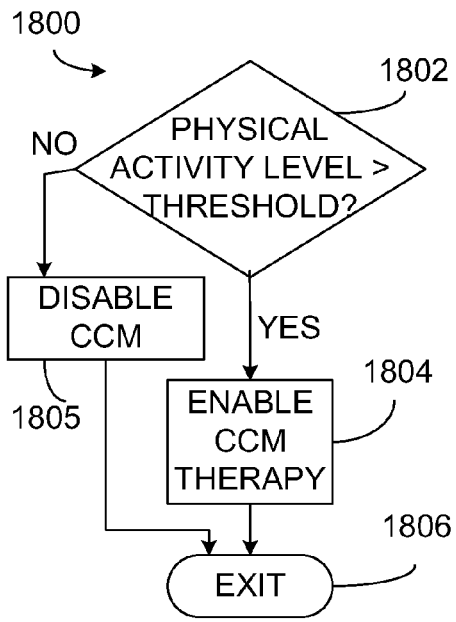
FIG. 18A shows an example of portions of a method for using sensor information for controlling CCM therapy.

FIG. 18A shows an example of portions of a method 1800 for using sensor information for controlling CCM therapy. At 1802, an indication of the subject's physical activity level is compared to a threshold value. In an example, the indication of the subject's physical activity level can be provided by an accelerometer or other activity sensor. In another example, the indication of the subject's physical activity level can be inferred from respiration information, such as can be provided by a thoracic impedance sensor or other respiration sensor. At 1802, if the subject's physical activity level exceeds the threshold activity level value, then, at 1804, CCM therapy can be enabled, before process flow is exited at 1806. Otherwise, at 1802, if the subject's physical activity level does not exceed the threshold activity level value, then, at 1805, CCM therapy is disabled, before process flow is excited at 1806. In this way, CCM therapy can be provided to enhance contractility when it is most needed, that is, when the patient is undergoing a significant amount of physical activity. When the CCM therapy is not needed, it can be inhibited, thereby saving energy and prolonging the longevity of the implantable device 102.

Figure 18B:
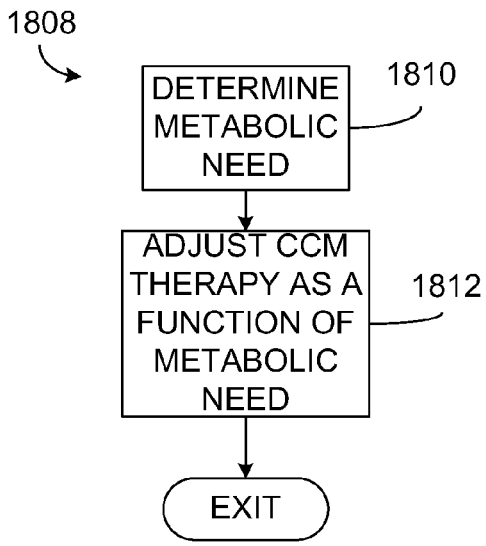
FIG. 18B shows an example of portions of a method for using sensor information for controlling CCM therapy.

FIG. 18B shows an example of portions of a method 1808 for using sensor information for controlling CCM therapy. At 1810, an indication of the patient's metabolic need for increased cardiac output is determined. In an example, the indication of the patient's metabolic need can be provided by an indication of the patient's physical activity level, such as can be provided by an accelerometer, respiration sensor, or the like. At 1812, the CCM therapy is adjusted as a function of the metabolic need. For example, an increased indication of metabolic need can result in delivery of higher energy CCM therapy than a lower indication of metabolic need. In another example, an increased indication of metabolic need can result in delivery of CCM therapy from additional electrode pair locations than a lower indication of metabolic need. In another example, an increased indication of metabolic need results in the delivery of more frequent CCM therapy than a lower indication of metabolic need (e.g., every beat, as opposed to every other beat, or every third beat, etc.).

Figure 18C:
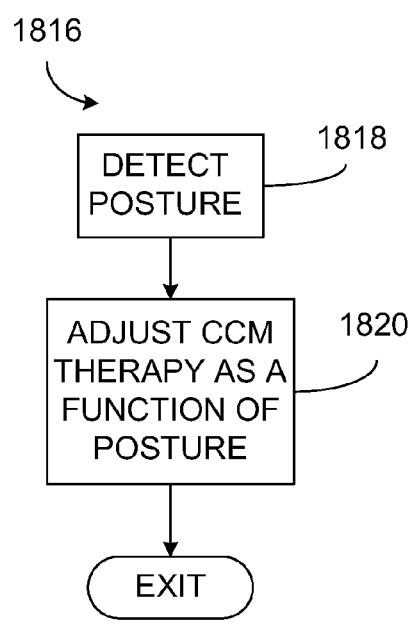
FIG. 18C shows an example of portions of a method for using sensor information for controlling CCM therapy.

FIG. 18C shows an example of portions of a method 1816 for using sensor information for controlling CCM therapy. At 1818, an indication of the patient's posture is detected, such as by using a tilt switch, three axis accelerometer, or other posture sensor. At 1820, the CCM therapy is adjusted as a function of the posture, such as to provide more CCM therapy in a standing portion than in a sitting or supine posture.

Figure 18D:
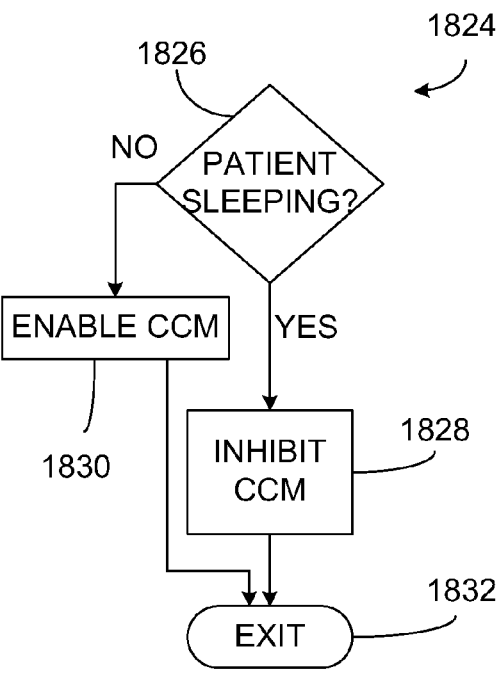
FIG. 18D shows an example of portions of a method for using sensor information for controlling CCM therapy.

FIG. 18D shows an example of portions of a method 1824 for using sensor information for controlling CCM therapy. At 1826, it is determined whether the patient is sleeping, such as by using a sleep detector, which can include one or more of an activity sensor, a respiration sensor, or posture sensor to detect whether the patient is sleeping. At 1826, if the patient is sleeping, then CCM is inhibited (saving energy and increasing device longevity) at 1828, before process flow is exited at 1832. Otherwise, at 1826, if the patient is not sleeping, then CCM is enabled at 1830, before process flow is exited at 1832.

Figure 18E:
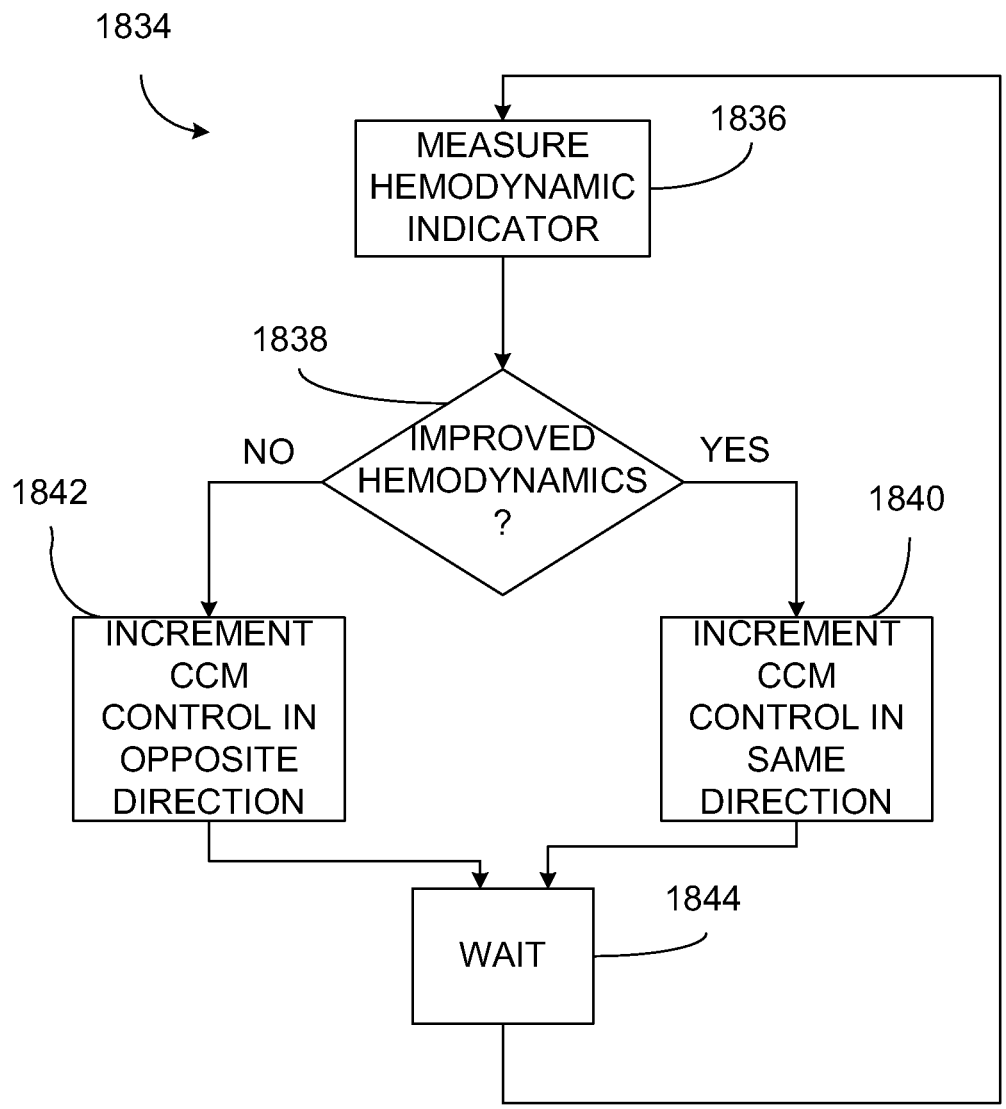
FIG. 18E shows an example of portions of a method for using sensor information for providing closed-loop control of CCM therapy.

FIG. 18E shows an example of portions of a method 1834 for using sensor information for providing closed-loop control of CCM therapy. At 1836, a hemodynamic indicator is measured. In an example, this includes measuring an indicator of contractility, which is believed to be enhanced by providing CCM therapy. In an example, pulmonary artery (PA) or other blood pressure or blood flow sensor is used to provide the measured hemodynamic indicator. In an example, the blood pressure is used to estimate the right ventricular change in blood pressure per unit time (e.g., RV dP/dt), which is used as the measured hemodynamic indicator of contractility.

At 1838, if the measured hemodynamic indicator indicates improved hemodynamics, then at 1840 a CCM control parameter (e.g., energy, repetition rate, electrode configuration, etc.) is adjusted incrementally in the same direction as in a previous iteration, before process flow continues to the wait condition of 1844. Otherwise, at 1842, the CCM control parameter is adjusted incrementally in the opposite direction as the previous iteration before process flow continues to the wait condition of 1844. At 1844, after waiting for a specified period of time, process flow returns to 1836, where the hemodynamic indicator is again measured, and process flow continues as shown in FIG. 18E. In this manner, one or more CCM control parameters can be adjusted, in closed-loop fashion, to maximize a measured indicator of hemodynamics, such as an indicator of contractility. Examples of other possible indicators of contractility that can be used for closed-loop control of CCM therapy can include, by way of example, but not by way of limitation, the AV-interval, or any other surrogate for contractility. Examples of other possible hemodynamic indicators that can be used for closed-loop control of CCM therapy can include, by way of example, but not by way of limitation, transcardiac impedance, or a blood gas (e.g., $CO_2$ or $O_2$).

In some of the above examples, closed-loop control was described so as to maximize contractility, however, in another example, when a measure of contractility exceeds a specified threshold value, then CCM is inhibited, such as to save energy and increase longevity of the implanted device. Thus, in an example, the closed-loop control of CCM can be carried out so as to generally increase contractility, but only up to a specified value, beyond which CCM may not be as effective or as cost-effective (e.g., in terms of energy expended to obtain a further increase in contractility).

Figure 18F:
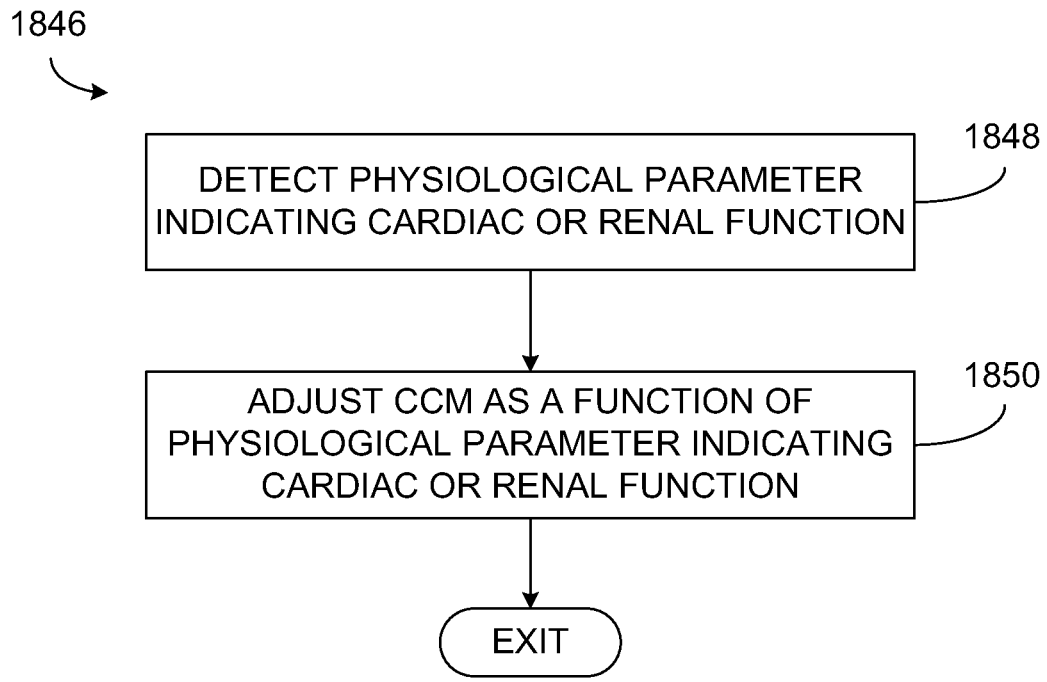
FIG. 18F shows an example of portions of a method for using sensor information for controlling CCM therapy.

FIG. 18F shows an example of portions of a method 1846 for using sensor information for controlling CCM therapy. At 1848, at least one of a physiological parameter, such as indicating cardiac or renal function, can be detected. Examples of physiological parameters indicating cardiac or renal function include concentration of substance, such as electrolytes, such as potassium, sodium, calcium, chloride, or bicarbonate. In an example, an electrolyte can be measured in the blood or interstitial tissue. Other examples of physiological parameters indicating cardiac or renal function include one or more chemicals used to evaluate renal function, such as blood urea nitrogen (BUN), serum creatinine, or glomerular filtration rate (GFR). At 1850, the CCM therapy can be adjusted as a function of the physiological parameter indicating cardiac or renal function. Examples of such CCM adjustments can include adjusting the energy or frequency of CCM delivery, adjusting the CCM electrode configuration, or adjusting the timing of CCM delivery within the refractory period. In an example, CCM therapy can be adjusted as a function of a blood or interstitial calcium level, such that when the detected calcium level is below a specified threshold level, the energy or frequency of CCM can be increased.

Illustrative examples of chemical sensing within an implantable medical device that can be adapted to also be used for adjusting CCM therapy are described in Michael Kane et al. U.S. patent application Ser. No. 11/383,933, filed on May 17, 2006, published on Nov. 22, 200 as US Pat. Pub. No. 20070270675, now issued as U.S. Pat. No. 7,809,441, entitled Implantable Medical Device with Chemical Sensor and Related Methods, which is assigned to Cardiac Pacemakers, Inc., and in Michael Kane et al. U.S. patent application Ser. No. 11/383,926, filed on May 17, 2006 and currently pending, published on Nov. 22, 2007 as US Pat. Pub. No. 20070270674, entitled Methods Regarding Implantable Medical Device with Chemical Sensor, which is assigned to Cardiac Pacemakers, Inc. which are incorporated by reference herein in their entirety, including its description of chemical sensing, their configuration, and methods of use.

Figure 18G:
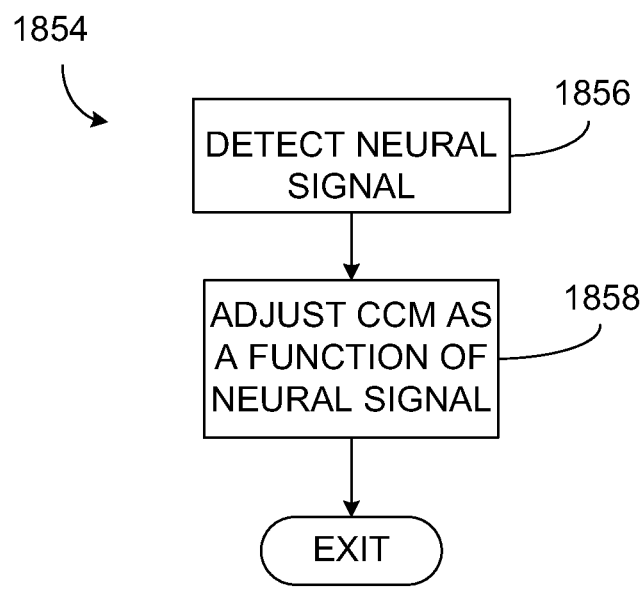
FIG. 18G shows an example of portions of a method for using sensor information for controlling CCM therapy.

FIG. 18G shows an example of portions of a method 1854 for using sensor information for controlling CCM therapy. At 1856, in an example, a neural signal is detected. Examples of a neural signal can include a sympathetic nerve signal or a parasympathetic nerve signal, such as a vagal nerve signal. At 1858, the CCM therapy can be adjusted using information obtained from the neural signal. Examples of such CCM adjustments can include adjusting the energy or frequency of CCM delivery, adjusting the CCM electrode configuration, or adjusting the timing of CCM delivery within the refractory period. In an example, CCM therapy can be adjusted as a function of a vagal nerve signal, such that when there is an increase in vagal nerve activity above a specified threshold level, the energy or frequency of CCM can be increased. Increased vagal nerve activity can be indicative of improvement in heart failure patients. Therefore, it is believed that increased vagal nerve activity can indicate that CCM therapy is working to improve patient condition. In this case, it is believed that increasing the energy or frequency of CCM can further benefit the patient.

15. Examples of CCM Energy Delivery Timing and Tuning

The present inventor has recognized, among other things, that ventricular CCM therapy can be delivered during a refractory period following a ventricular event, wherein the ventricular event can be either a sensed ventricular contraction (e.g., sensed by detecting a QRS complex or otherwise) or a paced ventricular contraction.

Figure 19:
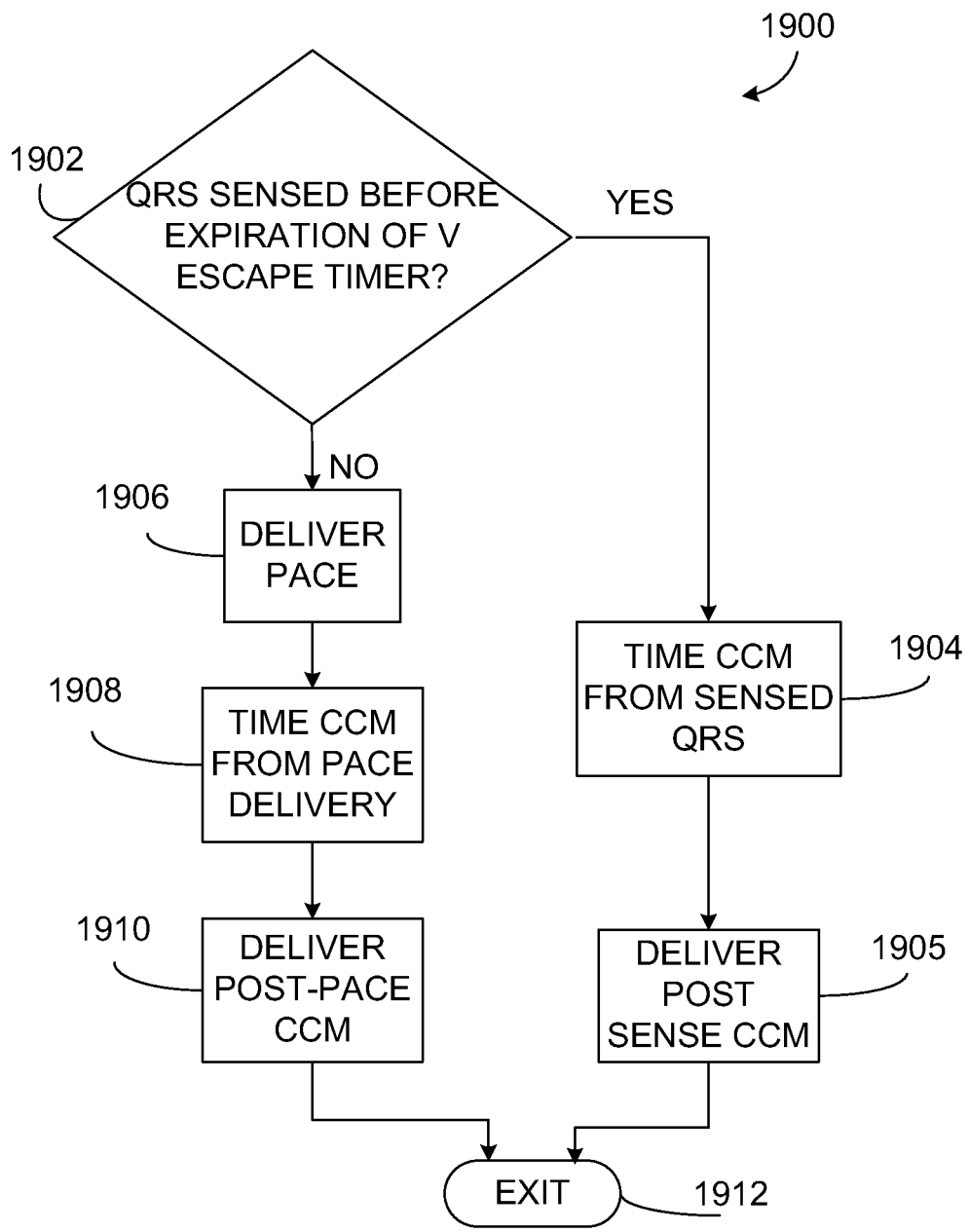
FIG. 19 shows an example of portions of a method for delivering ventricular CCM therapy in conjunction with both sensed QRS complexes and ventricular pacing or CRT pulses.

FIG. 19 shows an example of portions of a method for delivering ventricular CCM therapy in conjunction with both sensed QRS complexes and ventricular pacing or CRT pulses. At 1902, if a QRS complex is sensed before expiration of a ventricular pacing escape timer, then, at 1904, CCM energy delivery can be timed at a specified first delay from the sensed QRS complex or an appropriate fiducial thereof. This can help ensure that the post-sense CCM energy delivery occurs during a post-sense ventricular refractory period when the ventricle is relatively insensitive to contracting in response to electrostimulation. At 1905, a post ventricular sense CCM therapy energy is delivered after the first delay, before process flow exits at 1912. At 1902, if no QRS complex is sensed before expiration of the ventricular pacing escape timer, then, at 1908, a pace (or CRT) pulse is delivered upon expiration of the ventricular pacing escape timer. Then, at 1908, post-pace CCM therapy delivery can be timed at a specified second delay from the expiration of the pacing escape timer. This can help ensure that the post-pace CCM energy delivery occurs during a post-pace ventricular refractory period when the ventricle is relatively insensitive to contracting in response to electrostimulation. At 1910, the post-pace CCM therapy is delivered after the second delay, before process flow exits at 1912.

In an example, the post-sense first delay can be set to a different specified value than the post-pace second delay. For example, a slightly longer (e.g., by about 20 milliseconds) delay can be used for the post-pace second delay than for the post-sense first delay. The slightly longer delay used for the post-pace cardiac cycles can be used, for example, to compensate for the delay in contraction of the ventricles from issuing a pacing pulse(s) as compared to acquiring an signal due to intrinsic contraction of the ventricles. In another example, one or more parameters of the post-sense CCM therapy can be specified to be different from the post-pace CCM delivery. For example, a different CCM dose (e.g., energy) can be used for post-sense CCM delivery than for post-pace CCM delivery. In an example, CCM dose can be increased for post-sense CCM therapy. The increase in CCM dose may provide benefit in post-sense cardiac cycles due to the loss of CRT on these cycles. In an example, CCM dose can be increased for post-pace CCM therapy. In this example the increased CCM dose in intended to compensate for a less effective contraction of the ventricles from pacing as compared to an intrinsic contraction. This can be particularly true for non-CRT ventricular pacing. CCM dose can be altered, for example, by changing the CCM pulse amplitude, pulse width, or pulse train duration.

In an example, CCM therapy delivery can be turned off for one of a post-pace or post-sense scenario, and left on for the other of the post-pace or post-sense scenario. In an example, CCM can be suspended during antitachycardia pacing (ATP) since CCM may be ineffective or harmful at the relatively high rates associated with ATP. In an example, CCM can be suspended during one or more post-pace cycles when ventricular rate regulation (VRR) is enabled since CCM during the relatively shorter cardiac cycle intervals associated with post-sense cycle may be ineffective or harmful. Examples of ventricular rate regulation (VRR) are described in commonly-assigned Kramer et al. U.S. Pat. Nos. 6,411,848, 7,062,325, Krig et al. U.S. Pat. No. 7,142,918, and Kramer et al. U.S. Pat. No. 7,181,278 each of which is incorporated by reference herein in its entirety, including its description of ventricular rate regulation (VRR).

16. Examples of CCM Therapy in Patients with Atrial Fibrillation

The present inventor has recognized, among other things, that CCM therapy is often not provided to patients that exhibit chronic atrial fibrillation (AF). This is primarily because the AF causes irregular or unpredictable ventricular cardiac cycle lengths, which can make it difficult to properly time CCM therapy delivery during ventricular refractory periods. However, the present inventor has also recognized that chronic or paroxysmal (intermittent) AF patients could potentially particularly benefit from CCM therapy, since it could increase contractility, thereby improving cardiac output that is somewhat compromised by the presence of AF.

Figure 20A:
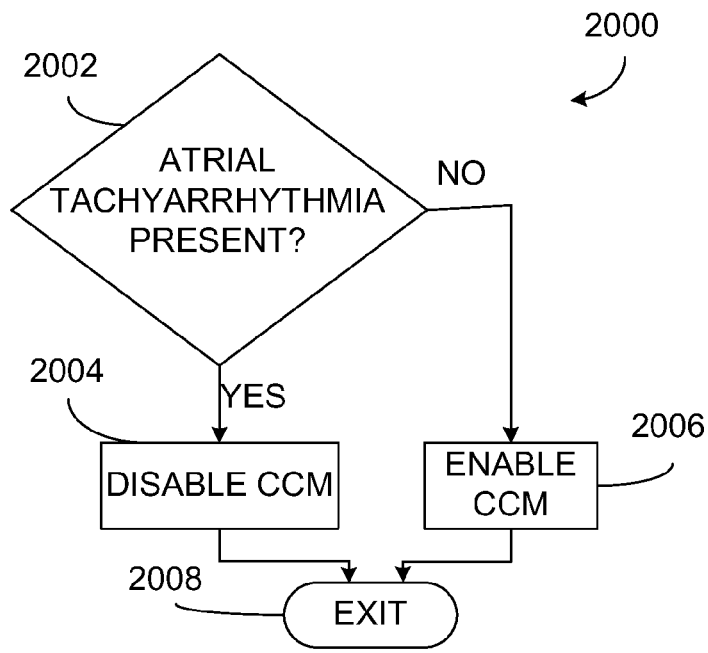
FIG. 20A shows an example of portions of a method, such as for using CCM therapy in a patient with chronic or intermittent AF.

FIG. 20A shows an example of portions of a method 2000, such as for using CCM therapy in a patient with chronic or intermittent AF. At 2002, it is determined whether atrial tachyarrhythmia is present, such as by using an existing atrial tachyarrhythmia episode detection algorithm to detect one or more of supraventricular tachyarrhythmia (SVT), paroxysmal atrial fibrillation (PAF), or premature atrial contractions (PACs), by way of example, but not by way of limitation. At 2002, if atrial tachyarrhythmia is present, then, at 2004, ventricular CCM therapy is disabled before process flow exits at 2008. At 2002, if atrial tachyarrhythmia is not present, then, at 2006, ventricular CCM therapy is disabled before process flow exits at 2008. In an example, the method 2000 can be performed whenever an atrial tachyarrhythmia is detected, or whenever ventricular CCM therapy is about to be delivered.

Figure 20B:
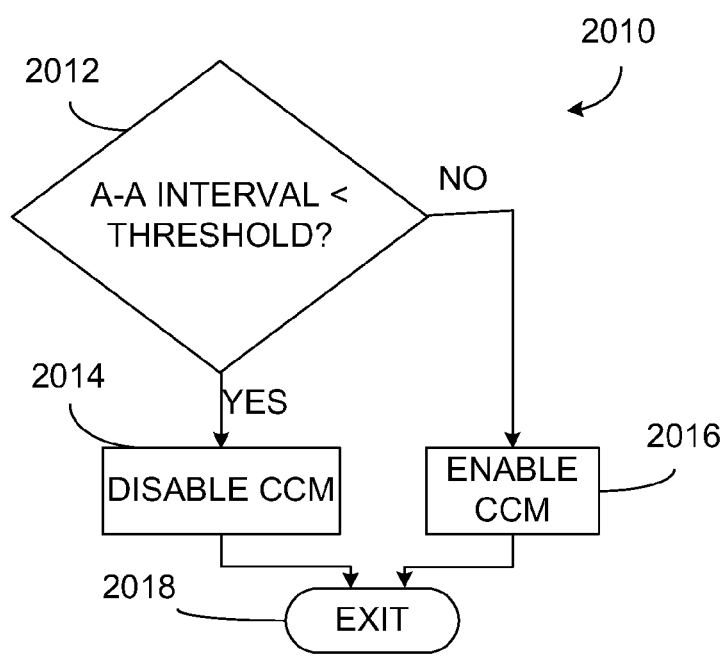
FIG. 20B shows an example of portions of a method, such as for using CCM therapy in a patient with chronic or intermittent AF.

FIG. 20B shows an example of portions of a method 2010, such as for using CCM therapy in a patient with chronic or intermittent AF. At 2012, it is determined whether an interval between successive atrial contractions (A-A interval) is less than an atrial tachyarrhythmia threshold value (e.g., 500 milliseconds). At 2012, if the A-A interval is less than the threshold value, then, at 2014, ventricular CCM therapy is disabled for that cardiac cycle, before process flow exits at 2018. At 2012, if the A-A interval is greater than or equal to the threshold value, then, at 2016, ventricular CCM therapy is enabled for that cardiac cycle, before process flow exits at 2018. In an example, the method 2010 is repeated for each cardiac cycle, such as for each A-A interval.

17. Examples of Integrating CCM Therapy with Neural Stimulation Therapy

The present inventor has recognized, among other things, that CCM therapy can be advantageously used together with neural stimulation therapy. For example, both CCM and vagal neurostimulation (VNS) are believed to increase contractility and, since they employ different mechanisms, it is believed that CCM and VNS can act synergistically to increase contractility. However, VNS and CCM have different power consumptions and, in certain circumstances, VNS can lead to other effects, such as, for example, vasodilation (which can cause a drop in blood pressure) or decreased heart rate (which can decrease cardiac output). Accordingly, the present inventor has recognized that properly managing providing both neurostimulation and CCM using the same implantable device 102 can be both challenging and useful.

Figure 21A:
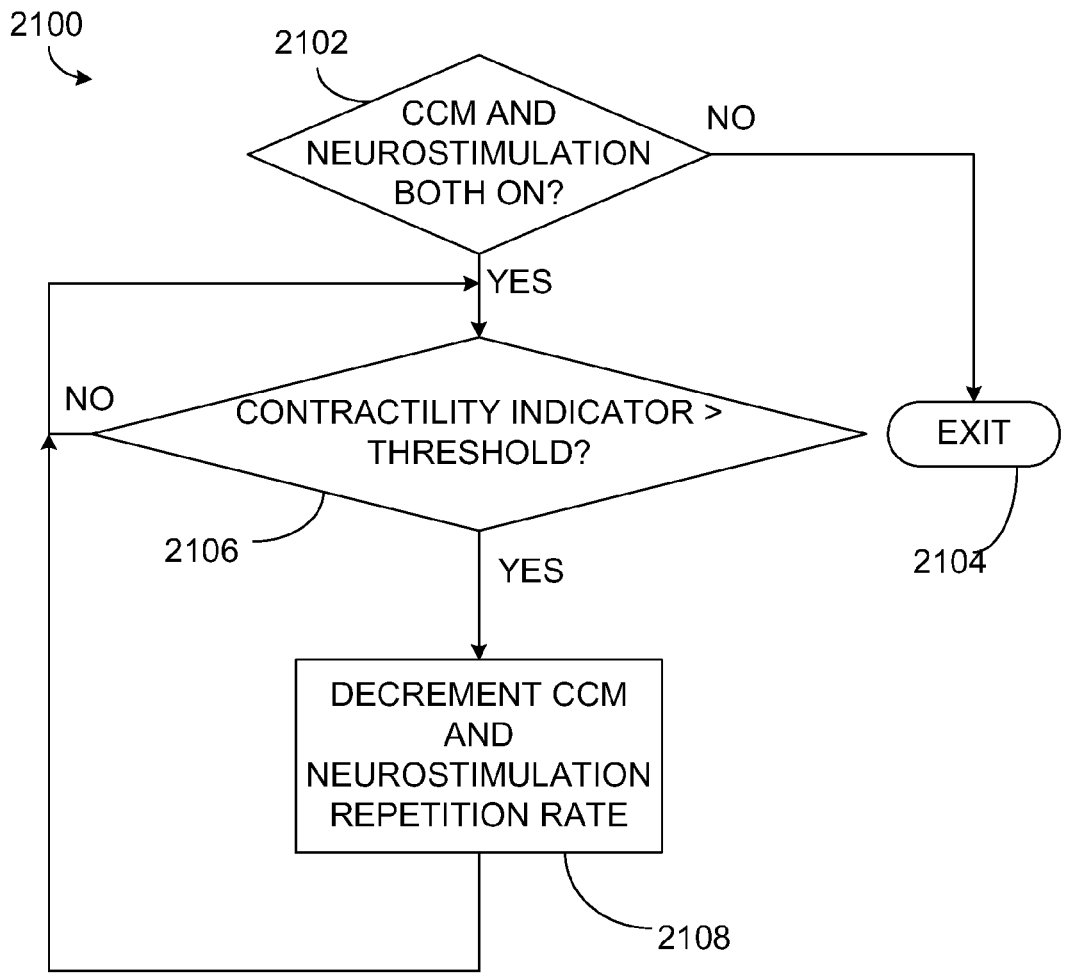
FIG. 21A shows an example of portions of a method for managing CCM and VNS or other neurostimulation.

FIG. 21A shows an example of portions of a method 2100 for managing CCM and VNS or other neurostimulation. At 2102, if CCM and neurostimulation are not both on, then the process exits at 2104. Otherwise, at 2106, it is determined whether a contractility indicator exceeds a specified threshold value. In an example, this includes using a pulmonary artery pressure sensor or other blood pressure sensor to measure a right ventricular rate of change of blood pressure over time (RV dP/dt), which is indicative of contractility in that higher RV dP/dt is correlative to greater ventricular contractility. Therefore, in an example, at 2106, determining whether a contractility indicator exceeds a specified threshold value includes determining whether the RV dP/dt exceeds a specified threshold value. If so, the desired contractility is deemed to have been obtained, and process flow proceeds to 2108. At 2108, having achieved the desired contractility, the repetition frequency of CCM and neurostimulation can be decremented to save power. For example, if the CCM is being delivered every cardiac cycle, it can be decremented to be delivered every other cardiac cycle. If the neurostimulation is being delivered with a repeated 5 minutes on, followed by 5 minutes off, duty cycle, then it can be decremented to be delivered 5 minutes on followed by 6 minutes off. Process flow then continues back to 2106, where ongoing monitoring of the contractility indicator can continue. In this way, the CCM and neurostimulation therapy can be adjusted in a closed-loop fashion, such as to throttle back CCM and neurostimulation to save power once a desired contractility level has been achieved. In a further example, an initialization test can be carried out to determine the sensitivity of the contractility indication to each of the CCM and the neurostimulation repetition frequencies, and the amount by which the CCM and neurostimulation repetition frequencies are decremented, therefore, can be weighted using these respective sensitivities. In an example, one or more synergistic parameters described elsewhere in this document can be used to modify the CCM, such as at 2108.

Figure 21B:
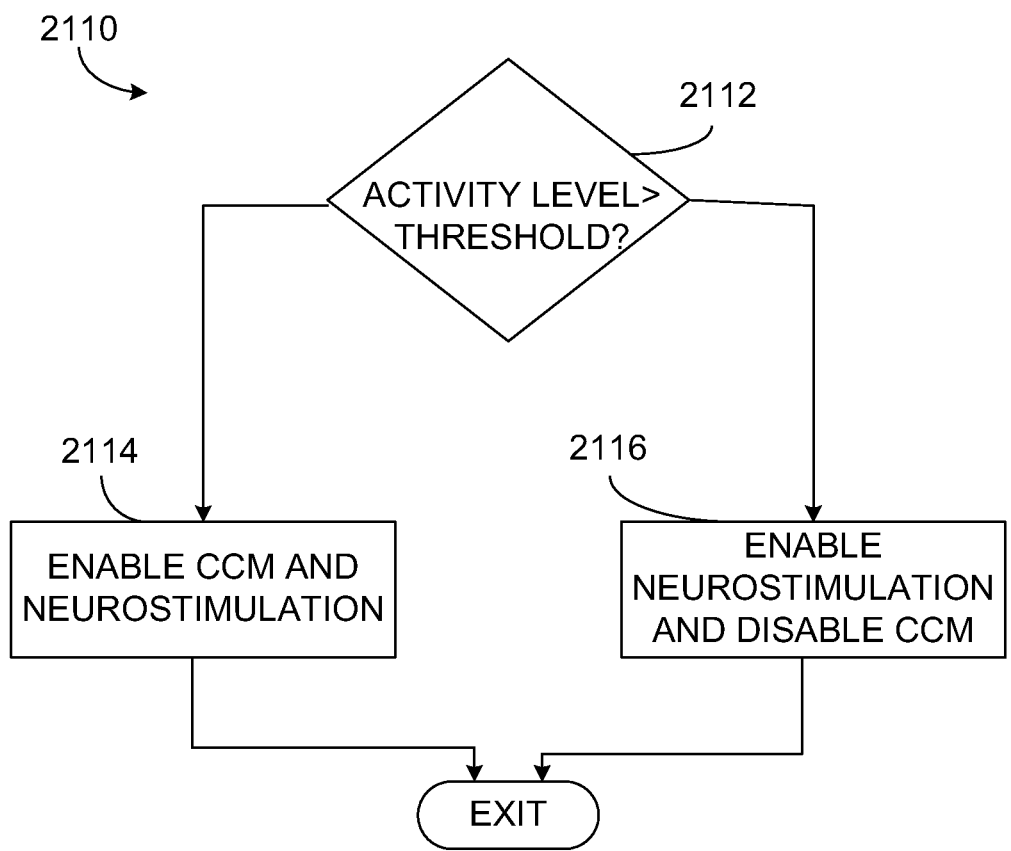
FIG. 21B shows an example of portions of a method for managing CCM and VNS or other neurostimulation

FIG. 21B shows an example of portions of a method 2110 for managing CCM and VNS or other neurostimulation. At 2112, it is determined whether an indication of the subject's physical activity level exceeds a threshold activity value, such as to determine whether the patient is physically active. At 2112, if the activity level exceeds the threshold value, then, at 2114, both CCM and neurostimulation are enabled. At 2112, if the activity level does not exceed the threshold value, then, at 2116, neurostimulation is enabled, and CCM is disabled, in this example.

Figure 21C:
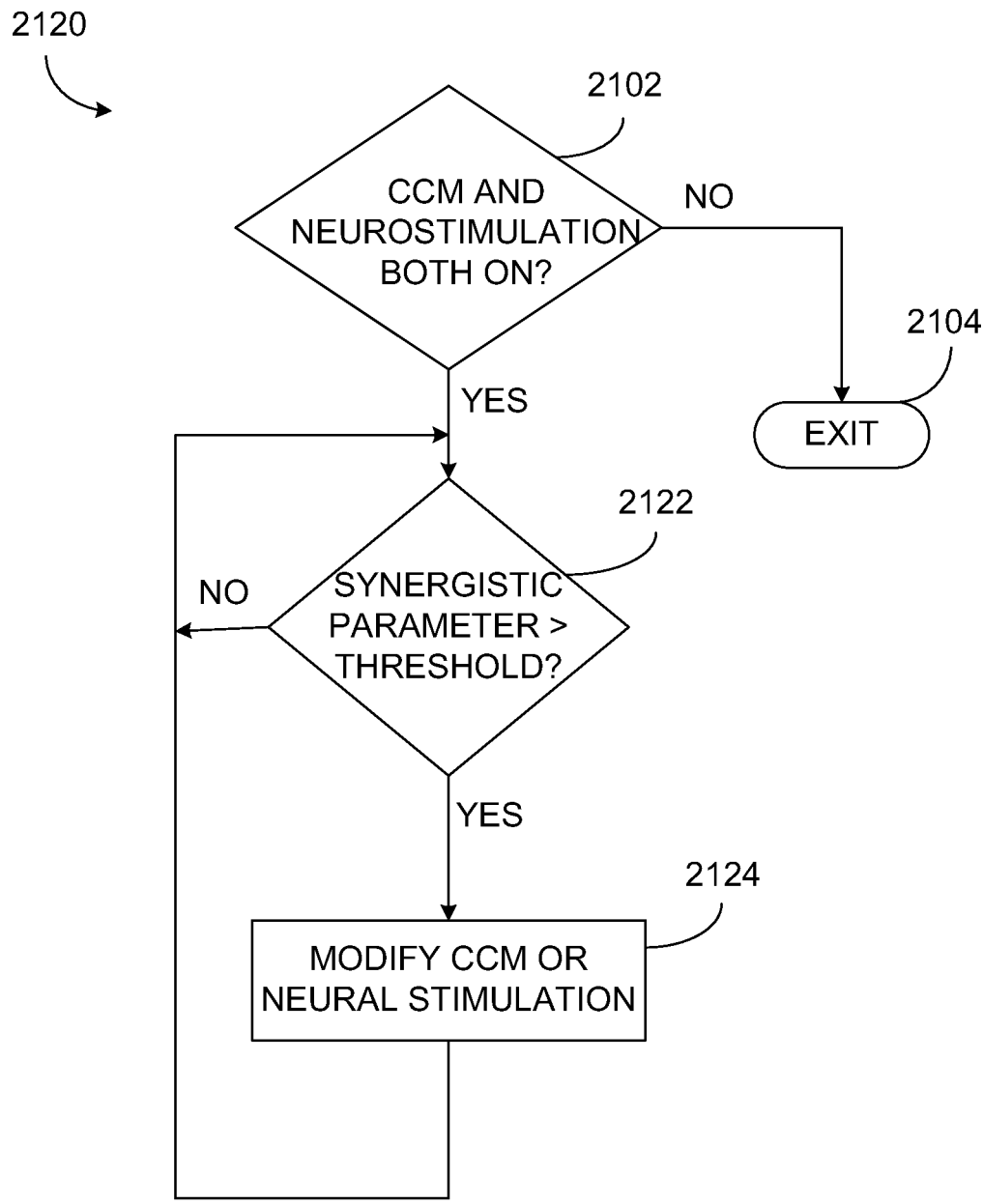
FIG. 21C shows an example of portions of a method for managing CCM and VNS or other neurostimulation.

FIG. 21C shows an example of portions of a method 2120 for managing CCM and VNS or other neurostimulation. At 2102, if CCM and neurostimulation are not both enabled, then the process exits at 2104. Otherwise, at 2122, it is determined whether a synergistic parameter exceeds a specified threshold value. Examples of synergistic parameters can include one or more hemodynamic parameters such as contractility, cardiac output, stoke volume, ejection fraction, or blood pressure. Other synergistic parameters can include one or more of a physiological parameter such as one or more electrolytes (e.g., sodium, potassium, calcium, chloride, bicarbonate), one or more inflammatory markers (e.g., C-reactive protein, tumor necrosis factor), creatinine, BUN, GFR, aldosterone, or naturetic peptides. If a threshold has been reached for a synergistic parameter (a weighted or other combined threshold can be used for multiple parameters), process flow proceeds to 2124. At 2124, having achieved the desired threshold, one or both of CCM or neurostimulation can be modified. For example, if the CCM is being delivered every cardiac cycle, it can be decremented to be delivered every other cardiac cycle. If the neurostimulation is being delivered with a duty cycle comprising 5 minutes on, followed by 5 minutes off, then it can be decremented, such as to be delivered using a duty cycle of 5 minutes on followed by 6 minutes off. Process flow then continues back to 2122, where ongoing monitoring of the synergistic parameter can continue. In this way, the CCM and neurostimulation therapy can be adjusted in a closed-loop fashion, such as to control the combined dose of CCM and neurostimulation therapies.

In an example, CCM and neurostimulation can be applied during the same cardiac cycle. This can help increase or maximize the total contractility enhancement provided by CCM and neurostimulation. CCM and neurostimulation can be applied during the same cardiac cycle even if the energy pulses used for these two therapies are not delivered simultaneously, concurrently, or in a manner that creates overlap among the two different therapies' energy pulses.

In an example, CCM and neurostimulation can be applied on different cardiac cycles. For example, CCM and neurostimulation can be applied on alternate cardiac cycles, such as to obtain benefit of both therapies while avoiding unwanted interaction between the two therapies. An example can specify the ratio of the cardiac cycles with CCM and those with neurostimulation (e.g., CCM applied on 2 cycles and then neurostimulation applied for 1 cycle). An example can specify a ratio of CCM therapy time vs. neurostimulation therapy time (e.g., CCM applied for two minutes, and then neurostimulation applied for 1 minute).

In another example, one or more adverse effects can be used to determine if either or both CCM and neurostimulation therapies are, or continue to be, delivered. For example, if both CCM and neurostimulation therapies are being delivered and an adverse effect of one of the CCM or neurostimulation therapies occurs, that particular therapy can be disabled. The remaining therapy can be altered (e.g., increased), such as to compensate for the loss of the other therapy. In another example, if only one of CCM and neurostimulation therapy is enabled, and an adverse effect associated with that therapy occurs, that therapy could be disabled and the other therapy enabled.

Examples of potential adverse effects associated with neurostimulation are bradycardia, voice alterations, pain or tingling in the throat or neck, cough, headache and ear pain, difficulty sleeping, weight change, shortness of breath, vomiting, facial flushing, dizziness, irritability, or functional degradation of organ innervated by the vagal nerve. In an example, one or more potentially adverse effects can be detected by a physiological sensor in the implanted cardiac rhythm/function management device 102, or located in a separate implanted device or local external device. In an example, bradycardia can be detected using an ECG signal amplifier in the device 102. In an example, cough or shortness of breath can be detected using a thoracic impedance or other respiration sensor of the device 102. In an example, weight change can be detected using a weight scale communicatively coupled to a local external user interface 104 or a remote external user interface 106. In an example, one or more other symptoms can be detected by querying the subject or otherwise receiving information from the subject or a caregiver, such as via a local external user interface 104.

Figure 21D:
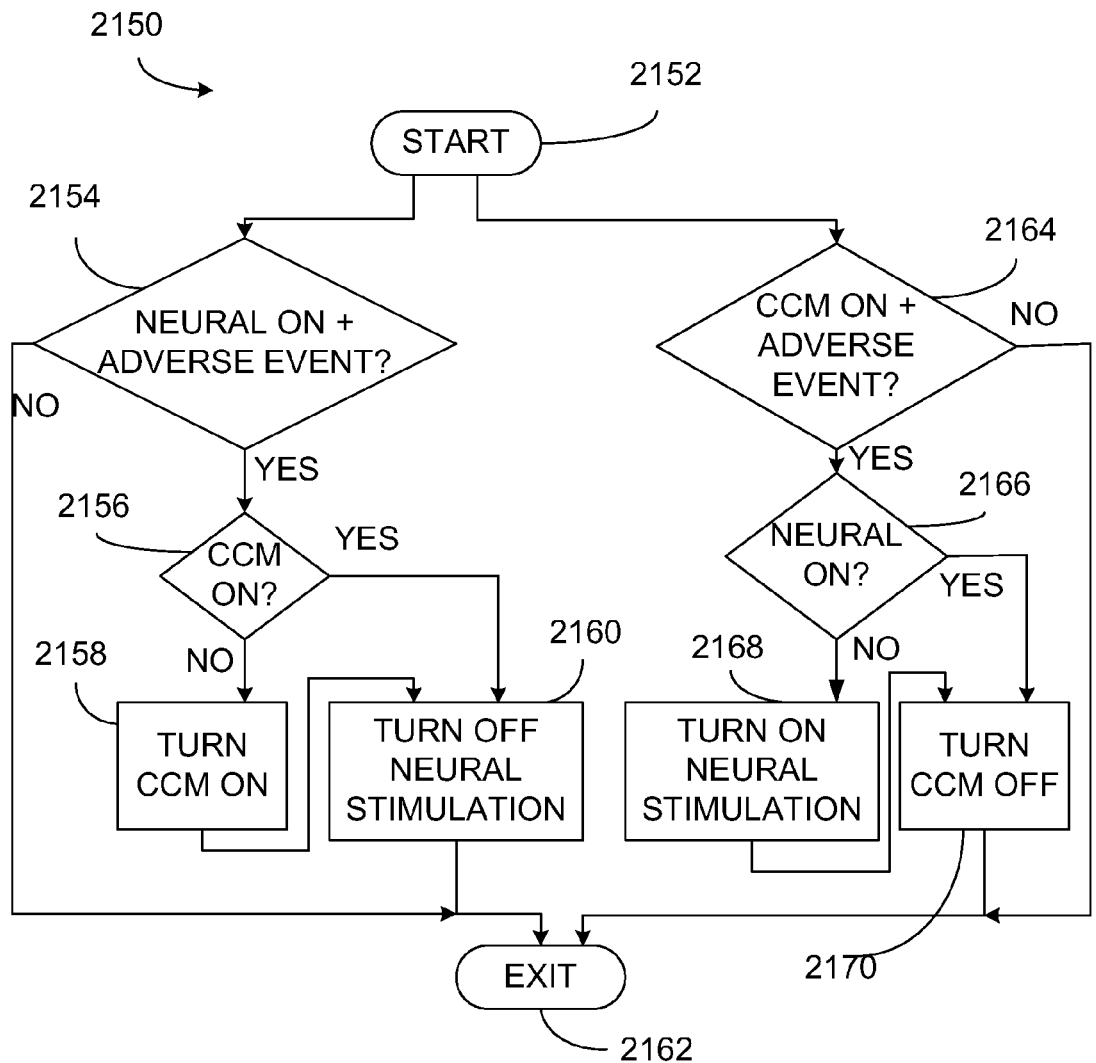
FIG. 21D shows examples of portions of a method for adjusting CCM or neural stimulation therapy at least in part in response to an adverse event associated with one of the CCM or neural stimulation therapy.

FIG. 21D shows examples of portions of a method 2150 for adjusting CCM or neural stimulation therapy at least in part in response to an adverse event associated with one of the CCM or neural stimulation therapy. At 2152, process flow begins, such as part of ongoing monitoring by a controller circuit 116 for an interrupt or other condition.

At 2154, if neural stimulation therapy is enabled and an adverse event associated with neural stimulation therapy occurs, then process flow continues at 2156, otherwise process flow exits at 2162, such as for more ongoing monitoring by the controller circuit 116. At 2156, with neural stimulation enabled and an associated adverse event having been detected, it is determined whether CCM is enabled. If so, then at 2160 neural stimulation is turned off, and process flow exits at 2162. Otherwise, at 2158, CCM is enabled and process flow continues to 2160 and neural stimulation is turned off and then process flow exits at 2162 for further monitoring.

At 2164, if CCM therapy is enabled and an adverse event associated with CCM therapy occurs, then process flow continues at 2166, otherwise process flow exits at 2162, such as for more ongoing monitoring by the controller circuit 116. At 2166, with CCM enabled and an associated adverse event having been detected, it is determined whether neural stimulation is enabled. If so, then at 2170 CCM is turned off, and process flow exits at 2162. Otherwise, at 2168, neural stimulation is enabled and process flow continues to 2170 and CCM is turned off and then process flow exits at 2162 for further monitoring.

18. Examples of Triggering and Inhibiting Conditions for CCM

The present inventor has recognized, among other things, that certain physiological or other conditions should trigger CCM therapy, for example, where CCM therapy can help provide a benefit under such conditions, and other physiological or other conditions should inhibit CCM therapy, for example, where CCM therapy could create additional stress or exacerbate such conditions.

Figure 22:
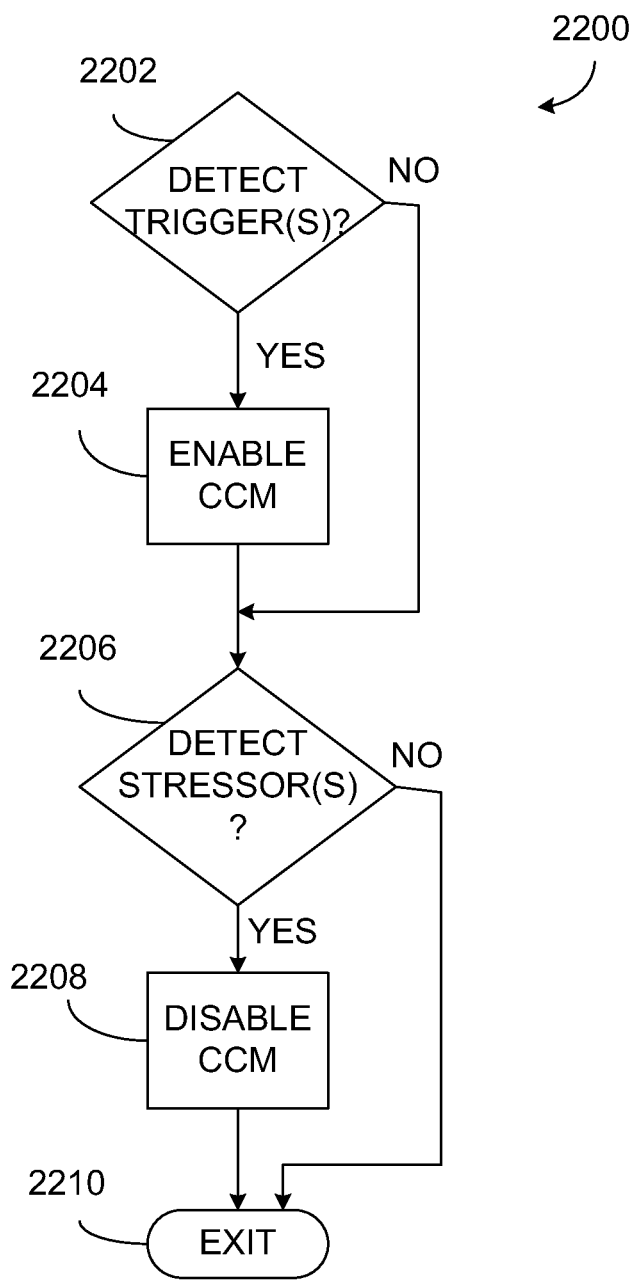
FIG. 22 shows an example of portions of a method of enabling or disabling CCM under appropriate conditions.

FIG. 22 shows an example of portions of a method 2200 of enabling or disabling CCM under appropriate conditions. At 2202, if a CCM trigger is detected, then, at 2204, CCM therapy is enabled, and process flow continues to 2206. Examples of such triggers can include the detection of an indication of worsening heart failure (e.g., onset or worsening of peripheral edema, pulmonary edema, or decreased cardiac output), worsening kidney function, dyspnea, physical activity below a specified threshold value, a physiological parameter (e.g. electrolyte) above or below a specified threshold range, worsening hemodynamic status (e.g. decreased rate of change of blood pressure, decreased cardiac output, decreased stroke volume, decreased blood pressure, or pulsus alternans), or the like. Other examples of CCM triggers can include the enabling or disabling of another device-based heart failure therapy (e.g. CRT or neurostimulation). Examples of device-based and external detection means of CCM triggers are illustrated in the following patents and applications, each of which is assigned to the assignee of the present patent application, the disclosures of which are incorporated herein by reference in their entirety: Zhu et al. U.S. Pat. No. 7,191,000 entitled "CARDIAC RHYTHM MANAGEMENT SYSTEM FOR EDEMA," Siejko et al. U.S. Pat. No. 7,115,096 entitled "THIRD HEART SOUND ACTIVITY INDEX FOR HEART FAILURE MONITORING," Belalcazar et al. U.S. patent application Ser. No. 11/469,018, now issued as U.S. Pat. No. 7,860,567, entitled "SENSOR FOR EDEMA," and Bardy et al. U.S. patent application Ser. No. 11/789,388, published on Aug. 30, 2007 as US Pat. Pub. No. 20070203415, entitled "SYSTEM AND METHOD FOR DETERMINING EDEMA THROUGH REMOTE PATIENT SENSING."

In an example, at 2204, enabling CCM therapy in response to the detection of a CCM trigger at 2202 can include adjusting one or more of CCM delivery timing, location, or energy. For example, in response to the detection of pulsus alternans, CCM therapy can be adjusted by increasing the frequency or energy of CCM, changing the electrode configuration used to deliver CCM, or adjusting the timing of CCM delivery within the refractory period.

At 2202, if no CCM trigger is detected, process flow continues to 2206. At 2206, if a stressor condition is detected, then, at 2208, CCM therapy is disabled, and process flow exits at 2210. Examples of such stressors can include detected sleep disordered breathing (e.g. apnea, hypopnea), ischemia, myocardial infarction, improving heart failure condition, a physiological parameter (e.g. electrolyte) above or below a specified threshold range, cardiac arrhythmia, physical activity exceeding a specified threshold value, magnetic resonance (MR) imaging, or the enabling or disabling of another device-based heart failure therapy (e.g. CRT or neurostimulation). At 2206, if no stressor condition is detected, then process flow exits at 2210. The method 2200 allows CCM to be appropriately used to respond to appropriate triggers, and to avoid creating additional cardiovascular stress under certain stressor conditions.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac rhythm/function management device comprising:
      a cardiac contractility modulation (CCM) therapy circuit configured to deliver a CCM therapy including a non-stimulatory electrical energy during a refractory period of the heart;
      an adverse event detector circuit including a CCM stressor detector circuit configured to detect a CCM stressor condition for disabling the CCM therapy, wherein the CCM stressor condition includes a detection of sleep disordered breathing; and
      a controller circuit, coupled to the CCM therapy circuit and the adverse event detector circuit, the controller circuit configured to obtain or provide information about a CCM condition and information about an adverse event, the controller circuit configured to adjust the CCM therapy using the information about the adverse event from the adverse event detector circuit, wherein the controller circuit is configured to disable the CCM therapy when or the sleep disordered breathing is detected.

2. The apparatus of claim 1, comprising a plurality of batteries and a non-CCM therapy circuit configured to deliver non-CCM therapy;
   wherein the adverse event detector circuit comprises a battery status circuit configured to determine battery status information; and
   wherein the controller circuit is configured to use the battery status information obtained from the battery status circuit to reconfigure which at least one of the plurality of batteries services at least one of the non-CCM therapy circuit or the CCM therapy circuit.

3. The apparatus of claim 1, comprising a non-CCM therapy circuit configured to deliver non-CCM therapy;
   wherein the adverse event detector circuit comprises a battery status circuit configured to determine battery status information; and
   wherein the controller circuit is configured to use the battery status information obtained from the battery status circuit to preferentially terminate delivery of one of the CCM therapy or the non-CCM therapy over the other of the CCM therapy or the non-CCM therapy.

4. The apparatus of claim 1, comprising a neurostimulation therapy circuit configured to deliver neurostimulation therapy;
   wherein the adverse event detector circuit is configured to detect an adverse event associated with at least one of neurostimulation or CCM; and
   wherein the controller circuit is configured to adjust at least one of the CCM therapy or the neurostimulation therapy based on the information from the adverse event detector circuit.

5. The apparatus of claim 4, wherein the controller circuit is configured such that when neurostimulation is enabled and an adverse event associated with the neurostimulation occurs, then the controller circuit (a) turns off neural stimulation when the CCM therapy is enabled; (b) enables the CCM therapy when the CCM therapy is not enabled and does not disable neural stimulation; or (c) enables the CCM therapy when the CCM therapy is not enabled and disables neural stimulation.

6. The apparatus of claim 4, wherein the controller circuit is configured such that when the CCM therapy is enabled and an adverse event associated with the CCM therapy occurs, then the controller circuit (a) turns off the CCM therapy when neurostimulation is enabled; (b) turns on neurostimulation when neurostimulation is not enabled and does not disable the CCM therapy; or (c) enables neurostimulation when neurostimulation is not enabled and disables the CCM therapy.

7. The apparatus of claim 1 wherein the adverse event detector circuit comprises a physiologic sensor.

8. The apparatus of claim 7, wherein the physiologic sensor is configured to detect pulsus alternans; and
   wherein the controller is configured to coordinate the CCM therapy circuit to adjust at least one of CCM energy, CCM delivery timing, CCM delivery location, or CCM electrode configuration in response to the detection of pulsus alternans.

9. The apparatus of claim 8, wherein the controller is configured to coordinate the CCM therapy circuit to increase at least one of CCM energy or frequency of CCM delivery in response to the detection of pulsus alternans.

10. The apparatus of claim 1, wherein the adverse event detector circuit comprises a user interface to receive user-input information about the adverse event.

11. The apparatus of claim 1, wherein the adverse event detector circuit comprises:
a CCM trigger detector circuit configured to detect a CCM trigger condition for enabling the CCM therapy; and
wherein the controller circuit is configured to enable the CCM therapy when at least one CCM trigger is detected.

12. The apparatus of claim 11, wherein the CCM trigger condition includes at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

13. The apparatus of claim 11, wherein the CCM trigger condition includes at least one of: (1) an indication of worsening heart failure, or (2) an indication of an enabling or disabling of a device-based heart failure therapy other than CCM therapy.

14. The apparatus of claim 1, wherein the CCM stressor condition further includes at least one of: a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

15. The apparatus of claim 1, wherein the CCM stressor condition includes at least one of: (1) an indication of enabling or disabling of a device-based heart failure therapy other than CCM therapy, or (2) a detected physical activity level that exceeds a specified threshold value.

16. The apparatus of claim 1, wherein the adverse event detector circuit comprises:
a CCM trigger detector circuit configured to detect a CCM trigger condition for enabling CCM; and
a CCM stressor detector circuit configured to detect a CCM stressor for disabling CCM; and
wherein the controller circuit is configured to enable the CCM therapy when at least one CCM trigger is detected and to disable CCM when at least one CCM stressor is detected.

17. The apparatus of claim 16, wherein the CCM trigger condition includes at least one of: an indication of worsening heart failure, an indication of worsening kidney function, an indication of worsening hemodynamic status, an indication of a measure of a physiological parameter that is above or below a specified value range, an indication of dyspnea, a detected physical activity level that is below a specified threshold value, or an indication of an enabling or disabling of a device-based heart failure therapy other than CCM therapy.

18. The apparatus of claim 16, wherein the CCM stressor condition includes at least one of: a detection of sleep disordered breathing, a detected myocardial ischemia, a detected myocardial infarction, an indication of improving heart failure status, an indication of a measure of a physiological parameter that is above or below a specified value range, an indication of enabling or disabling of a device-based heart failure therapy other than CCM therapy, a detected cardiac arrhythmia, a detected physical activity level that exceeds a specified threshold value, or a detected magnetic resonance imaging.

19. The apparatus of claim 16, wherein the CCM trigger condition includes at least one of: (1) an indication of worsening heart failure, or (2) an indication of an enabling or disabling of a device-based heart failure therapy other than CCM therapy; and
wherein the CCM stressor condition includes at least one of: (1) an indication of enabling or disabling of a device-based heart failure therapy other than CCM therapy, or (2) a detected physical activity level that exceeds a specified threshold value.

20. An apparatus comprising:
an implantable cardiac rhythm/function management device comprising:
a cardiac contractility modulation (CCM) therapy circuit configured to deliver a CCM therapy including a non-stimulatory electrical energy during a refractory period of the heart;
an adverse event detector circuit including a CCM stressor detector circuit configured to detect a CCM stressor for disabling the CCM therapy, wherein the CCM stressor includes a detected magnetic resonance imaging; and
a controller circuit, coupled to the CCM therapy circuit and the adverse event detector circuit, the controller circuit configured to obtain or provide information about a CCM condition and information about an adverse event, the controller circuit configured to adjust the CCM therapy using the information about the adverse event from the adverse event detector circuit, wherein the controller circuit is configured to disable the CCM therapy when a MRI is detected.

* * * * *